(12) United States Patent
Davis et al.

(10) Patent No.: US 7,972,372 B2
(45) Date of Patent: Jul. 5, 2011

(54) KIT FOR TREATING VASCULAR BIFURCATIONS

(75) Inventors: H. Richard Davis, Coral Springs, FL (US); Aaron Kaplan, Norwich, VT (US)

(73) Assignee: Tryton Medical, Inc., Durham, NC (US)

( * ) Notice: Subject to any disclaimer, the term of this patent is extended or adjusted under 35 U.S.C. 154(b) by 11 days.

(21) Appl. No.: 11/744,802

(22) Filed: May 4, 2007

(65) Prior Publication Data

US 2007/0213804 A1 Sep. 13, 2007

Related U.S. Application Data

(63) Continuation of application No. 10/584,968, filed as application No. PCT/US2005/036987 on Oct. 13, 2005, and a continuation of application No. 11/249,138, filed on Oct. 12, 2005, which is a continuation-in-part of application No. 11/190,514, filed on Jul. 27, 2005, which is a continuation-in-part of application No. 11/076,448, filed on Mar. 9, 2005, now Pat. No. 7,731,747, which is a continuation-in-part of application No. 10/807,643, filed on Mar. 23, 2004, now Pat. No. 7,481,834, said application No. 11/249,138 is a continuation-in-part of application No. 10/965,230, filed on Oct. 13, 2004, now Pat. No. 7,717,953.

(60) Provisional application No. 60/463,075, filed on Apr. 14, 2003.

(51) Int. Cl.
*A61F 2/06* (2006.01)

(52) U.S. Cl. ........................ 623/1.15; 623/1.16; 623/1.35

(58) Field of Classification Search ............... 623/1.11, 623/1.12, 1.15, 1.16, 1.35, 1.36, 1.42–1.46
See application file for complete search history.

(56) References Cited

U.S. PATENT DOCUMENTS

| | | | |
|---|---|---|---|
| 4,950,227 A | 8/1990 | Savin et al. | |
| 4,958,634 A | 9/1990 | Jang | |

(Continued)

FOREIGN PATENT DOCUMENTS

EP 0712 614 B1 5/1996

(Continued)

OTHER PUBLICATIONS

U.S. Appl. No. 10/807,643 and its prosecution history including the Office Actions mailed Nov. 10, 2004, Jul. 5, 2005, Feb. 15, 2006, Aug. 24, 2006, and Mar. 7, 2007 and the amendments filed Apr. 11, 2005, Nov. 23, 2005, Mar. 28, 2006, Dec. 4, 2006, and May 31, 2007.

(Continued)

*Primary Examiner* — (Jackie) Tan-Uyen T Ho
*Assistant Examiner* — Dianne Dornbusch
(74) *Attorney, Agent, or Firm* — Knobbe Martens Olson & Bear LLP

(57) ABSTRACT

A stepped balloon catheter prosthesis deployment system is disclosed for placement of a prosthesis across an Os opening from a main body lumen to a branch body lumen. The prosthesis comprises a radially expansible support at one end, a circumferentially extending link at the other end and at least one frond extending axially therebetween. The prosthesis is configured to be deployed from a stepped diameter balloon with the support in the branch body lumen, with the circumferentially extending link in the main lumen and the frond extendable across the Os.

22 Claims, 32 Drawing Sheets

U.S. PATENT DOCUMENTS

| | | | |
|---|---|---|---|
| 4,994,071 A | 2/1991 | MacGregor | |
| 5,071,406 A | 12/1991 | Jang | |
| 5,074,845 A | 12/1991 | Miraki et al. | |
| 5,102,417 A | 4/1992 | Palmaz | |
| 5,226,889 A | 7/1993 | Sheiban | |
| 5,304,132 A | 4/1994 | Jang | |
| 5,342,387 A | 8/1994 | Summers | |
| 5,383,892 A | 1/1995 | Cardon et al. | |
| 5,395,333 A | 3/1995 | Brill | |
| 5,415,635 A | 5/1995 | Bagaoisan et al. | |
| 5,507,769 A | 4/1996 | Marin et al. | |
| 5,522,882 A | 6/1996 | Gaterud et al. | |
| 5,540,712 A | 7/1996 | Kleshinski et al. | |
| 5,575,817 A | 11/1996 | Martin | |
| 5,593,442 A | 1/1997 | Klein | |
| 5,607,444 A | 3/1997 | Lam | |
| 5,609,605 A | 3/1997 | Marshall et al. | |
| 5,609,627 A | 3/1997 | Goicoechea et al. | |
| 5,613,980 A | 3/1997 | Chauhan | |
| 5,628,783 A | 5/1997 | Quiachon et al. | |
| 5,632,762 A | 5/1997 | Myler | |
| 5,632,772 A | 5/1997 | Alcime et al. | |
| 5,645,560 A | 7/1997 | Crocker et al. | |
| 5,656,036 A | 8/1997 | Palmaz | |
| 5,658,251 A | 8/1997 | Ressemann et al. | |
| 5,662,608 A | 9/1997 | Imran et al. | |
| 5,669,924 A | 9/1997 | Shaknovich | |
| 5,669,932 A | 9/1997 | Fischell et al. | |
| 5,713,917 A | 2/1998 | Leonhardt et al. | |
| 5,718,712 A | 2/1998 | Bonnal et al. | |
| 5,720,724 A | 2/1998 | Ressemann et al. | |
| 5,720,735 A | 2/1998 | Dorros | |
| 5,741,325 A | 4/1998 | Chaikof et al. | |
| 5,749,825 A | 5/1998 | Fischell et al. | |
| 5,749,851 A | 5/1998 | Wang | |
| 5,749,890 A | 5/1998 | Shaknovich | |
| 5,755,734 A | 5/1998 | Richter et al. | |
| 5,755,735 A | 5/1998 | Richter et al. | |
| 5,755,771 A | 5/1998 | Penn et al. | |
| 5,755,778 A | 5/1998 | Kleshinski | |
| 5,755,781 A * | 5/1998 | Jayaraman | 623/1.16 |
| 5,788,708 A | 8/1998 | Hegde et al. | |
| 5,810,871 A | 9/1998 | Tuckey et al. | |
| 5,824,052 A | 10/1998 | Khosravi et al. | |
| 5,827,320 A | 10/1998 | Richter et al. | |
| 5,843,116 A | 12/1998 | Crocker et al. | |
| 5,855,598 A | 1/1999 | Pinchuk | |
| 5,860,998 A | 1/1999 | Robinson et al. | |
| 5,868,777 A | 2/1999 | Lam | |
| 5,868,783 A | 2/1999 | Tower | |
| 5,891,191 A | 4/1999 | Stinson | |
| 5,893,887 A | 4/1999 | Jayaraman | |
| 5,897,588 A | 4/1999 | Hull et al. | |
| 5,906,640 A * | 5/1999 | Penn et al. | 623/1.15 |
| 5,906,641 A | 5/1999 | Thompson et al. | |
| 5,922,019 A | 7/1999 | Hankh et al. | |
| 5,961,546 A | 10/1999 | Robinson et al. | |
| 5,964,771 A | 10/1999 | Beyar et al. | |
| 5,967,971 A | 10/1999 | Bolser | |
| 5,968,089 A | 10/1999 | Krajicek | |
| 5,972,017 A * | 10/1999 | Berg et al. | 606/198 |
| 5,980,532 A | 11/1999 | Wang | |
| 6,004,347 A | 12/1999 | McNamara | |
| 6,017,363 A | 1/2000 | Hojeibane | |
| 6,027,486 A | 2/2000 | Crocker et al. | |
| 6,027,517 A | 2/2000 | Crocker et al. | |
| 6,033,434 A | 3/2000 | Borghi | |
| 6,033,435 A | 3/2000 | Penn et al. | |
| 6,048,361 A | 4/2000 | Von Oepen | |
| 6,051,020 A | 4/2000 | Goicoechea et al. | |
| 6,053,913 A | 4/2000 | Tu et al. | |
| 6,053,941 A | 4/2000 | Lindenburg et al. | |
| 6,056,775 A | 5/2000 | Borghi et al. | |
| 6,056,776 A | 5/2000 | Lau et al. | |
| 6,066,155 A | 5/2000 | Amann et al. | |
| 6,066,168 A | 5/2000 | Lau et al. | |
| 6,068,654 A | 5/2000 | Berg et al. | |
| 6,068,655 A | 5/2000 | Sequin et al. | |
| 6,077,297 A | 6/2000 | Robinson et al. | |
| 6,090,127 A | 7/2000 | Globerman | |
| 6,090,133 A | 7/2000 | Richter et al. | |
| 6,096,071 A * | 8/2000 | Yadav | 623/1.15 |
| 6,096,073 A | 8/2000 | Webster et al. | |
| 6,099,497 A | 8/2000 | Adams et al. | |
| 6,099,560 A | 8/2000 | Penn et al. | |
| 6,113,607 A | 9/2000 | Lau et al. | |
| 6,120,523 A | 9/2000 | Crocker et al. | |
| 6,127,597 A | 10/2000 | Beyar et al. | |
| 6,129,738 A | 10/2000 | Lashinski et al. | |
| 6,156,052 A | 12/2000 | Richter et al. | |
| 6,159,238 A | 12/2000 | Killion et al. | |
| 6,162,243 A | 12/2000 | Gray et al. | |
| 6,165,195 A | 12/2000 | Wilson et al. | |
| 6,168,617 B1 | 1/2001 | Blaeser et al. | |
| 6,183,509 B1 | 2/2001 | Dibie | |
| 6,206,910 B1 | 3/2001 | Berry et al. | |
| 6,210,429 B1 | 4/2001 | Vardi et al. | |
| 6,214,036 B1 | 4/2001 | Letendre et al. | |
| 6,221,080 B1 | 4/2001 | Power | |
| 6,221,096 B1 | 4/2001 | Aiba et al. | |
| 6,221,098 B1 | 4/2001 | Wilson et al. | |
| 6,231,543 B1 | 5/2001 | Hegde et al. | |
| 6,241,738 B1 | 6/2001 | Dereume et al. | |
| 6,241,744 B1 | 6/2001 | Imran et al. | |
| 6,254,593 B1 | 7/2001 | Wilson | |
| 6,258,116 B1 | 7/2001 | Hojeibane | |
| 6,261,305 B1 | 7/2001 | Marotta et al. | |
| 6,261,316 B1 | 7/2001 | Shaolian et al. | |
| 6,264,682 B1 | 7/2001 | Wilson et al. | |
| 6,264,686 B1 | 7/2001 | Rieu et al. | |
| 6,267,783 B1 | 7/2001 | Letendre et al. | |
| 6,270,525 B1 | 8/2001 | Letendre et al. | |
| 6,280,412 B1 | 8/2001 | Pederson, Jr. et al. | |
| 6,287,315 B1 | 9/2001 | Wijeratne et al. | |
| 6,287,336 B1 | 9/2001 | Globerman et al. | |
| 6,290,728 B1 | 9/2001 | Phelps et al. | |
| 6,293,964 B1 | 9/2001 | Yadav | |
| 6,325,826 B1 | 12/2001 | Vardi et al. | |
| 6,331,186 B1 | 12/2001 | Wang et al. | |
| 6,344,052 B1 | 2/2002 | Greenan et al. | |
| 6,346,089 B1 | 2/2002 | Dibie | |
| 6,352,551 B1 | 3/2002 | Wang | |
| 6,361,544 B1 | 3/2002 | Wilson et al. | |
| 6,383,212 B2 | 5/2002 | Durcan et al. | |
| 6,383,213 B2 | 5/2002 | Wilson et al. | |
| 6,387,120 B2 | 5/2002 | Wilson et al. | |
| 6,391,032 B2 | 5/2002 | Blaeser et al. | |
| 6,395,008 B1 | 5/2002 | Ellis et al. | |
| 6,402,778 B2 | 6/2002 | Wang | |
| 6,409,741 B1 | 6/2002 | Crocker et al. | |
| 6,409,750 B1 | 6/2002 | Hyodoh et al. | |
| 6,409,755 B1 | 6/2002 | Vrba | |
| 6,409,757 B1 | 6/2002 | Trout, III et al. | |
| 6,428,567 B2 | 8/2002 | Wilson et al. | |
| 6,436,104 B2 | 8/2002 | Hojeibane | |
| 6,436,134 B2 | 8/2002 | Richter et al. | |
| 6,440,165 B1 | 8/2002 | Richter et al. | |
| 6,451,050 B1 | 9/2002 | Rudakov et al. | |
| 6,478,814 B2 | 11/2002 | Wang et al. | |
| 6,482,211 B1 | 11/2002 | Choi | |
| 6,482,227 B1 | 11/2002 | Solovay | |
| 6,485,509 B2 | 11/2002 | Killion et al. | |
| 6,488,700 B2 | 12/2002 | Klumb et al. | |
| 6,508,836 B2 | 1/2003 | Wilson et al. | |
| 6,517,558 B2 * | 2/2003 | Gittings et al. | 606/153 |
| 6,524,335 B1 | 2/2003 | Hartley et al. | |
| 6,540,779 B2 | 4/2003 | Richter et al. | |
| 6,547,813 B2 | 4/2003 | Stiger et al. | |
| 6,554,856 B1 | 4/2003 | Doorly et al. | |
| 6,562,061 B1 | 5/2003 | Wang et al. | |
| 6,565,597 B1 | 5/2003 | Fearnot et al. | |
| 6,572,649 B2 | 6/2003 | Berry et al. | |
| 6,579,312 B2 | 6/2003 | Wilson et al. | |
| 6,579,314 B1 | 6/2003 | Lombardi et al. | |
| 6,582,394 B1 | 6/2003 | Reiss et al. | |
| 6,589,274 B2 | 7/2003 | Stiger et al. | |
| 6,596,020 B2 | 7/2003 | Vardi et al. | |

| | | |
|---|---|---|
| 6,599,316 B2 | 7/2003 | Vardi et al. |
| 6,607,552 B1 | 8/2003 | Hanson |
| 6,626,934 B2 | 9/2003 | Blaeser et al. |
| 6,637,107 B2 | 10/2003 | Yasuhara et al. |
| 6,652,580 B1 | 11/2003 | Chuter et al. |
| 6,656,215 B1 | 12/2003 | Yanez et al. |
| 6,656,216 B1 | 12/2003 | Hossainy et al. |
| 6,663,665 B2 | 12/2003 | Shaolian et al. |
| 6,663,666 B1 | 12/2003 | Quiachon et al. |
| 6,673,104 B2 | 1/2004 | Barry |
| 6,673,106 B2 | 1/2004 | Mitelberg et al. |
| 6,673,107 B1 | 1/2004 | Brandt et al. |
| 6,682,557 B1 | 1/2004 | Quiachon et al. |
| 6,706,062 B2 | 3/2004 | Vardi et al. |
| 6,726,714 B2 | 4/2004 | DiCaprio et al. |
| 6,740,113 B2 | 5/2004 | Vrba |
| 6,756,094 B1 | 6/2004 | Wang |
| 6,764,504 B2 | 7/2004 | Wang |
| 6,770,092 B2 | 8/2004 | Richter |
| 6,790,224 B2 | 9/2004 | Gerberding |
| 6,805,697 B1 | 10/2004 | Helm et al. |
| 6,805,702 B1 | 10/2004 | Chen et al. |
| 6,824,553 B1 | 11/2004 | Samson et al. |
| 6,830,575 B2 | 12/2004 | Stenzel et al. |
| 6,843,802 B1 | 1/2005 | Villalobos et al. |
| 6,852,116 B2 | 2/2005 | Leonhardt et al. |
| 6,872,215 B2 | 3/2005 | Crocker et al. |
| 6,887,268 B2 | 5/2005 | Butaric et al. |
| 6,911,038 B2 | 6/2005 | Mertens et al. |
| 6,926,690 B2 * | 8/2005 | Renati ........................ 604/8 |
| 6,932,837 B2 * | 8/2005 | Amplatz et al. ............ 623/1.15 |
| 6,986,786 B1 | 1/2006 | Smith |
| 7,481,834 B2 | 1/2009 | Kaplan et al. |
| 7,578,841 B2 | 8/2009 | Yadin et al. |
| 7,717,953 B2 | 5/2010 | Kaplan et al. |
| 7,731,747 B2 | 6/2010 | Kaplan et al. |
| 7,758,630 B2 | 7/2010 | Davis et al. |
| 2001/0003161 A1 * | 6/2001 | Vardi et al. .................. 623/1.11 |
| 2001/0008976 A1 | 7/2001 | Wang |
| 2001/0011188 A1 | 8/2001 | Berry et al. |
| 2001/0020181 A1 | 9/2001 | Layne |
| 2001/0023356 A1 | 9/2001 | Raz et al. |
| 2001/0037137 A1 | 11/2001 | Vardi et al. |
| 2001/0041930 A1 | 11/2001 | Globerman et al. |
| 2002/0058984 A1 | 5/2002 | Butaric et al. |
| 2002/0058993 A1 | 5/2002 | Landau et al. |
| 2002/0077692 A1 | 6/2002 | Besselink |
| 2002/0111619 A1 | 8/2002 | Keast et al. |
| 2002/0116047 A1 | 8/2002 | Vardi et al. |
| 2002/0151959 A1 | 10/2002 | Von Oepen |
| 2002/0156516 A1 | 10/2002 | Vardi et al. |
| 2002/0165602 A1 * | 11/2002 | Douglas et al. ............ 623/1.13 |
| 2002/0169498 A1 | 11/2002 | Kim et al. |
| 2002/0173840 A1 | 11/2002 | Brucker et al. |
| 2002/0183763 A1 * | 12/2002 | Callol et al. .................. 606/108 |
| 2002/0183780 A1 | 12/2002 | Wang |
| 2002/0193862 A1 | 12/2002 | Mitelberg et al. |
| 2002/0193868 A1 | 12/2002 | Mitelberg et al. |
| 2002/0198559 A1 | 12/2002 | Mistry et al. |
| 2003/0083734 A1 | 5/2003 | Friedrich et al. |
| 2003/0097171 A1 | 5/2003 | Elliott |
| 2003/0114912 A1 | 6/2003 | Seguin et al. |
| 2003/0125797 A1 | 7/2003 | Chobotov et al. |
| 2003/0125799 A1 | 7/2003 | Limon |
| 2003/0199967 A1 | 10/2003 | Hartley et al. |
| 2004/0015227 A1 | 1/2004 | Vardi et al. |
| 2004/0024441 A1 | 2/2004 | Bertolino et al. |
| 2004/0054362 A1 | 3/2004 | Lopath et al. |
| 2004/0054396 A1 | 3/2004 | Hartley et al. |
| 2004/0073250 A1 | 4/2004 | Pederson, Jr. et al. |
| 2004/0093058 A1 * | 5/2004 | Cottone et al. ............. 623/1.11 |
| 2004/0106985 A1 * | 6/2004 | Jang .......................... 623/1.16 |
| 2004/0133261 A1 | 7/2004 | Bigus et al. |
| 2004/0133268 A1 | 7/2004 | Davidson et al. |
| 2004/0138730 A1 | 7/2004 | Mitelberg et al. |
| 2004/0138737 A1 | 7/2004 | Davidson et al. |
| 2004/0143209 A1 * | 7/2004 | Liu et al. ........................ 604/8 |
| 2004/0158306 A1 | 8/2004 | Mitelberg et al. |
| 2004/0204754 A1 | 10/2004 | Kaplan et al. |
| 2004/0220655 A1 | 11/2004 | Swanson et al. |
| 2004/0249434 A1 | 12/2004 | Andreas et al. |
| 2004/0254627 A1 * | 12/2004 | Thompson et al. .......... 623/1.11 |
| 2004/0260378 A1 | 12/2004 | Goshgarian |
| 2004/0260383 A1 | 12/2004 | Stelter et al. |
| 2005/0010278 A1 | 1/2005 | Vardi et al. |
| 2005/0015108 A1 | 1/2005 | Williams et al. |
| 2005/0049678 A1 | 3/2005 | Cocks et al. |
| 2005/0154447 A1 | 7/2005 | Goshgarian |
| 2005/0159803 A1 * | 7/2005 | Lad et al. ..................... 623/1.13 |
| 2005/0165469 A1 * | 7/2005 | Hogendijk ................... 623/1.15 |
| 2005/0192656 A1 | 9/2005 | Eidenschink |
| 2005/0203563 A9 | 9/2005 | Pederson, Jr. et al. |
| 2005/0209674 A1 | 9/2005 | Kutscher et al. |
| 2005/0228483 A1 | 10/2005 | Kaplan et al. |
| 2005/0234536 A1 | 10/2005 | Mitelberg et al. |
| 2005/0251195 A1 | 11/2005 | Wang |
| 2005/0261722 A1 | 11/2005 | Crocker et al. |
| 2005/0288769 A1 | 12/2005 | Globerman |
| 2006/0025849 A1 | 2/2006 | Kaplan et al. |
| 2006/0079952 A1 | 4/2006 | Kaplan et al. |
| 2006/0079956 A1 * | 4/2006 | Eigler et al. ................. 623/1.35 |
| 2006/0116748 A1 | 6/2006 | Kaplan et al. |
| 2007/0203571 A1 | 8/2007 | Kaplan et al. |
| 2007/0213803 A1 | 9/2007 | Kaplan et al. |
| 2007/0276460 A1 | 11/2007 | Davis et al. |
| 2007/0288082 A1 | 12/2007 | Williams |
| 2008/0015610 A1 | 1/2008 | Kaplan et al. |
| 2008/0015678 A1 | 1/2008 | Kaplan et al. |
| 2008/0183269 A2 | 7/2008 | Kaplan et al. |
| 2008/0294240 A1 | 11/2008 | Casey |
| 2009/0163988 A1 | 6/2009 | Kaplan et al. |
| 2009/0163999 A1 | 6/2009 | Kaplan et al. |
| 2009/0326641 A1 | 12/2009 | Davis et al. |

FOREIGN PATENT DOCUMENTS

| | | |
|---|---|---|
| EP | 0505686 | 11/1996 |
| EP | 0540290 | 1/1998 |
| EP | 0876 805 A2 | 11/1998 |
| EP | 0 959 811 B1 | 1/1999 |
| EP | 1 325 715 A2 | 9/2003 |
| EP | 1 325 716 A1 | 9/2003 |
| EP | 1 325 717 A2 | 9/2003 |
| EP | 1 362 564 A1 | 11/2003 |
| EP | 1 433 441 A2 | 6/2004 |
| EP | 1 512 381 A2 | 3/2005 |
| WO | WO 96/38101 | 12/1996 |
| WO | WO 97/17101 A1 | 5/1997 |
| WO | WO 98/19629 A2 | 5/1998 |
| WO | WO 98/24503 | 6/1998 |
| WO | WO 00/15147 A1 | 3/2000 |
| WO | WO 00/69367 | 11/2000 |
| WO | WO 02/47580 A2 | 6/2002 |
| WO | WO 02/49538 A2 | 6/2002 |
| WO | WO 03/039626 A2 | 5/2003 |
| WO | WO 2004/026180 A2 | 4/2004 |
| WO | WO 2004/058100 A2 | 7/2004 |
| WO | WO 2004/089249 A1 | 10/2004 |
| WO | WO 2004/091428 A3 | 10/2004 |
| WO | WO 2004/103217 A1 | 12/2004 |

OTHER PUBLICATIONS

U.S. Appl. No. 10/965,230 and its prosecution history including the Office Action mailed Jan. 10, 2007 and the amendment filed Apr. 6, 2007.

A New Team to Fight Arterial Disease, *Building Innovation & Construction Technology*, No. 10, Dec. 1999, http://www.cmit.csiro.au/innovation/1999-12/arterial.htm.

Endovascular Grafts: History of Minimally Invasive Treatment of Vascular Disease, Timothy A.M. Chuter, *Endoluminal Vascular Prostheses*, pp. 3-17, 1995.

Esophageal Strictures: Treatment with a New Design of Modified Gianturco Stent, Ho. Young Song, M.D. et al., *Radiology*, vol. 184, No. 3, pp. 729-734 Sep. 1992.

International Search Report in PCT Application No. PCT/US05/36987 dated Jun. 5, 2006.

International Search Report and Written Opinion in PCT Application No. PCT/US04/10591 dated Mar. 11, 2005 in 6 pages.

Protection of Side-Branches in Coronary Lesions With a New Stent Design, Stephan Baldus, MD et al., *Catherization and Cardiovascular Diagnosis*, vol. 45: No. 4, 456-459, Dec. 1998.

Self-expanding Stainless Steel Biliary Stents, Harold G. Coons, MD *Radiology*, vol. 170, No. 3, Part 2, pp. 979-983, Mar. 1989.

Supplementary European Search Report for Application No. EP 04759166.4 dated Mar. 5, 2007 in 4 pages.

*The Impact of Stent Design on Proximal Stent-graft Fixation in the Abdominal Aorta: an Experimental Study*, T. Resch et al., European Journal of Vascular and Endovascular Surgery, vol. 20, No. 2, pp. 190-195, Aug. 2000.

The Zenith endoluminal stent-graft system: suprarenal fixation, safety features, modular components, fenestration and custom crafting, Michael M.D. Lawrence-Brown et al., *Vascular and Endovascular Surgical Techniques*, Fourth Edition, pp. 219-223, 2001.

U.S. Appl. No. 11/603,338, filed Nov. 21, 2006.

U.S. Appl. No. 10/584,968, filed Jun. 30, 2006.

U.S. Appl. No. 11/744,796, filed May 4, 2007.

U.S. Appl. No. 11/744,812, filed May 4, 2007.

European Patent Office Communication (first substantive examination report) in Application No. 04 759 166.4—1526 dated Apr. 30, 2007 in 3 pages.

U.S. Appl. No. 11/781,201, filed Jul. 20, 2007.

U.S. Appl. No. 11/781,164, filed Jul. 20, 2007.

U.S. Appl. No. 10/807,643 and its prosecution history including the Office Action mailed Aug. 8, 2007.

U.S. Appl. No. 10/807,643 and its prosecution history including the Amendment filed Dec. 5, 2007 and the Office Action mailed Feb. 26, 2008 and the Amendment filed Aug. 22, 2008.

U.S. Appl. No. 11/076,448 and its prosecution history including the Office Action mailed May 1, 2008 and the Amendment filed Aug. 22, 2008.

U.S. Appl. No. 10/965,230 and its prosecution history including the Office Action mailed Nov. 30, 2007 and the Amendment filed Mar. 18, 2008.

U.S. Appl. No. 11/744,812 and its prosecution history including the Office Action mailed Apr. 7, 2008 and the Amendment filed Jul. 14, 2008.

International Search Report and Written Opinion in PCT Application No. PCT/US07/85429 dated Jun. 2, 2008 in 10 pages.

U.S. Appl. No. 10/584,968 and its prosecution history including the Office Action mailed Apr. 11, 2008 and the Amendment filed Jul. 14, 2008.

U.S. Appl. No. 11/076,448 and its prosecution history including the Office Actions mailed May 1, 2008, Nov. 28, 2008, and May 13, 2009, the Amendments filed Aug. 22, 2008, Feb. 18, 2009, and May 22, 2009, and the Notice of Allowances mailed Oct. 26, 2009 and Feb. 18, 2010.

U.S. Appl. No. 10/965,230 and its prosecution history including the RCE and Amendment filed Apr. 8, 2009, the Office Action mailed Jun. 17, 2009, the Amendment filed Aug. 19, 2009 and the Notice of Allowance mailed Jan. 6, 2010.

U.S. Appl. No. 11/190,514 and its prosecution history including the Office Actions mailed Dec. 5, 2008, Apr. 2, 2009 and Nov. 2, 2009 and the Amendments filed Jan. 29, 2009, Jun. 30, 2009 and Dec. 18, 2009.

U.S. Appl. No. 11/249,138 and its prosecution history including the Office Actions mailed Dec. 5, 2008, Mar. 20, 2009, and Oct. 15, 2009 and the Amendments filed Jan. 29, 2009 and Jun. 30, 2009 and Dec. 15, 2009.

U.S. Appl. No. 11/744,812 and its prosecution history including the Office Actions mailed Apr. 7, 2008, Oct. 10, 2008, and Mar. 17, 2009, and Oct. 27, 2009 and the Amendments filed Jul. 14, 2008, Nov. 20, 2008, Jun. 30, 2009, and Mar. 1, 2010.

U.S. Appl. No. 11/744,796 and its prosecution history including the Office Actions mailed Apr. 7, 2009, and Oct. 27, 2009 and the Amendment filed Jul. 6, 2009 and Mar. 1, 2010.

U.S. Appl. No. 11/781,164 and its prosecution history including the Office Actions mailed Jun. 17, 2009 and Dec. 9, 2009 and the Amendment filed Aug. 19, 2009 and Feb. 9, 2010.

U.S. Appl. No. 10/584,968 and its prosecution history including the Office Actions mailed Apr. 11, 2008, Oct. 7, 2008, Mar. 20, 2009 and Nov. 23, 2009 and the Amendments filed Jul. 14, 2008, Nov. 17, 2008, Jul. 6, 2009, and Mar. 23, 2010.

U.S. Appl. No. 12/362,342 and its prosecution history.

Serruys, Patrick W et al.; Handbook of Coronary Stents; Jan. 15, 2002; pp. 130-131; Martin Dunitz, Ltd.; London, UK.

Supplemental European Search Report for Application No. EP 05 81 2396 mailed Nov. 18, 2009 in 7 pages.

U.S. Appl. No. 12/362,300 and its prosecution history.

Copending U.S. Appl. No. 12/829,217 filed Jul. 1, 2010.

Copending U.S. Appl. No. 12/829,193 filed Jul. 1, 2010.

International Search Report and Written Opinion in Application No. PCT/US10/40962 dated Oct. 13, 2010, in 14 pages.

\* cited by examiner

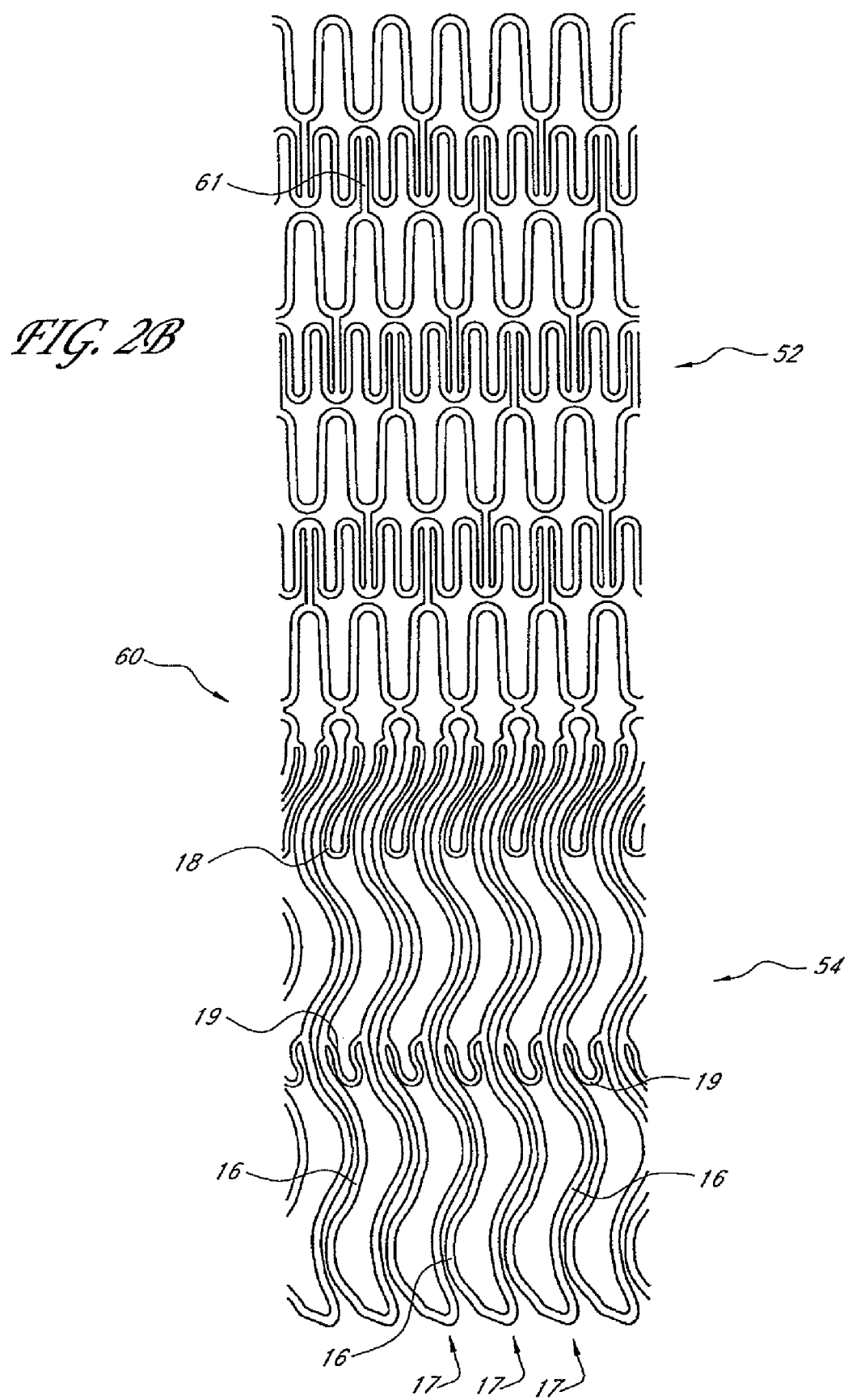

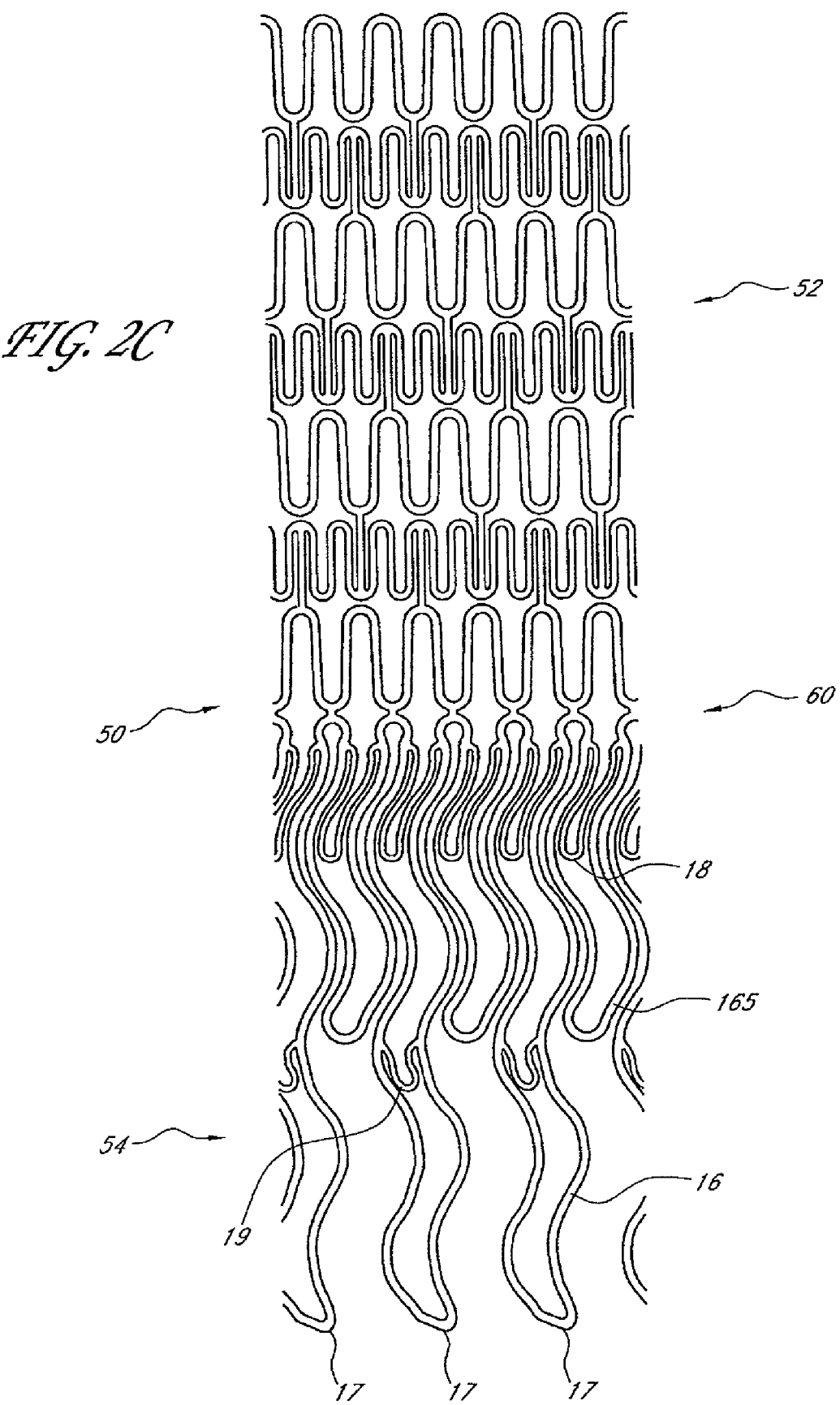

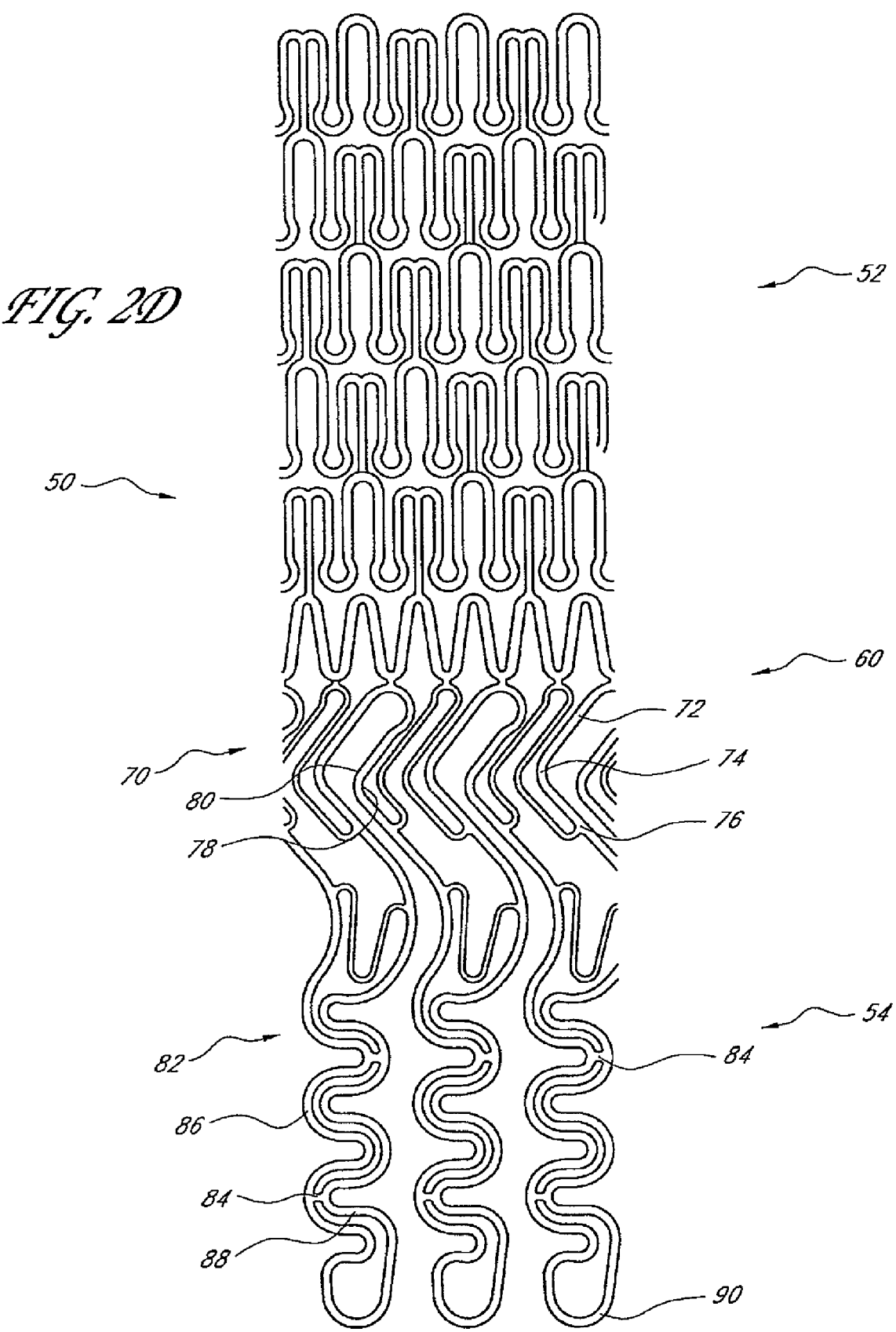

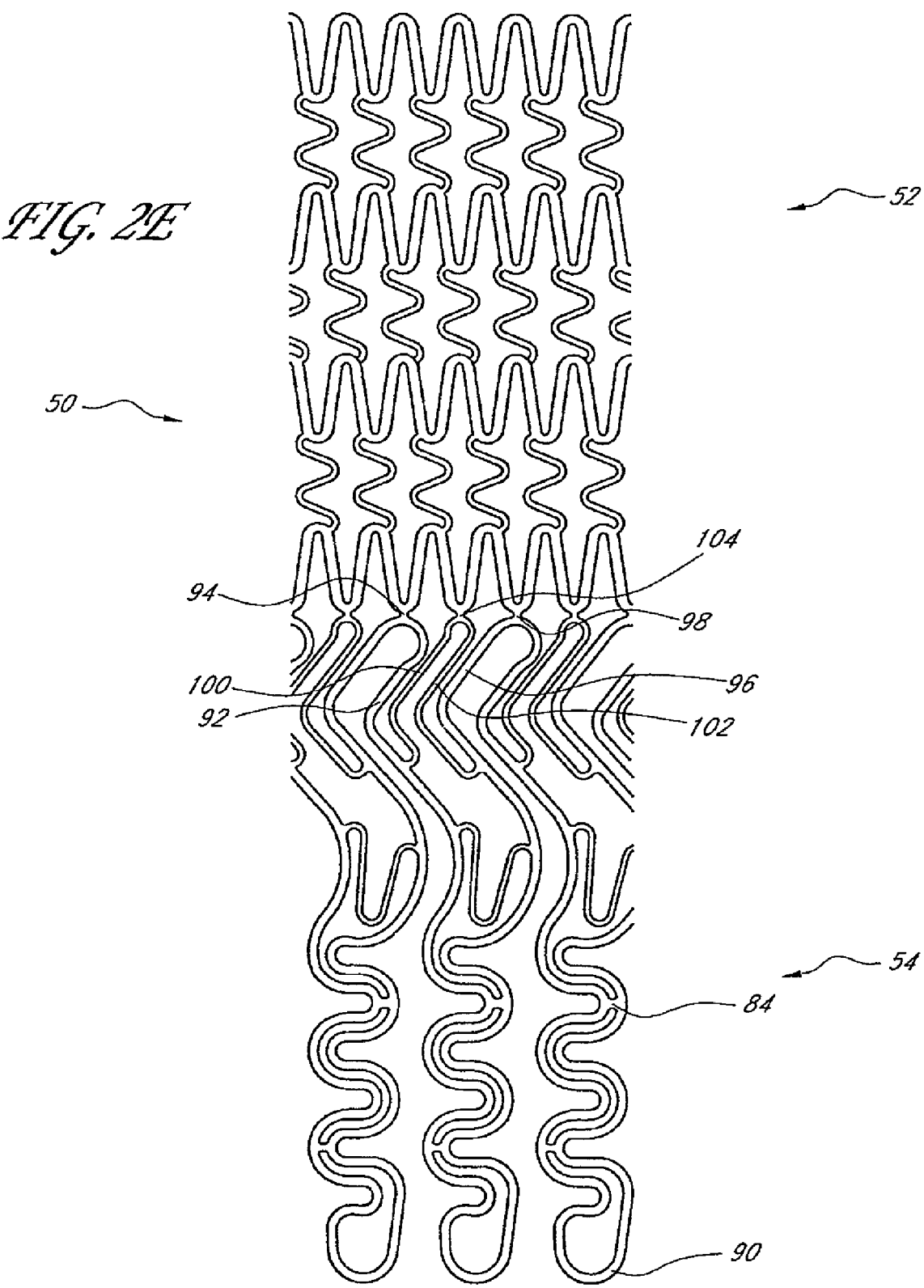

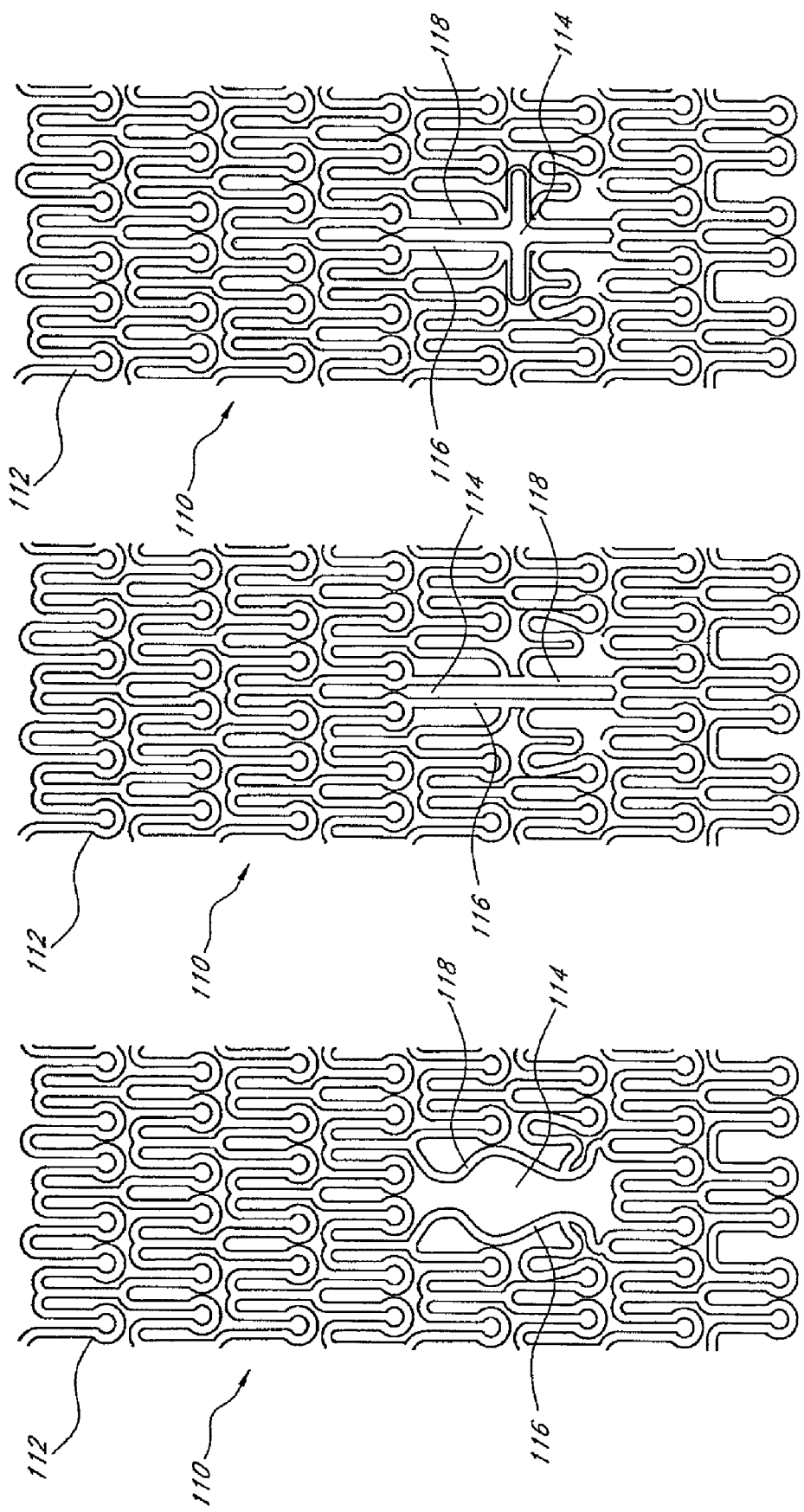

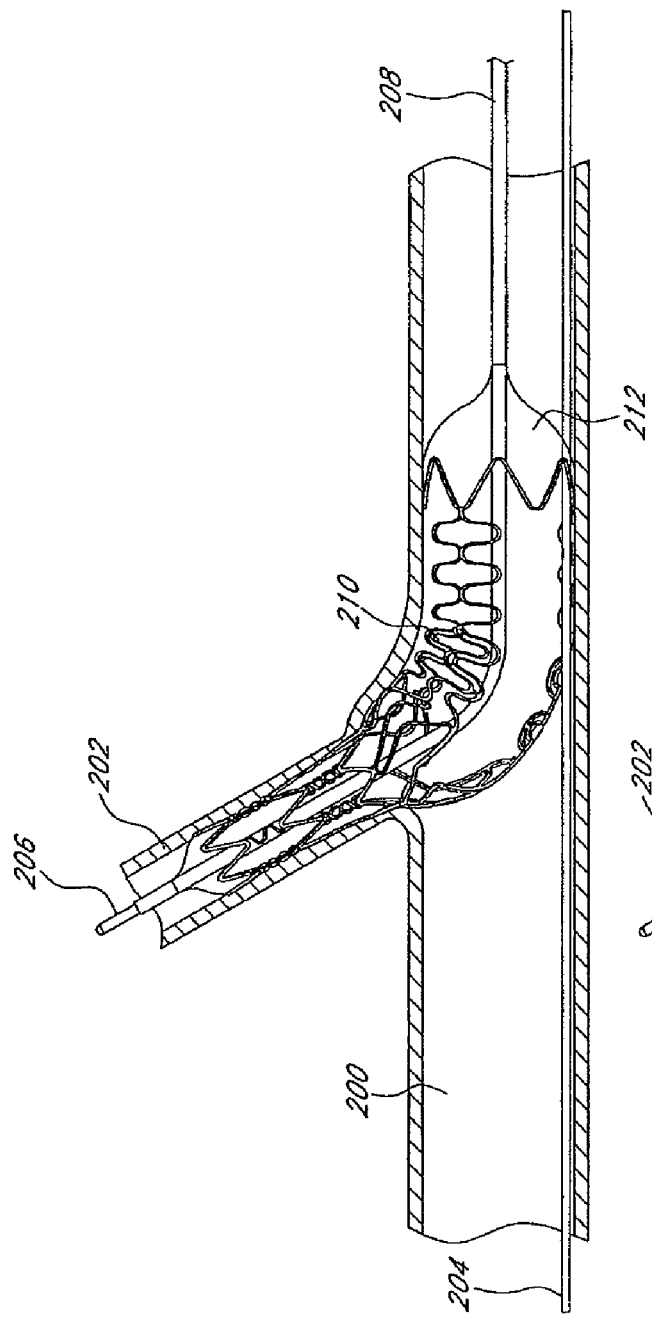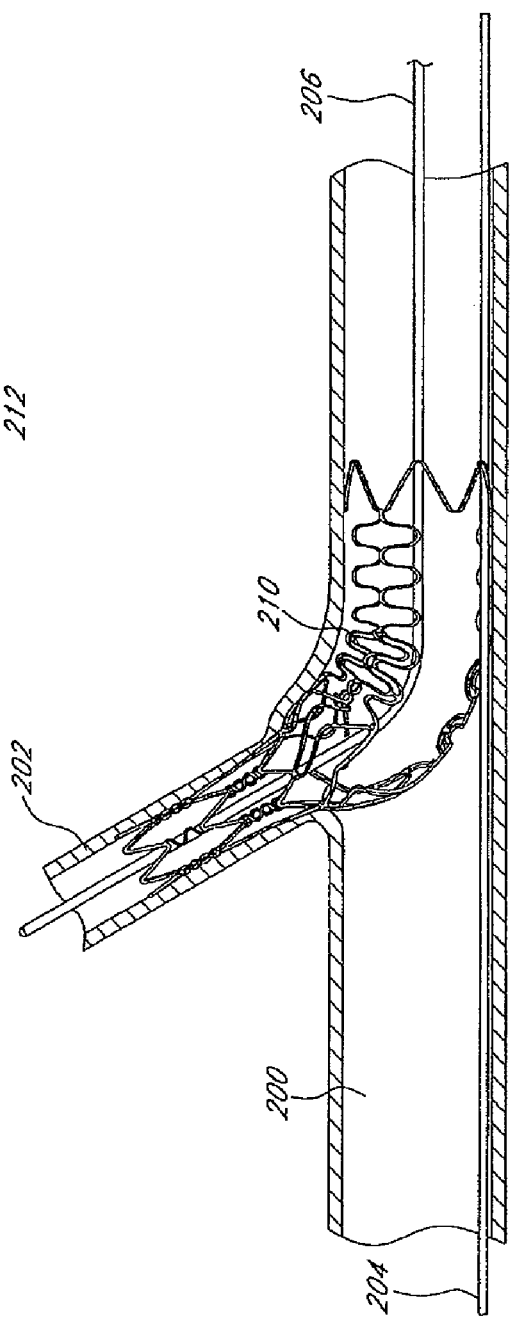

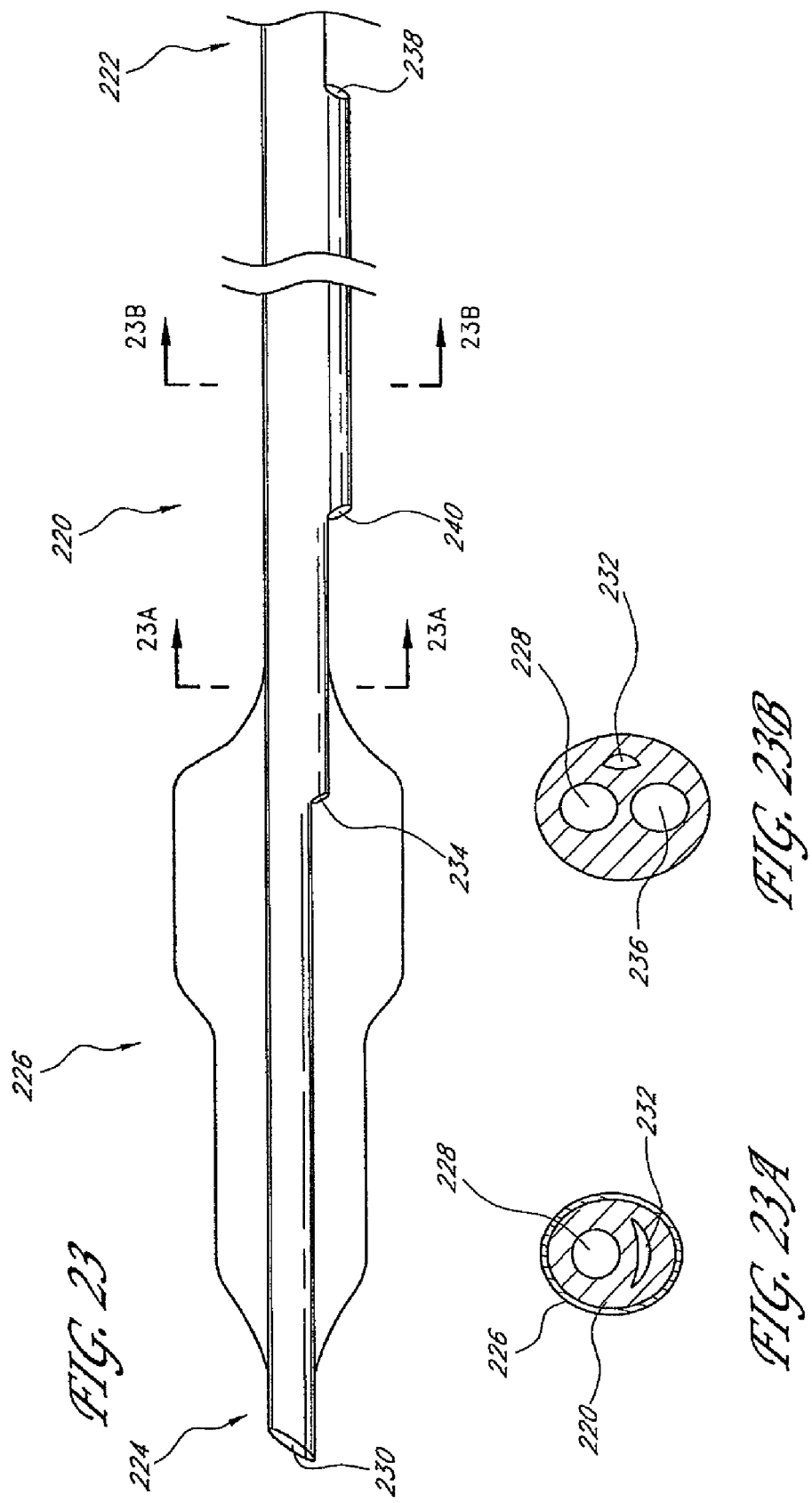

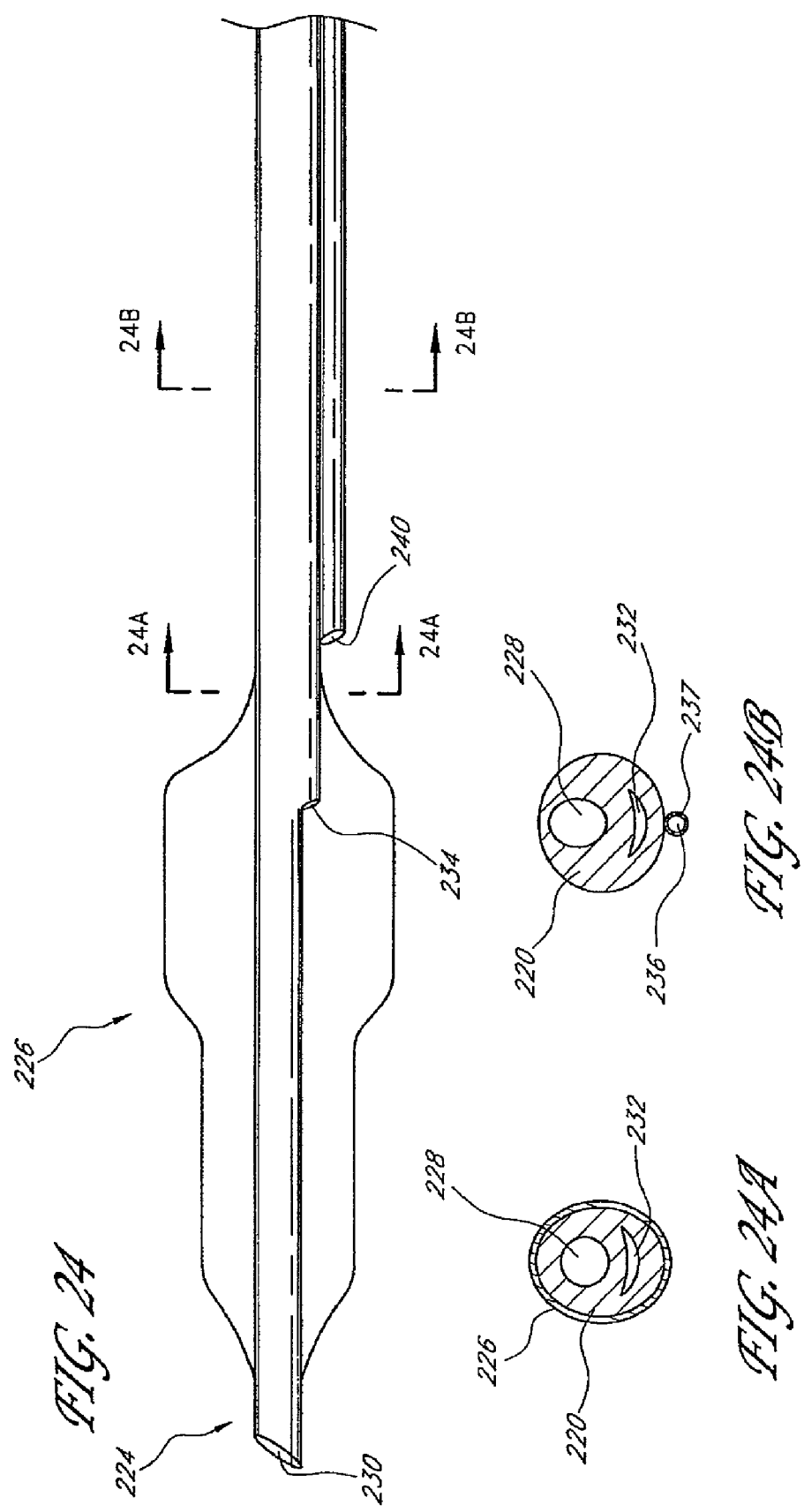

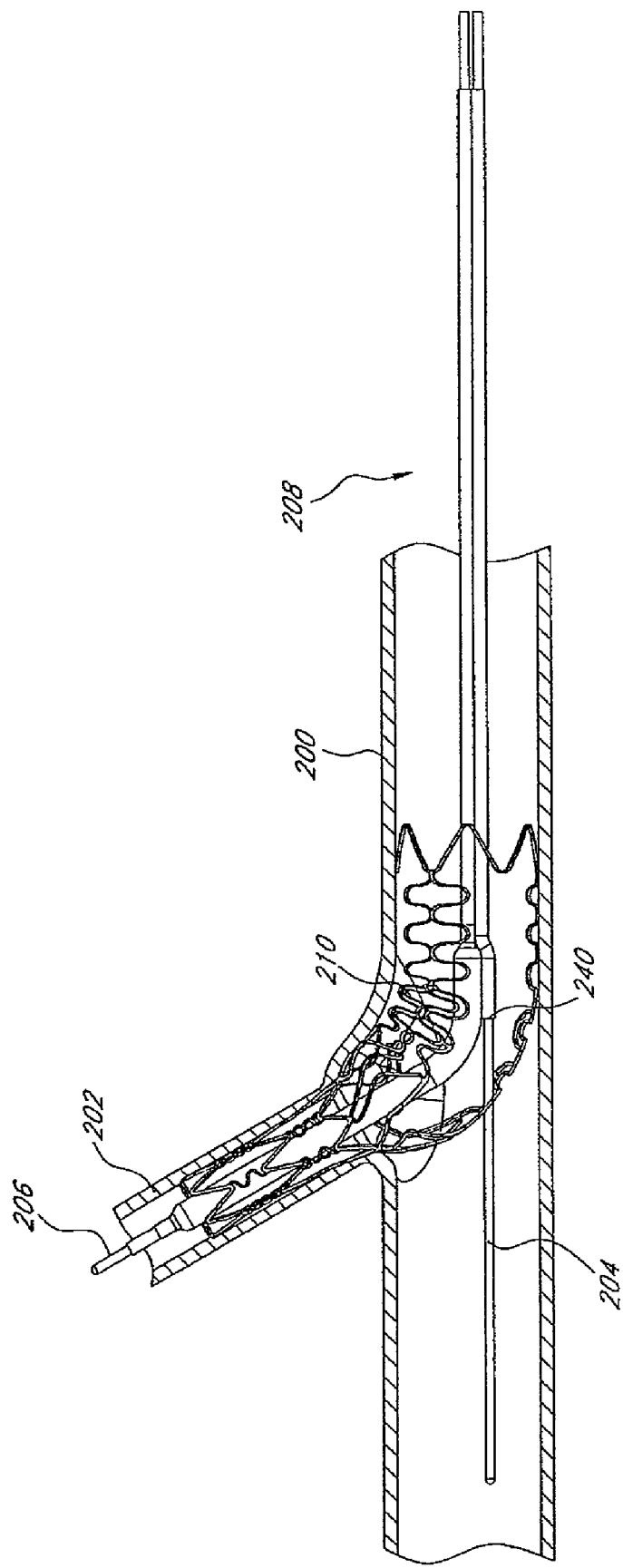

KIT FOR TREATING VASCULAR BIFURCATIONS

CROSS-REFERENCE TO RELATED APPLICATIONS

This application is a Continuation of U.S. patent application Ser. No. 10/584,968 filed Jun. 30, 2006, which is a U.S. National Phase under 35 U.S.C. §371 of International Application PCT/US2005/036987, filed Oct. 13, 2005 and published in English on Apr. 27, 2006 and is a Continuation of U.S. patent application Ser. No. 11/249,138, filed on Oct. 12, 2005, which is a Continuation-In-Part of U.S. patent application Ser. No. 11/190,514 filed on Jul. 27, 2005 which is a Continuation-in-Part of U.S. patent application Ser. No. 11/076,448, now U.S. Pat. No. 7,731,747, filed on Mar. 9, 2005, which is a Continuation-in-Part of co-pending U.S. patent application Ser. No. 10/807,643, now U.S. Pat. No. 7,481,834, filed on Mar. 23, 2004, which claims the benefit of priority of U.S. Provisional Application No. 60/463,075, filed on Apr. 14, 2003, the full disclosures of which are incorporated in their entireties herein by reference. U.S. patent application Ser. No. 11/249,138 also is a Continuation-In-Part of U.S. patent application Ser. No. 10/965,230, now U.S. Pat. No. 7,717,953, filed on Oct. 13, 2004, and the full disclosure of which is incorporated by reference in its entirety herein.

BACKGROUND OF THE INVENTION

1. Field of the Invention

Embodiments of the present invention relate generally to medical devices and methods. More particularly, embodiments of the present invention relate to the structure and deployment of a prosthesis having a stent or other support structure and at least one, and in some implementations at least two fronds for deployment at a branching point in the vasculature or elsewhere.

Maintaining the patency of body lumens is of interest in the treatment of a variety of diseases. Of particular interest to the present invention are the transluminal approaches to the treatment of body lumens. More particularly, the percutaneous treatment of atherosclerotic disease involving the coronary and peripheral arterial systems. Currently, percutaneous coronary interventions (PCI) often involve a combination of balloon dilation of a coronary stenosis (i.e. a narrowing or blockage of the artery) followed by the placement of an endovascular prosthesis commonly referred to as a stent.

A major limitation of PCI/stent procedures is restenosis, i.e., the re-narrowing of a blockage after successful intervention typically occurring in the initial three to six months post treatment. The recent introduction of drug eluting stents (DES) has dramatically reduced the incidence of restenosis in coronary vascular applications and offers promise in peripheral stents, venous grafts, arterial and prosthetic grafts, as well as A-V fistulae. In addition to vascular applications, stents are being employed in treatment of other body lumens including the gastrointestinal systems (esophagus, large and small intestines, biliary system and pancreatic ducts) and the genital-urinary system (ureter, urethra, fallopian tubes, vas deferens).

Treatment of lesions in and around branch points generally referred to as bifurcated vessels, is a developing area for stent applications, particularly, since at least about 5%-10% of all coronary lesions involve bifurcations. However, while quite successful in treating arterial blockages and other conditions, current stent designs are challenged when used at a bifurcation in the blood vessel or other body lumen. Presently, many different strategies are employed to treat bifurcation lesions with currently available stents all of which have major limitations.

One common approach is to place a conventional stent in the main or larger body lumen over the origin of the side branch. After removal of the stent delivery balloon, a second wire is introduced through a cell in the wall of the deployed stent and into the side branch. A balloon is then introduced into the side branch and inflated to enlarge the side-cell of the main vessel stent. This approach can work well when the side branch is relatively free of disease, although it is associated with increased rates of abrupt closure due to plaque shift and dissection as well as increased rates of late restenosis.

Another commonly employed strategy is the 'kissing balloon' technique in which separate balloons are positioned in the main and side branch vessels and simultaneously inflated to deliver separate stents simultaneously. This technique is thought to prevent plaque shift.

Other two-stent approaches including Culotte, T-Stent and Crush Stent techniques have been employed as well. When employing a T-Stent approach, the operator deploys a stent in the side branch followed by placement of a main vessel stent. This approach is limited by anatomic variation (angle between main and side branch) and inaccuracy in stent positioning, which together can cause inadequate stent coverage of the side branch origin commonly referred to as the ostium or Os. More recently, the Crush approach has been introduced in which the side-vessel stent is deployed across the Os with portions in both the main and side branch vessels. The main vessel stent is then delivered across the origin of the side branch and deployed, which results in crushing a portion of the side branch stent between the main vessel stent and the wall of the main vessel. Following main-vessel stent deployment, it is difficult and frequently not possible to re-enter the side branch after crush stenting. Unproven long-term results coupled with concern regarding the inability to re-enter the side branch, malposition of the stents against the arterial wall and the impact of three layers of stent (which may be drug eluting) opposed against the main vessel wall has limited the adoption of this approach.

These limitations have led to the development of stents specifically designed to treat bifurcated lesions. One approach employs a stent design with a side opening for the branch vessel which is mounted on a specialized balloon delivery system. The specialized balloon delivery system accommodates wires for both the main and side branch vessels. The system is tracked over both wires which provides a means to axially and radially align the stent/stent delivery system. The specialized main vessel stent is then deployed and the stent delivery system removed while maintaining wire position in both the main and side branch vessels. The side branch is then addressed using the kissing balloon technique or by delivering an additional stent to the side branch. Though this approach has many theoretical advantages, it is limited by difficulties in tracking the delivery system over two wires (See, e.g., U.S. Pat. Nos. 6,325,826 and 6,210,429 to Vardi et al.).

Notwithstanding the foregoing efforts, there remains a need for improved devices as well as systems and methods for delivering devices, to treat body lumens at or near the location of an Os between a main body lumen and a side branch lumen, typically in the vasculature, and more particularly in the arterial vasculature. It would be further desirable if such systems and methods could achieve both sufficient radial support as well as adequate surface area coverage in the region of the Os and that the prostheses in the side branches be well-anchored at or near the Os.

2. Description of the Related Art

Stent structures intended for treating bifurcated lesions are described in U.S. Pat. Nos. 6,599,316; 6,596,020; 6,325,826; and 6,210,429. Other stents and prostheses of interest are described in the following U.S. Pat. Nos. 4,994,071; 5,102, 417; 5,342,387; 5,507,769; 5,575,817; 5,607,444; 5,609,627; 5,613,980; 5,669,924; 5,669,932; 5,720,735; 5,741,325; 5,749,825; 5,755,734; 5,755,735; 5,824,052; 5,827,320; 5,855,598; 5,860,998; 5,868,777; 5,893,887; 5,897,588; 5,906,640; 5,906,641; 5,967,971; 6,017,363; 6,033,434; 6,033,435; 6,048,361; 6,051,020; 6,056,775; 6,090,133; 6,096,073; 6,099,497; 6,099,560; 6,129,738; 6,165,195; 6,221,080; 6,221,098; 6,254,593; 6,258,116; 6,264,682; 6,346,089; 6,361,544; 6,383,213; 6,387,120; 6,409,750; 6,428,567; 6,436,104; 6,436,134; 6,440,165; 6,482,211; 6,508,836; 6,579,312; and 6,582,394.

SUMMARY OF THE INVENTION

There is provided in accordance with one aspect of the present invention, a prosthesis for placement at an ostium or Os opening from a main body lumen to a branch body lumen. The prosthesis comprises a radially expansible branch vessel support, configured to be deployed in at least a portion of the branch body lumen. At least one, and in some implementations a plurality of fronds extend axially from the support. A radially expansible connector, spaced axially apart from the branch vessel support is provided for connecting at least two points on the frond, and optionally at least two or all of the fronds in a multi frond implementation of the invention.

In accordance with a further aspect of the present invention, there is provided a method for treating a bifurcation between a main lumen and a branch lumen. The method comprises the steps of providing a radially expandable scaffold, having a proximal end, a distal end, a support structure on the distal end, a circumferential link on the proximal end and at least two fronds extending axially between the support structure and the circumferential link. The scaffold is transluminally navigated to a treatment site, and deployed at the site such that the support is in the branch lumen and the circumferential link is in the main lumen.

The method may additionally comprise a step of positioning an inflatable balloon in the main lumen, and deforming the circumferential link such that it conforms to at least a portion of the wall of the main lumen. The method may additionally comprise the step of deploying a stent in the main lumen, to trap fronds between the main vessel stent and the adjacent vessel wall.

In accordance with a further aspect of the present invention, there is provided a prosthesis for placement at an opening from a main body lumen to a branch body lumen. The prosthesis comprises a radially expansible support, the support configured to be deployed in at least a portion of the branch body lumen. A plurality of fronds extend axially from the support, and at least one circumferential link connects at least a first and a second frond, the circumferential link spaced axially apart from the support. Preferably, the circumferential link connects each of the plurality of fronds. At least a portion of the prosthesis may be provided with a drug coating. The drug coating may be a drug eluting coating, and may be configured to exhibit at least one of a controlled drug release rate, a constant release rate, bi-modal drug release rate, or a controlled concentration of drug proximate a target vessel wall.

There is provided in accordance with one aspect of the present invention, a prosthesis and deployment system assembly. The assembly comprises an elongate flexible catheter body, having a balloon thereon. The balloon has an inflated profile with a first section having a first diameter, a second section having a second diameter, and a balloon transition in-between the first and second sections. A prosthesis is carried by the balloon. The prosthesis has a wall, having a first wall pattern adjacent the first section of the balloon, and a second wall pattern adjacent the balloon transition. In one embodiment, the prosthesis has a third wall pattern adjacent the second section of the balloon.

There is provided in accordance with another aspect of the present invention, a prosthesis and deployment catheter system for treating an opening from a main body lumen to a branch body lumen. The prosthesis comprises a radially expansible support, the support configured to be deployed in at least a portion of the branch body lumen. A plurality of fronds extends axially from an end of the support, and are configured to be positioned across the Os and into the main body lumen. At least one circumferential link connects at least a first and a second frond, the circumferential link spaced axially apart from the support.

The prosthesis is mounted on a balloon catheter, such that the radially expansible support is carried by a first portion of a balloon that is inflatable to a first diameter, and the circumferential link is carried by a second portion of a balloon that is inflatable to a second diameter, that is larger than the first diameter.

The circumferential link may connect each of the plurality of fronds. Preferably, the plurality of fronds includes at least three fronds. Each frond may comprise a resilient metal.

At least a portion of the resiliently expansible support may comprise a drug coating, and at least a portion of the fronds and the circumferential link are without a drug coating. The drug coating may be a drug eluting coating, and may be configured to produce at least one of a controlled drug delivery rate, a constant drug delivery rate, bimodal drug release rate, or a controlled concentration of drug proximate a target vessel wall. The drug may be configured to reduce an incidence or amount of restenosis.

In accordance with further aspect of the present invention, there is provided a method of treating a patient. The method comprises the steps of providing a catheter having a balloon with at least a first section having a relatively small inflated diameter and a second section having a relatively larger inflated diameter. The balloon is positioned across the opening of a branch vessel from a main vessel. The balloon is thereafter inflated such that the first section is inflated at least partially within the branch vessel and the second section is inflated at least partially within the main vessel.

The providing a catheter step preferably comprises providing a catheter having an implantable prosthesis mounted on the balloon. The prosthesis may have a first zone carried by a first section of the balloon and a second zone carried by a second section of the balloon. The prosthesis may additionally have a transition zone positioned between the first zone and the second zone.

In accordance with a further aspect of the present invention, there is provided a method for treating a bifurcation between a main lumen and a branch lumen. The method comprises the steps of providing a radially expandable prosthesis, having a proximal end, a distal end, a support structure on the distal end, a circumferential link on the proximal end, and at least two fronds extending axially between the support structure and the circumferential link. The prosthesis is transluminally navigated to the treatment site. The prosthesis is deployed at the site such that the support is expanded in the branch lumen by a first diameter section of a first deployment balloon, and the circumferential link is expanded in the main lumen by a second diameter section of the deployment balloon.

The method may additionally comprise the step of positioning a second inflatable balloon in the main lumen, and deforming at least one frond such that it conforms to at least a portion of the wall of the main lumen. The method may comprise the additional step of deploying a stent in the main lumen.

Further features and advantages of the present invention will become apparent from the detailed description of preferred embodiments which follows, when considered together with the attached drawings and claims.

BRIEF DESCRIPTION OF THE DRAWINGS

FIGS. 2A-2E are lateral views showing embodiments of a stent having fronds in a rolled out configuration. FIG. 2A shows an embodiment having serpentine-shaped fronds, FIG. 2B shows an embodiment having filament shaped fronds, while FIG. 2C shows an embodiment having filament shaped fronds with alternating shortened fronds. FIGS. 2D and 2E illustrate a nested transition zone configuration with two different stent wall patterns.

FIG. 5A shows pre-deployment, the balloon uninflated; FIG. 5B shows deployment, with the balloon inflated; and FIG. 5C post-deployment, the balloon now deflated.

FIG. 6A shows the balloon in an unexpanded state; and FIG. 6B shows the balloon in an expanded state, with the cuff expanded radially and shrunken axially.

FIGS. 13A-13C illustrate side wall patterns for three main vessel stents useful in combination with the prosthesis of the present invention.

FIG. 21 is a third step in a deployment sequence, in which a prosthesis has been expanded utilizing a stepped balloon in accordance with the present invention.

FIG. 22 is a fourth step in a deployment sequence, in which the stepped balloon has been removed following deployment of the prosthesis across the Os.

FIG. 23 is a side elevational schematic view of a distal portion of a catheter in accordance with the present invention.

FIG. 23A is a cross sectional view taken along the lines 23A-23A in FIG. 23.

FIG. 23B is a cross sectional view taken along the lines 23B-23B in FIG. 23.

FIG. 24 is a side elevational view as in FIG. 23, with a modified catheter in accordance with the present invention.

FIG. 24A is a cross sectional view taken along the line 24A-24A of FIG. 24.

FIG. 24B is a cross sectional view taken along the line 24B-24B in FIG. 24.

FIG. 27 is a schematic view as in FIG. 25, with a modified two guidewire catheter in accordance with the present invention.

DETAILED DESCRIPTION OF THE PREFERRED EMBODIMENT

Figure 1:
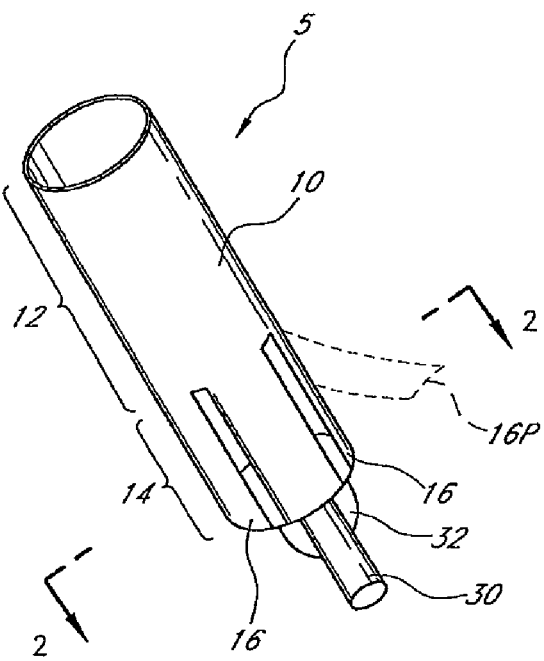
FIG. 1 is a schematic illustration of a prosthesis constructed in accordance with the principles of the present invention.

Embodiments of the present invention provide improved prostheses and delivery systems for their placement within a body lumen, particularly within a bifurcated body lumen and more particularly at an Os opening from a main body lumen to a branch body lumen. The prostheses and delivery systems will be principally useful in the vasculature, most typically the arterial vasculature, including the coronary, carotid and peripheral vasculature; vascular grafts including arterial, venous, and prosthetic grafts such as a bifurcated abdominal aortic aneurysm graft, and A-V fistulae. In addition to vascular applications, embodiments of the present invention can also be configured to be used in the treatment of other body lumens including those in the gastrointestinal systems (e.g., esophagus, large and small intestines, biliary system and pancreatic ducts) and the genital-urinary system (e.g., ureter, urethra, fallopian tubes, vas deferens), and the like.

The prosthesis in accordance with the present invention generally comprises three basic components: a stent or other support, at least one frond extending from the support, and a transition zone between the support and the frond. These components may be integrally formed such as by molding, or by laser or other cutting from tubular stock, or may be separately formed and secured together.

The term "fronds" as used herein will refer to any of a variety of structures including anchors, filaments, petals or other independently multiaxially deflectable elements extending from the stent or other support structure, to engage an adjacent main vessel stent or other associated structure. These fronds can expandably conform to and at least partially circumscribe the wall of the main body vessel to selectively and stably position the prosthesis within the side branch lumen and/or optimize wall coverage in the vicinity of the ostium. Further description of exemplary frond structures and prostheses is found in co-pending application Ser. No. 10/807,643, the full disclosure of which has previously been incorporated herein by reference. Various embodiments of the present invention provide means for capturing or otherwise radially constraining the fronds during advancement of the prosthesis through the vasculature (or other body lumen) to a target site and then releasing the fronds at the desired deployment site.

The prostheses of the present invention are particularly advantageous since they permit substantially complete coverage of the wall of the branch body lumen up to and including the lumen ostium or Os. Additionally, the prostheses have integrated fronds which expandably conform to and at least partially circumscribe the wall of the main body vessel to selectively and stably link the prosthesis to the main vessel stent. The fronds may be fully expanded to open the luminal passage through the main branch lumen. Such complete opening is an advantage since it provides patency through the main branch lumen. Moreover, the open main vessel lumen permits optional placement of a second prosthesis within the main branch lumen using conventional techniques.

In a first aspect of the present invention, a prosthesis comprises a radially expansible support and at least one or often two or more fronds extending axially from an end of the support. The fronds are adapted to extend around, or "expandably circumscribe" a portion of, usually at least one-half of the circumference of the main vessel wall at or near the Os when the support is implanted in the branch lumen with the fronds extending into the main lumen. By "expandably circumscribe," it is meant that the fronds will extend into the main body lumen after initial placement of the support within the branch body lumen. The fronds will be adapted to then be partially or fully radially expanded, typically by expansion of a balloon or other expandable structure therein, so that the fronds deform outwardly and conform to the interior surface of the main lumen.

The fronds will usually extend axially within the main vessel lumen for some distance after complete deployment. In certain embodiments, the contact between the fronds and the main vessel wall will usually extend both circumferentially (typically at least one frond may cover an arc equal to one-half or more of the circumference of the main vessel) and axially.

Deformation of the fronds to conform to at least a portion of the wall of the main body lumen provides a generally continuous coverage of the Os from the side branch lumen to the main vessel lumen. Further and/or complete expansion of the fronds within the main body lumen may press the fronds firmly against the main body lumen wall and open up the fronds so that they do not obstruct flow through the main body lumen, while maintaining patency and coverage of the side branch and os.

Usually, the prosthesis will include at least two or three fronds extending axially from the end of the support. The prosthesis could include four, five, or even a greater number of fronds, but the use of three such fronds is presently contemplated for a coronary artery embodiment. The fronds will have an initial length (i.e., prior to radial expansion of the prosthesis) which is at least about 1.5 times the width of the prosthesis prior to expansion, typically at least about 2 times the width, more typically at least about 5 times the width, and often about 7 times the width or greater. The lengths will typically be at least about 2 mm, preferably at least about 3 mm, and more preferably at least about 6 mm. The frond length may also be considered relative to the diameter of the corresponding main vessel. For example, a prosthesis configured for use in a branch vessel from a main vessel having a 3 mm lumen will preferably have a frond length of at least about 7 mm and in some embodiments at least about 9 mm.

Embodiments of the present invention incorporating only a single frond are also contemplated. The single frond may extend axially from the branch vessel support as has been described in connection with multi frond embodiments. Alternatively, the single frond (or two or three or more fronds) may extend in a helical or spiral pattern, such that it wraps in a helical winding about the longitudinal axis extending through the branch vessel support.

The fronds may have a fixed width or a width which is expandable to accommodate the expansion of the support, and the fronds may be "hinged" at their point of connection to the support to permit freedom to adapt to the geometry of the main vessel lumen as the prosthesis is expanded. As used herein, "hinged" does not refer to a specific structure such as a conventional hinge, but rather to any combination of structures, materials and dimensions that permit multiaxial flexibility of the frond relative to the support so that the frond can bend in any direction and/or rotate about any axis to conform to the ablumenal surface of the expanded main vessel stent under normal use conditions. It is also possible that the fronds could be attached at a single point to the support, thus reducing the need for such expandability. The fronds may be congruent, i.e., have identical geometries and dimensions, or may have different geometries and/or dimensions. In particular, in some instances, it may be desirable to provide fronds having different lengths and/or different widths.

In another aspect of the invention, at least one of the of fronds has a loop or filament shape and includes a first expandable strut configured to be positioned at the Os in an expanded state and provide radial support to an interior portion of the main body lumen. The fronds can be fabricated from flexible metal wire, molded, laser cut or otherwise formed from tube stock in accordance with known techniques. The strut can be configured to be substantially triangular in the expanded state. Also, at least one of the fronds may be configured to be expandably deployed proximate a vessel wall by an expandable device such as an expandable balloon catheter.

In another aspect of the invention, a prosthesis delivery system comprises a delivery catheter having an expandable member and a prosthesis carried over the expandable member. The prosthesis has a radially expandable support such as a tubular stent and at least two fronds extending axially from the support. The system also includes a retainer for capturing the fronds to prevent them from divaricating from the expandable member as the catheter is advanced through a patient's vasculature. "Divarication" as used herein means the separation or branching of the fronds away from the delivery catheter. Various embodiments of the capture means prevent divarication by constraining and/or imparting sufficient hoop strength to the fronds to prevent them from branching from the expandable member during catheter advancement in the vasculature.

In one embodiment, the capturing means comprises a portion of the expandable member that is folded over the fronds where the folds protrude through axial gaps between adjacent fronds. In another embodiment, the capturing means comprises a cuff that extends over at least a portion of the fronds to hold them during catheter advancement. The cuff can be positioned at the proximal end of the prosthesis and can be removed by expansion of the expandable member to either plastically or elastically deform the cuff, break the cuff, or reduce the cuff in length axially as the cuff expands circumferentially. The cuff is then withdrawn from the target vessel. In yet another embodiment, the capturing means can comprise a tether which ties together the fronds. The tether can be configured to be detached from the fronds prior to expansion of the expandable member. In alternative embodiments, the tether can be configured to break or release upon expansion of the expandable member so as to release the fronds.

In an exemplary deployment protocol using the prosthesis delivery system, the delivery catheter is advanced to position the prosthesis at a target location in a body lumen. During advancement, at least a portion of the fronds are radially constrained to prevent divarication of the fronds from the delivery catheter. When the target location is reached, the radial constraint is released and the prosthesis is deployed within the lumen.

In various embodiments, the release of the fronds and expansion of the prosthesis can occur simultaneously or alternatively, the radial constraint can be released prior to, during, or after expanding/deploying the prosthesis. In embodiments where the radial constraint comprises balloon folds covering the fronds or a cuff or tether, the constraint can be released as the balloon is inflated. In alternative embodiments using a cuff or tether, the cuff/tether can be withdrawn from the fronds prior to expansion of the support.

Embodiments of the above protocol can be used to deploy the prosthesis across the Os of a branch body lumen and trailing into the main body lumen. In such applications, the prosthesis can be positioned so that the stent lies within the branch body and at least two fronds extend into the main body lumen. The fronds are then circumferentially deformed to conform to at least a portion of the main vessel wall to define a main vessel passage through the fronds. At least two and preferably at least three fronds extend into the main body lumen.

Radiopaque or other medical imaging visible markers can be placed on the prostheses and/or delivery balloon at desired locations. In particular, it may be desirable to provide radiopaque markers at or near the location on the prosthesis where the stent is joined to the fronds. Such markers will allow a transition region of the prosthesis between the stent and the fronds to be properly located near the Os prior to stent expansion. The radiopaque or other markers for locating the transition region on the prosthesis can also be positioned at a corresponding location on a balloon catheter or other delivery catheter. Accordingly, in one embodiment of the deployment protocol, positioning the prosthesis can include aligning a visible marker on at least one of the prosthesis, on the radial constraint, and the delivery balloon with the Os.

In various embodiments for deploying the prosthesis, the support is expanded with a balloon catheter expanded within the support. In some instances, the support and the fronds may be expanded and deformed using the same balloon, e.g., the balloon is first used to expand the support, partially withdrawn, and then advanced transversely through the fronds where it is expanded for a second time to deform the fronds. A balloon the length of the support (shorter than the total prosthesis length) can be used to expand the support, and then be proximally retracted and expanded in the fronds. Alternatively, separate balloon catheters may be employed for expanding the support within the side branch and for deforming the fronds against the wall of the main body lumen.

The fronds may expand radially in parallel with the support section of the prosthesis. Then, in a second step, the fronds may be folded out of plane as the main vessel stent or balloon is deployed. Deformation of the fronds at least partially within the main body lumen provides a generally continuous coverage of the Os from the side body lumen to the main body lumen. Further and/or complete expansion of the fronds within the main body lumen may press the fronds firmly against the main body lumen wall and open up the fronds so that they do not obstruct flow through the main body lumen.

The prosthesis may include at least one and in some embodiments at least three fronds extending axially from the end of the support. The fronds will have an initial length (i.e., prior to radial expansion of the stent) which is at least about 1.5 times the cross sectional width of the support prior to expansion, typically at least about 2 times the width, more typically at least about 5 times the width, and often about 7 times the width or greater. The lengths of the fronds will typically be at least about 2 mm, preferably at least about 3 mm, and more preferably at least about 6 mm, as discussed elsewhere herein additional detail. The fronds will usually have a width which is expandable to accommodate the expansion of the stent, and the fronds may be "hinged" or otherwise flexibly connected at their point of connection to the prosthesis to permit freedom to adapt to the geometry of the main vessel lumen as the stent is expanded. It is also possible that the fronds could be attached to the single point to the prosthesis, thus reducing the need for such expandability. Fronds may be optimized for particular bifurcation angles and orientations, such as by making the fronds for positioning closer to the "toe" of the bifurcation longer than the fronds for positioning closer to the carina or "heel" of the bifurcation.

Figure 2:
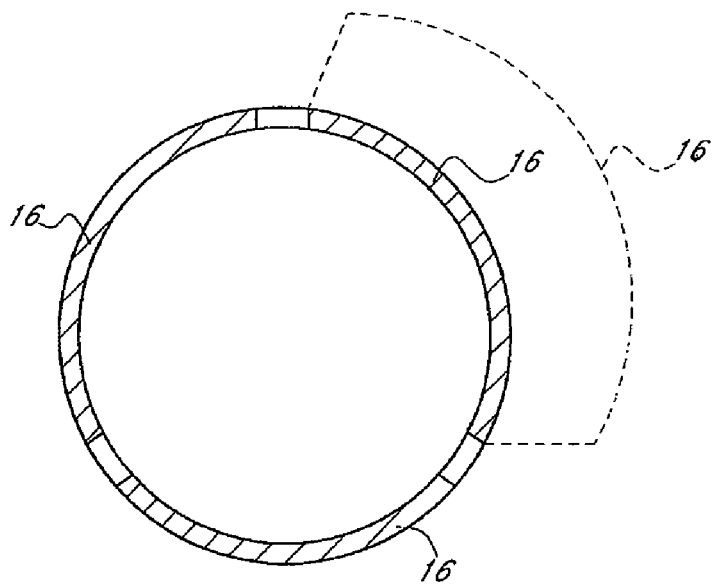
FIG. 2 is a cross-sectional view taken along line 2-2 of FIG. 1.

Referring now to FIGS. 1 and 2, an embodiment of a prosthesis and delivery system 5 of the present invention for the delivery of a prosthesis to a bifurcated vessel can include a prosthesis 10 and a delivery catheter 30. Prosthesis 10 can include at least a radially expansible support section 12 and a frond section 14 with one or more fronds 16. The base of the fronds resides in a transition zone, described below. In various embodiments, the frond section 14 includes at least two axially extending fronds 16, with three being illustrated.

Balloon catheters suitable for use with the prosthesis of the present invention are well understood in the art, and will not be described in great detail herein. In general, a catheter suitable for use for deployment of the prosthesis of the present invention will comprise an elongate tubular body extending between a proximal end and a distal end. The length of the (catheter) tubular body depends upon the desired application.

For example, lengths in the area of from about 120 cm to about 140 cm are typical for use in a percutaneous transluminal coronary application intended for accessing the coronary arteries via the femoral artery. Other anatomic spaces including renal, iliac, femoral and other peripheral applications may call for a different catheter shaft length and balloon dimensions, depending upon the vascular access site as will be apparent to those of skill in the art.

The catheter shaft is provided with at least one central lumen, for an inflation media for inflating an inflatable balloon carried by the distal end of the catheter shaft. In an over the wire embodiment, the catheter shaft is additionally provided with a guidewire lumen extending throughout the entire length thereof. Alternatively, the prosthesis of the present invention may be deployed from a rapid exchange or monorail system, in which a proximal access port for the guidewire lumen is provided along the side wall of the catheter shaft distally of the proximal manifold, such as within about the distal most 20 cm of the length of the balloon catheter, or from a convertible system as is known in the art.

The catheter shaft for most applications will be provided with an approximately circular cross sectional configuration, having an external diameter within the range of from about 0.025 inches to about 0.065 inches depending upon, among other things, whether the target bifurcation is in the coronary or peripheral vasculature. Systems may have diameters in excess of about 0.25 inches and up to as much as about 0.35 inches in certain applications. Diameters of from about 1.5 mm up to as large as about 7 mm are contemplated for coronary indications. Additional features and characteristics may be included in the deployment catheter design, such frond retention structures discussed below, depending upon the desired functionality and clinical performance as will be apparent to those of skill in the art.

The radially expansible support section 12 will typically be expandable by an expansion device such as a balloon catheter, but alternatively it can be self expandable. The support section 12 may be formed using any of a variety of conventional patterns and fabrication techniques as are well-described in the prior art.

Depending upon the desired clinical result, the support section or stent 12 may be provided with sufficient radial force to maintain patency of a diseased portion of the branch lumen. This may be desirable in an instance were vascular disease is present in the branch vessel. Alternatively, the support section 12 may be simply called upon to retain the fronds in position during deployment of the primary vascular implant. In this instance, a greater degree of flexibility is afforded for the configuration of the wall pattern of the support section 12. For example, support section 12 may comprise a helical spiral, such as a Nitinol or other memory metal which is deployable from an elongate deployment lumen, but which reverts to its helical configuration within the branch vessel. Alternative self expandable structures may be used such as a zig-zag series of struts, connected by a plurality of proximal apexes and a plurality of distal apexes and rolled into a cylindrical configuration. This configuration is well understood in the vascular graft and stent arts, as a common foundation for a self expandable tubular support.

In one implementation of the present invention, the prosthesis comprises an overall length of about 19 mm, which is made up of a stent having a length of about 9.6 mm, a targeted expanded diameter of about 2.5 mm and a plurality of fronds having a length of about 9.3 mm.

The fronds will usually have a width measured in a circumferential direction in the transition zone which is expandable from a first, delivery width to a second, implanted width to accommodate the expansion of the support, while maintaining optimal wall coverage by the fronds. Thus, although each of the fronds may comprise a single axially extending ribbon or strut, fronds are preferably configured to permit expansion in a circumferential direction at least in the transition zone with radial expansion of the support structure. For this purpose, each frond may comprise a single axially extending element, but often comprises at least two axially extending elements 66A and 66D, and optimally three or more axially extending elements, which can be spaced laterally apart from each other upon radial expansion of the prosthesis, to increase in width in the circumferential direction. The increased width referred to herein will differ on a given frond depending upon where along the length of the frond the measurement is taken. Fronds of the type illustrated herein will increase in width the most at the end attached to the support, and the least (or none) at the free apex end as will be appreciated by those of skill in the art. Circumferentially expanding at least the base of the frond enables optimal wall coverage in the vicinity of the ostium, following deployment of the prosthesis at the treatment site. In addition, multiple elements results in a greater surface area as a biological substrate or increased delivery of pharma agents.

In the illustrated embodiments, each of the fronds 16 has an equal width with the other fronds 16. However, a first frond or set of fronds may be provided with a first width (measured in a circumferential direction) and a second frond or set of fronds may be provided with a second, different width. Dissimilar width fronds may be provided, such as alternating fronds having a first width with fronds having a second width.

In each of the foregoing constructions, radially symmetry may exist such that the rotational orientation of the prosthesis upon deployment is unimportant. This can simplify the deployment procedure for the prosthesis. Alternatively, prostheses of the present invention exhibiting radial asymmetry may be provided, depending upon the desired clinical performance. For example, a first frond or set of fronds may be centered around 0° while a second frond or set of fronds is centered around 180° when the prosthesis is viewed in a proximal end elevational view. This may be useful if the fronds are intended to extend around first and second opposing sides of the main vessel stent. Asymmetry in the length of the fronds may also be accomplished, such as by providing fronds at a 0° location with a first length, and fronds at 180° location with a second length. As will become apparent below, such as by reference to FIG. 9A, certain fronds in the deployed prosthesis will extend along an arc which aligns with the axis of the branch vessel at a distal end, and aligns with the axis of the main vessel at a proximal end. The proximal ends of fronds of equal length will be positioned axially apart along the main vessel lumen. If it is desired that the proximal ends of any of the fronds align within the same transverse cross section through the main vessel lumen, or achieve another desired configuration, fronds of different axial lengths will be required as will become apparent to those of skill in the art.

Certain additional features may be desirable in the prosthesis and/or deployment system of the present invention, in an embodiment in which the rotational orientation of the prosthesis is important. For example, the catheter shaft of the deployment system preferably exhibits sufficient torque transmission that rotation of the proximal end of the catheter by the clinician produces an approximately equal rotation at the distal end of the catheter. The torque transmission characteristics of the catheter shaft may be optimized using any of a variety of structures which are known in the art. For example, a helical winding may be incorporated into the wall of the catheter shaft, using any of a variety of embedding techniques, or by winding a filament around an inner tube and positioning an outer tube over the winding, subsequently heat shrinking or otherwise fusing the tubes together. Bi-directional torque transmission characteristics can be optimized by providing a first winding in a first (e.g. clockwise) direction, and also a second winding in a second (e.g. counter clockwise) direction. The winding may comprise any of a variety of materials, such as metal ribbon, or a polymeric ribbon. Various tubular meshes and braids may also be incorporated into the catheter wall.

In addition, the rotational orientation of the prosthesis is preferably observable fluoroscopically, or using other medical imaging techniques. For this purpose, one or more markers is preferably provided on either the prosthesis, the restraint or the deployment catheter, to enable visualization of the rotational orientation.

The sum of the widths measured in the circumferential direction of the fronds 16 when the prosthesis is in either the first, transluminal navigation configuration or the second, deployed configuration will preferably add up to no more than one circumference of the stent portion of the prosthesis. In this manner, the width of the frond 16s at the level of attachment may be maximized, but without requiring overlap especially in the first configuration. The width of each frond 16 may generally increase upon deployment of the prosthesis to at least about 125%, often at least about 200%, and in some instances up to about 300% or more of its initial width, at least at the distal end (base) of the frond 16. The proximal free end of each frond 16 may not increase in circumferential width at all, with a resulting gradation of increase in circumferential width throughout the axial length from the proximal end to the distal end of the frond. While portions of the fronds may expand as described above, in alternate constructions, the fronds may have a width that remains constant or substantially constant throughout the length of the frond as the prosthesis is deployed.

The fronds may be "hinged" as has been described at their point of connection to the support to permit freedom to adapt to the geometry of the main vessel lumen as the prosthesis is expanded. It is also possible that each frond is attached at a single point to the support, thus reducing the need for such expandability at the junction between the frond and the support. The fronds may be congruent, i.e., have identical geometries and dimensions, or may have different geometries and/ or dimensions. Again, further description of the fronds may be found in co-pending application Ser. No. 10/807,643.

Fronds 16, will usually extend axially from the support section 12, as illustrated, but in some circumstances the fronds can be configured to extend helically, spirally, in a serpentine pattern, or other configurations as long as the configuration permits placement of the stent in a vessel such that the fronds extend across the Os. It is desirable, however, that the individual fronds be radially separable so that they can be independently, displaced, folded, bent, rotated about their longitudinal axes, and otherwise positioned within the main body lumen after the support section 12 has been expanded within the branch body lumen. In the schematic embodiment of FIG. 1, the fronds 16 may be independently folded out in a "petal-like" configuration, forming petals 16p, as generally shown in broken line for one of the fronds in FIGS. 1 and 2.

Figure 1A:
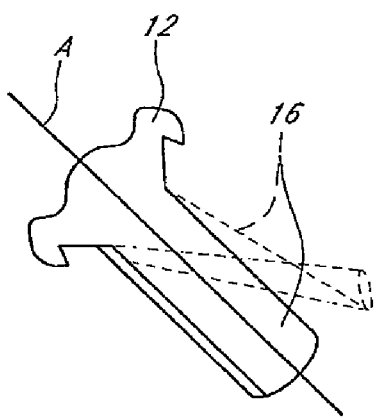
FIG. 1A is a detailed view of the fronds of the prosthesis of FIG. 1, shown with the fronds deployed in broken line.

In preferred embodiments, fronds 16 will be attached to the support section 12 such that they can both bend and rotate relative to an axis A thereof, as shown in broken line in FIG. 1A. Bending can occur radially outwardly and rotation or twisting can occur about the axis A or a parallel to the axis A as the fronds are bent outwardly. Such freedom of motion can be provided by single point attachment joints as well as two point attachments or three or more point attachments.

Figure 2A:
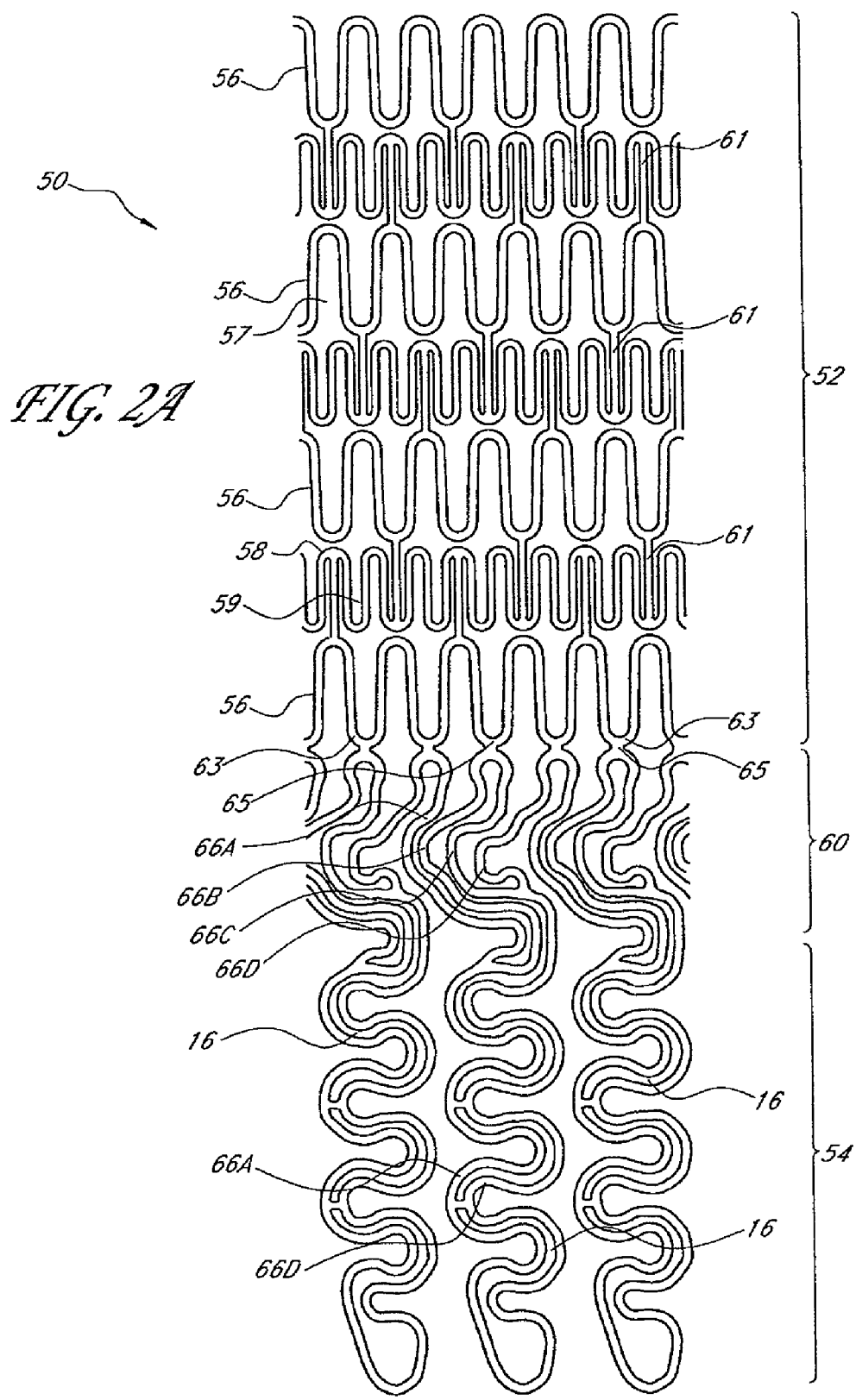

Referring now to FIG. 2A, an exemplary embodiment of a prosthesis 50 (shown in a "rolled out" pattern) comprises a support or stent section 52 and a frond section 54. Support section 52 comprises a first plurality of radially expansible serpentine elements 56 which extend circumferentially to form a cylindrical ring having a plurality of open areas or cells 57 therein. The cylindrical rings formed by serpentine elements 56 are coaxially aligned along the longitudinal axis of the support section 52, and, in the illustrated embodiment, alternate with a second plurality of cylindrical rings formed by radially expandable serpentine elements 58 defining a second set of smaller cells 59. Strut coverage in the range of from about 10% to about 20%, and in some embodiments between about 16%-18% by area is contemplated. A plurality of spaced apart, axially extending struts 61 connect adjacent rings. The particular pattern illustrated for this structure is well-known and chosen to be exemplary of a useful prosthesis. It will be appreciated that a wide variety of other conventional stent structures and patterns may be equally useful as the support section of the prostheses of the present invention. See, for example, FIGS. 2B-2F.

The wall patterns can be varied widely as desired to provide additional coverage, transition in axial stiffness, and accommodate various side branch angles with respect to the main vessel long axis as well as ostial geometries, i.e., diameter and shape.

The support section 52 is joined to the frond section 54 at a plurality of points 65 along a transition line or zone 60. Individual fronds 16, comprise a circumferentially expandable wall pattern. In the embodiment illustrated in FIG. 2A, each frond comprises four curving elements 66 at the distal end of the transition zone 60, which reduce in number to three and then to two in the axial (proximal) direction away from the stent 52. The particular structures shown illustrate one example of a way to achieve circumferential expansion of the individual fronds as the prosthesis is expanded. This is accomplished since each frond is attached to three adjacent serpentine ring apexes 63 in the proximal most serpentine ring 56. Thus, as these serpentine rings 56 are expanded, the circumferential distance between adjacent apexes 63 will increase, thereby causing each frond to "widen" by expanding in a circumferential direction. It would be possible, of course, to join each of the fronds 16 only at a single location to the prosthesis 52, thus allowing the anchors to be deployed without radial expansion. Two or four or more points of attachment may also be used, depending upon the wall pattern and desired performance of the resulting prosthesis. The struts in the transition section are designed to "cup" with adjacent struts such that the gap formed within and between fronds in the expanded prosthesis is minimized.

The circumferentially expandable fronds are curved about the longitudinal axis of the prosthesis and have a number of hinge regions which increase their conformability upon circumferential expansion by a balloon, as described hereinafter. Such conformability is desirable since the fronds will be expanded under a wide variety of differing anatomical conditions which will result in different final geometries for the fronds in use. The final configuration of the fronds in the main vessel lumen will depend on a number of factors, including length of the fronds and geometry of the vasculature and will vary greatly from deployment to deployment. While the fronds together will cover at least a portion of the main vessel wall circumference, most fronds will also be deformed to cover an axial length component of the main vessel wall as well. Such coverage is schematically illustrated in the figures discussed below.

In other embodiments, prosthesis structure 50 can include four or five or six or more fronds 16. Increasing the number of fronds provides an increased number of anchor points between a branch vessel stent and a main vessel stent. This may serve to increase the mechanical linkage between stent 10 and another stent deployed in an adjacent vessel. In various embodiments, fronds 16 can be narrower (in width) than embodiments having few fronds so as to increase the flexibility of the fronds. The increased flexibility can facilitate the bending of the fronds during stent deployment including bending from the branch body lumen into the main body lumen.

Referring now to FIG. 2B, in various embodiments, fronds 16 can comprise thin filaments formed into loops 17. An exemplary embodiment of a prosthesis structure 50 having a plurality of filament loops 17 is shown in FIG. 2B in a rolled out pattern. In various embodiments filament loops 17 can have at least one or two or more intra-filament connectors 18, 19 which extend in a circumferential direction to connect two adjacent filaments defining a filament loop 17. Connectors 18, 19 preferably include at least one nonlinear undulation such as a "U", "V" or "W" or "S" shape to permit radial expansion of the prosthesis in the vicinity of the fronds. (The intra-filament space may be crossed with a balloon catheter and dilated to larger diameters).

The illustrated embodiment includes a first intra-filament connector 18 in the transition area 60 for each frond 16, and a second connector 19 positioned proximally from the first connector 18. One or both of the first and second connectors 18, 19 can be configured to expand or otherwise assume a different shape when the fronds are deployed. At least five or ten or 20 or more connectors 18, 19 may be provided between any two adjacent filaments 66 depending upon the desired clinical performance. Also connectors 18, 19 can be continuous with frond loops 17 and have substantially the same cross sectional thickness and/or mechanical properties. Alternatively, connectors 18, 19 can have different diameters and/or mechanical properties (e.g. one or more of increased elasticity, elastic limit, elongation, stiffness etc.) and or biological properties (surface finish, passivation, coatings, etc.). In one embodiment the distal connector 18 can be stiffer than the proximal connector 19 so as to allow more flexibility at the proximal tip of the fronds.

Connectors 18 and 19 can be further configured to perform several functions. First, to act as mechanical struts to increase the stiffness (e.g. longitudinal, torsional, etc) of the filament fronds 16. Second, when the fronds are deployed, connectors 18 and 19 can be designed to assume a deployed shape which provides radial mechanical support (e.g. act as prosthesis) to the target vessel including at the OS. This is particularly the case for first connector 18 which can be configured to unfurl in the circumferential direction and assume a semi-triangular shape in its deployed state with an expansion axis (of the connected points of the triangle to fronds) substantially parallel to the radial axis of the vessel. This configuration of connector 18 serves to provide radial mechanical support as well as coverage at the OS in particular. Connector 18 can also be configured to assume other deployed shapes as well, such as semi-circular etc. The number and spacing and deployed shape of the connectors 18 can be configured to provide the same amount or density at the OS (e.g. number of struts per axial or radial length of tissue) as the stent region 52 of the prosthesis provides to the rest of the vessel. In general, by varying the dimensions and number of the filaments 66 and connectors 18 any of a variety of physical properties can be achieved. The connectors 18 and 19 and filaments 66 may be selected and designed to cooperate to provide maximum area coverage, and/or maximum mechanical radial force, or either objective without the other. The number of filaments can be in the range of from about 3 to about 30, with specific embodiments of 4, 6, 10, 20 and 25.

In various embodiments, the arrangement of the filaments fronds can be configured to provide several functions. First, as described above they can be configured to provide increased coverage and hence patency of the Os by having an increased number of mechanical support points in the Os and hence a more even distribution of force (e.g. radial force) on the fronds. Also, for embodiments of drug coated stents, including drug eluting stents they provide an increased amount of surface area for the elution of the drug. This in turn, serves to provide increased and/or more constant local concentration of the selected drug at the vessel wall and/or other target site. Other pharmacokinetic benefits can be obtained as well, such as a more constant drug release rate. For stents coated with anti-cell proliferative, anti-inflammatory and/or anti-cell migration drugs such as Taxol (paclitaxel), Rapamycin and their derivatives, the use of high filament type fronds serve as a means to reduce the incidence and rate of hyperplasia and restenosis. Similar results can be obtained with other drugs known in the art for reducing restenosis (e.g. anti-neo-plastics, anti-inflammatory drugs, etc.). Also in a related embodiment the filament fronds can be coated with a different drug and/or a different concentration of drug as the remainder of the stent. In use, such embodiment can be configured to provide one or more of the following: i) a more constant release rate of drug; ii) bimodal release of drug; iii) multi drug therapies; and iv) titration of drug delivery/concentration for specific vessels and/or release rates. As disclosed in additional detail below, the drug may be incorporated into a biostable, biodegradeable, or bioerodable polymer matrix, and may be optimized for long-term pharma release (prophylactic local drug delivery).

In general, in any of the embodiments herein, the prosthesis of the present invention can be adapted to release an agent for prophylactic or active treatment from all or from portions of its surface. The active agents (therapy drug or gene) carried by the prosthesis may include any of a variety of compounds or biological materials which provide the desired therapy or desired modification of the local biological environment. Depending upon the clinical objective in a given implementation of the invention, the active agent may include immunosuppressant compounds, anti-thrombogenic agents, anti-cancer agents, hormones, or other anti-stenosis drugs. Suitable immunosuppressants may include ciclosporina (CsA), FK506, DSG (15-deoxyspergualin, 15-dos), MMF, rapamycin and its derivatives, CCI-779, FR 900520, FR 900523, NK86-1086, daclizumab, depsidomycin, kanglemycin-C, spergualin, prodigiosin25-c, cammunomicin, demethomycin, tetranactin, tranilast, stevastelins, myriocin, gliotoxin, FR 651814, SDZ214-104, bredinin, WS9482, and steroids. Suitable anti-thrombogenic drugs may include antiplatelet agents (GP IIb/IIIa, thienopyridine, GPIb-IX, ASA, etc and inhibitors for the coagulation cascade (heparin, hyrudin, thrombin inhibitors, Xa inhibitors, VIIa Inhibitors, Tissue Factor Inhibitors and the like). Suitable anti-cancer (anti proliferative) agents may include methotrexate, purine, pyridine, and botanical (e.g. paclitaxel, colchicines and triptolide), epothilone, antibiotics, and antibodies. Suitable additional anti-stenosis agents include batimastat, NO donor, 2-chlorodeoxyadenosine, 2-deoxycoformycin, FTY720, Myfortic, ISA (TX) 247, AGI-1096, OKT3, Medimmune, ATG, Zenapax, Simulect, DAB486-IL-2, Anti-ICAM-1, Thymoglobulin, Everolimus, Neoral, Azathioprine (AZA), Cyclophosphamide, Methotrexate, Brequinar Sodium, Leflunomide, or Mizoribine. Gene therapy formulations include Keratin 8, VEGF, and EGF, PTEN, Pro-UK, NOS, or C-myc may also be used.

Methods of preventing restenosis include inhibiting VSMC hyperplasia or migration, promoting endothelial cell growth, or inhibiting cell matrix proliferation with the delivery of suitable compounds from the prosthesis. Radiation, systemic drug therapy and combinations of the foregoing may also be used. The desired dose delivery profiles for the foregoing are in some cases reported in the literature, or may be optimized for use with the prosthesis of the present invention through routine experimentation by those of skill in the art in view of the disclosure herein.

Binding systems (e.g., chemical binding, absorbable and non absorbable polymeric coatings) for releasably carrying the active agent with the prosthesis are well known in the art and can be selected to cooperate with the desired drug elution profile and other characteristics of a particular active agent as will be appreciated by those of skill in the art.

In general, the drug(s) may be incorporated into or affixed to the stent in a number of ways and utilizing any biocompatible materials; it may be incorporated into e.g. a polymer or a polymeric matrix and sprayed onto the outer surface of the stent. A mixture of the drug(s) and the polymeric material may be prepared in a solvent or a mixture of solvents and applied to the surfaces of the stents also by dip-coating, brush coating and/or dip/spin coating, the solvent (s) being allowed to evaporate to leave a film with entrapped drug(s). In the case of stents where the drug(s) is delivered from micropores, struts or channels, a solution of a polymer may additionally be applied as an outlayer to control the drug(s) release; alternatively, the active agent may be comprised in the micropores, struts or channels and the active co-agent may be incorporated in the outlayer, or vice versa. The active agent may also be affixed in an inner layer of the stent and the active co-agent in an outer layer, or vice versa. The drug(s) may also be attached by a covalent bond, e.g. esters, amides or anhydrides, to the stent surface, involving chemical derivatization. The drug(s) may also be incorporated into a biocompatible porous ceramic coating, e.g. a nanoporous ceramic coating. The medical device of the invention is configured to release the active co-agent concurrent with or subsequent to the release of the active agent.

Examples of polymeric materials known for this purpose include hydrophilic, hydrophobic or biocompatible biodegradable materials, e.g. polycarboxylic acids; cellulosic polymers; starch; collagen; hyaluronic acid; gelatin; lactone-based polyesters or copolyesters, e.g. polylactide; polyglycolide; polylactide-glycolide; polycaprolactone; polycaprolactone-glycolide; poly(hydroxybutyrate); poly(hydroxyvalerate); polyhydroxy (butyrate-co-valerate); polyglycolide-co-trimethylene carbonate; poly(dioxanone); polyorthoesters; polyanhydrides; polyaminoacids; polysaccharides; polyphospoeters; polyphosphoester-urethane; polycyanoacrylates; polyphosphazenes; poly(ether-ester) copolymers, e.g. PEO-PLLA, fibrin; fibrinogen; or mixtures thereof; and biocompatible non-degrading materials, e.g. polyurethane; polyolefins; polyesters; polyamides polycaprolactam; polyimide; polyvinyl chloride; polyvinyl methyl ether; polyvinyl alcohol or vinyl alcohol/olefin copolymers, e.g. vinyl alcohol/ethylene copolymers; polyacrylonitrile; polystyrene copolymers of vinyl monomers with olefins, e.g. styrene acrylonitrile copolymers, ethylene methyl methacrylate copolymers; polydimethylsiloxane; poly(ethylene-vinylacetate); acrylate based polymers or copolymers, e.g. polybutylmethacrylate, poly(hydroxyethyl methylmethacrylate); polyvinyl pyrrolidinone; fluorinated polymers such as polytetrafluoroethylene; cellulose esters e.g. cellulose acetate, cellulose nitrate or cellulose propionate; or mixtures thereof.

When a polymeric matrix is used, it may comprise multiple layers, e.g. a base layer in which the drug(s) is/are incorporated, e.g. ethylene-co-vinylacetate and polybutylmethacrylate, and a top coat, e.g. polybutylmethacrylate, which is drug(s)-free and acts as a diffusion-control of the drug(s). Alternatively, the active agent may be comprised in the base layer and the active co-agent may be incorporated in the outlayer, or vice versa. Total thickness of the polymeric matrix may be from about 1 to 20µ or greater.

The drug(s) elutes from the polymeric material or the stent over time and enters the surrounding tissue, e.g. up to ca. 1 month to 10 years. The local delivery according to the present invention allows for high concentration of the drug(s) at the disease site with low concentration of circulating compound. The amount of drug(s) used for local delivery applications will vary depending on the compounds used, the condition to be treated and the desired effect. For purposes of the invention, a therapeutically effective amount will be administered; for example, the drug delivery device or system is configured to release the active agent and/or the active co-agent at a rate of 0.001 to 200 µg/day. By therapeutically effective amount is intended an amount sufficient to inhibit cellular proliferation and resulting in the prevention and treatment of the disease state. Specifically, for the prevention or treatment of restenosis e.g. after revascularization, or antitumor treatment, local delivery may require less compound than systemic administration. The drug(s) may elute passively, actively or under activation, e.g. light-activation.

A possible alternative to a coated stent is a stent containing wells or reservoirs that are loaded with a drug, as discussed by Wright et al., in "Modified Stent Useful for Delivery of Drugs Along Stent Strut," U.S. Pat. No. 6,273,913, issued Aug. 14, 2001; and Wright et al., in "Stent with Therapeutically Active Dosage of Rapamycin Coated Thereon," US patent publication US 2001/0027340, published Oct. 4, 2001, the disclosures of both of which are incorporated in their entireties herein by reference.

Wright et al. in U.S. Pat. No. 6,273,913, describes the delivery of rapamycin from an intravascular stent and directly from micropores formed in the stent body to inhibit neointimal tissue proliferation and restenosis. The stent, which has been modified to contain micropores, is dipped into a solution of rapamycin and an organic solvent, and the solution is allowed to permeate into the micropores. After the solvent has been allowed to dry, a polymer layer may be applied as an outer layer for a controlled release of the drug.

U.S. Pat. No. 5,843,172 by Yan, which is entitled "Porous Medicated Stent", discloses a metallic stent that has a plurality of pores in the metal that are loaded with medication. The drug loaded into the pores is a first medication, and an outer layer or coating may contain a second medication. The porous cavities of the stent can be formed by sintering the stent material from metallic particles, filaments, fibers, wires or other materials such as sheets of sintered materials.

Leone et al. in U.S. Pat. No. 5,891,108 entitled "Drug Delivery Stent" describes a retrievable drug delivery stent, which is made of a hollow tubular wire. The tubular wire or tubing has holes in its body for delivering a liquid solution or drug to a stenotic lesion. Brown et al. in "Directional Drug Delivery Stent and Method of Use," U.S. Pat. No. 6,071,305 issued Jun. 6, 2000, discloses a tube with an eccentric inner diameter and holes or channels along the periphery that house drugs and can deliver them preferentially to one side of the tube. Scheerder et al. in US patent publication US 2002/0007209, discloses a series of holes or perforations cut into the struts on a stent that are able to house therapeutic agents for local delivery.

Referring to the patent literature, Heparin, as well as other anti-platelet or anti-thrombolytic surface coatings, have been reported to reduce thrombosis when carried by the stent surface. Stents including both a heparin surface and an active agent stored inside of a coating are disclosed, for example, in U.S. Pat. Nos. 6,231,600 and 5,288,711.

A variety of agents specifically identified as inhibiting smooth muscle-cell proliferation, and thus inhibit restenosis, have also been proposed for release from endovascular stents. As examples, U.S. Pat. No. 6,159,488 describes the use of a quinazolinone derivative; U.S. Pat. No. 6,171,609, describes the use of taxol, and U.S. Pat. No. 5,176,981, the use of paclitaxel, a cytotoxic agent thought to be the active ingredient in the agent taxol. The metal silver is cited in U.S. Pat. No. 5,873,904. Tranilast, a membrane stabilizing agent thought to have anti-inflammatory properties is disclosed in U.S. Pat. No. 5,733,327.

More recently, rapamycin, an immunosuppressant reported to suppress both smooth muscle cell and endothelial cell growth, has been shown to have improved effectiveness against restenosis, when delivered from a stent. See, for example, U.S. Pat. Nos. 5,288,711 and 6,153,252. Also, in PCT Publication No. WO 97/35575, the monocyclic triene immunosuppressive compound everolimus and related compounds have been proposed for treating restenosis, via systemic delivery.

Use of multiple filaments per frond also provides for a more open structure of the fronds section 54 of the prosthesis to allow for an easier and less obstructed passage of a guide wire and/or the deployment balloon by and/or through the fronds (e.g., during un-jailing procedures known in the art). Similarly, use of the flexible filaments also allows the main vessel to track between fronds and engage the main vessel stent. In particular, the thinner frond filaments facilitate advancement of the fronds over the circumference and/or the length of a main vessel stent during deployment of the fronds or the main vessel stent. Moreover, the filaments can be configured to be easily withdrawn and then re-advanced again to allow for repositioning of either of the branch vessel stent. Other means for facilitating advancement of the main vessel stent between the fronds can include tapering the fronds and/or coating the fronds with a lubricous coating such as PTFE or silicone (this also facilitates release of the fronds from constraining means described herein). Finally, by having an increased number of filaments, the mechanical support of the Os is not compromised if one or more filaments should become pushed aside during the stent deployment. That is, the remaining filaments provide sufficient support of the Os to maintain it patency. In these and related embodiments, it may be desirable to have at least six loops 17 each comprising at least one filament looped back upon itself at its proximal limit to provide at least two elements per frond.

Various embodiments of the fronds can be configured to provide an increased amount of mechanical linkage between the fronds and the main vessel stent. In general, the frond design seeks to 1) track to site, 2) allow for advancement of MV Stent 3) increase frond-MV stent interaction and 4) frond MV wall interactions. Another means includes increasing the number of fronds to provide an increased number of anchor points between a branch vessel stent and a main vessel stent. This in turn provides an increased amount of mechanical linkage between the two stents such that they increasingly operate mechanically as one structure rather than two after deployment. This also serves to improve the spatial stability of the deployed stents within both vessels. That is, there is reduced movement (e.g., axial or radial) or reduced possibility of movement of one or both stents within their respective vessels. In particular, the linkage serves to provide radial strength of the structure in the ostium.

Referring now to FIG. 2C in an alternative embodiment of a prosthesis 50 having filament fronds 17, one or two or more frond can be a shortened frond 16s. That is a frond that is shortened in the longitudinal direction. In the illustrated embodiment, shortened fronds 16s and full length fronds 16 alternate around the circumference of the stent. The amount of shortening can range from 10% to 99%. In a preferred embodiment, fronds 16s are shortened by approximately slightly less than 50% in length from the length of un-shortened fronds 16. Embodiments having shortened fronds, reduce the likelihood of resistance when the main vessel stent 150 is positioned. Shortened fronds 16s also can be configured to act more like point contacts on the main vessel stent 150 and should therefore be less likely to be swept towards the Os by deployment and/or misalignment of the main vessel stent and deployment balloon. Also, use of less material in the fronds tends to produce less displacement of the fronds even if the main vessel stent or balloon catches multiple fronds, and may produce a lower biological reaction (less foreign material).

FIGS. 2D and 2E illustrate an alternative side wall patterns for the transition portion of the prosthesis of the present invention, on stents having two different side wall patterns. As described previously, the specific stent or other support structure configuration may be varied considerably within the context of the present invention.

In each of the embodiments of FIGS. 2D and 2E, the struts 70 at the frond root (e.g. transition zone) are provided with an interdigitating or nesting configuration. In this configuration, as viewed in the flat, laid out view as in FIGS. 2D and 2E, a plurality of struts 70 extend across the transition zone. A distal segment 72 of each strut 70 inclines laterally in a first direction, to an apex 74, and then inclines laterally in a second direction to a point that may be approximately axially aligned with a distal limit of the distal segment 72. The extent of lateral displacement of the strut between its origin and the apex 74 is greater than the distance between adjacent struts, when in the unexpanded configuration. In this manner, adjacent struts stack up or nest within each other, each having a concavity 78 facing in a first lateral direction and a corresponding convexity 80 in a second lateral direction. This configuration seeks to optimize vessel wall coverage at the ostium, when the stent is expanded.

The axial length of each frond is at least about 10%, often at least about 20%, and in some embodiments at least about 35% or 75% or more of the length of the overall prosthesis. Within this length, adjacent fronds may be constructed without any lateral interconnection, to optimize the independent flexibility. The axially extending component of the frond may be provided with an undulating or serpentine structure 82, which helps enable the fronds to rotate out of the plane when the main vessel stent is deployed. Circumferential portions of the undulating fronds structure make the frond very flexible out of the plane of the frond for trackability. A plurality of connectors 84 are provided between parallel undulating filaments 86, 88 of each frond, to keep the frond from being overly floppy and prone to undesirable deformation. Each of the fronds in the illustrated embodiment has a broad (i.e.

relatively large radius) frond tip 90, to provide an atraumatic tip to minimize the risk of perforating the arterial or other vascular wall.

The interdigitating construction in the transition zone, as well as the undulating pattern of the frond sections both provides optimal coverage at the ostium, and provides additional strut length extension or elongation capabilities, which may be desirable during the implantation process.

It may also be desirable to vary the physical properties of the filaments, 86, 88, or elsewhere in the prosthesis, to achieve desired expansion results. For example, referring to FIG. 2E, each frond 16 includes a first filament 92, attached at a first attachment point 94 and a second filament 96 attached at a second attachment point 98 to the stent. A third filament 100 and a fourth filament 102 are connected to the stent at an intermediate attachment point 104. As illustrated, the transverse width of the third and fourth filaments 100 and 102 are less than the transverse width of the first and second filaments 92, 96. The thinner filaments 100, 102 provide less resistance to expansion, and help maintain optimal coverage in the vicinity of the ostium upon expansion of the prosthesis.

In any of the embodiments described herein, the fronds may be considered to have a lumenal surface at least a portion of which will be in contact with an outside surface of the main vessel stent, and an ablumenal surface which will be pressed into contact with the vascular wall by the main vessel stent. The lumenal and ablumenal surfaces of the fronds may be provided with similar or dissimilar characteristics, depending upon the desired performance. For example, as described elsewhere herein, the frond and particularly the ablumenal surface may be provided with a drug eluting characteristic.

It may also be desirable to modify the lumenal surface of the frond, to enhance the physical interaction with the main vessel stent. For this purpose, the lumenal surface of the frond may be provided with any of a variety of friction enhancing surface characteristics, or engagement structures for engaging the main vessel stent. Friction enhancing surfaces may comprise the use of polymeric coatings, or mechanical roughening such as laser etching, chemical etching, sputtering, or other processes. Alternatively, any of a variety of radially inwardly extending hooks or barbs may be provided, for engaging the main vessel stent. Preferably, any radially inwardly extending hooks or barbs will have an axial length in the radial direction of no greater than approximately the wall thickness of the main vessel stent strut, to minimize the introduction of blood flow turbulence. Although a variety of main vessel stents are available, the inventors presently contemplate wall thicknesses for the struts of such main vessel stents to be on the order of about 0.003 to 0.0055 inches for native coronary indications. Any of the foregoing surfaces textures or structures may also be provided on the ablumenal surface of the main vessel stent, to cooperate with corresponding textures or structures on the fronds, to enhance the physical integrity of the junction between the two, and potentially reduce the risk for vessel perforation by fronds.

As will be described in additional detail in connection with the method, below, proper positioning of the prosthesis with respect to the bifurcation may be important. To facilitate positioning of the transition zone relative to the carina or other anatomical feature of the bifurcation, the prosthesis is preferably provided with a first radiopaque marker at a distal end of the transition zone and a second radiopaque marker at the proximal end of the transition zone. The proximal and distal radiopaque markers may take the form of radiopaque bands of material, or discreet markers which are attached to the prosthesis structure. This will enable centering of the transition zone on a desired anatomical target, relative to the ostium of the bifurcation. In general, it is desirable to avoid positioning the stent or other support such that it extends into the main vessel. A single marker may be used to denote the placement location of the transition zone.

Alternatively, the marker band or bands or other markers may be carried by the deployment catheter beneath the prosthesis, and axially aligned with, for example, the proximal and distal ends of the transition zone in addition to markers delineating the proximal and distal end of the prosthesis Although the prosthesis has been disclosed herein primarily in the context of a distal branch vessel stent carrying a plurality of proximally extending fronds, other configurations may be constructed within the scope of the present invention. For example, the orientations may be reversed such that the fronds extend in a distal direction from the support structure. Alternatively, a support structure such as a stent may be provided at each of the proximal and distal ends of a plurality of frond like connectors. This structure may be deployed, for example, with a distal stent in the branch lumen, a plurality of connectors extending across the ostium into the main vessel, and the proximal stent deployed in the main vessel proximal to the ostium. A separate main vessel stent may thereafter be positioned through the proximal stent of the prosthesis, across the ostium and into the main vessel on the distal side of the bifurcation.

In addition, the prosthesis has been primarily described herein as a unitary structure, such as might be produced by laser cutting the prosthesis from a tubular stock. Alternatively, the prosthesis may be constructed such as by welding, brazing, or other attachment techniques to secure a plurality of fronds onto a separately constructed support. This permits the use of dissimilar materials, having a variety of hybrid characteristics, such as a self expandable plurality of fronds connected to a balloon expandable support. Once released from a restraint on the deployment catheter, self expandable fronds will tend to bias radially outwardly against the vascular wall, which may be desirable during the process of implanting the main vessel stent. Alternatively, the entire structure can be self expandable or balloon expandable, or the support can be self expandable as is described elsewhere herein. In general, the proximal end of the fronds will contribute no incremental radial force to the prosthesis. The distal end of the fronds may contribute radial force only to the extent that it is transmitted down the frond from the support structure.

In each of the embodiments illustrated in FIGS. 2A-2E, the fronds have been illustrated as extending between a first end which is attached to the support 52, and a second, free end. In any of the frond designs disclosed herein, it may be desirable to provide a connection between the fronds in the vicinity of the free end. The connection may be accomplished in any of a variety of ways, such as providing a series of interfrond segments or connections, which, when deployed and expanded, form a circumferential ring which links the fronds. Alternatively, the circumferential link may be frangible, such that it maintains the spatial orientation of the fronds prior to a final expansion step, but is severed or otherwise releases the fronds upon final expansion.

The provision of a circumferential link at the proximal end of the fronds may provide a variety of benefits. For example, in an embodiment intended for balloon expansion at the treatment site, the circumferential link will assist in maintaining the crimped profile of the fronds on the balloon during transluminal navigation. The circumferential link may be configured with sufficient holding force that an outer sleeve such as those discussed in connection with FIGS. 5 and 6 may be omitted. In addition, the provision of a circumferential link may provide sufficient radiopacity either by itself or by carrying separate radiopaque markers to permit visualization of the ends of the fronds.

Once at the treatment site, the circumferential link will assist in maintaining the spacing of the fronds and also in holding the proximal ends of the fronds open to facilitate advancement of the main vessel stent therethrough. The circumferential link may additionally assist in controlling the fronds if, during the procedure, it is determined to crush the fronds against a wall of the vessel. The circumferential link will assist in maintaining the fronds against the wall while a secondary strategy is employed.

The circumferential link may be provided by any of a variety of techniques which will be understood to those in the stent manufacturing arts. For example, the circumferential link may be formed integrally with the stent and fronds such as by laser cutting from tube stock. Alternatively, the circumferential link may be attached to previously formed fronds, using any of a variety of bonding techniques such as welding, brazing, adhesives or others depending upon the materials of the fronds and circumferential link. Although it may add to the wall thickness, the circumferential link may be interlocked with or crimped to the fronds.

The circumferential link may alternatively be a polymeric band or tubular sleeve. For example, a radially expandable tubular sleeve may be positioned around the outside surface of the fronds, or adjacent the lumenal surface of the fronds. A polymeric circumferential link may also be formed such as by dipping the fronds or spraying the fronds with a suitable polymeric precursor or molten material. Polymeric circumferential links may be permanent, severable, or may be bioabsorbable or bioerodeable over time.

Figure 2F:
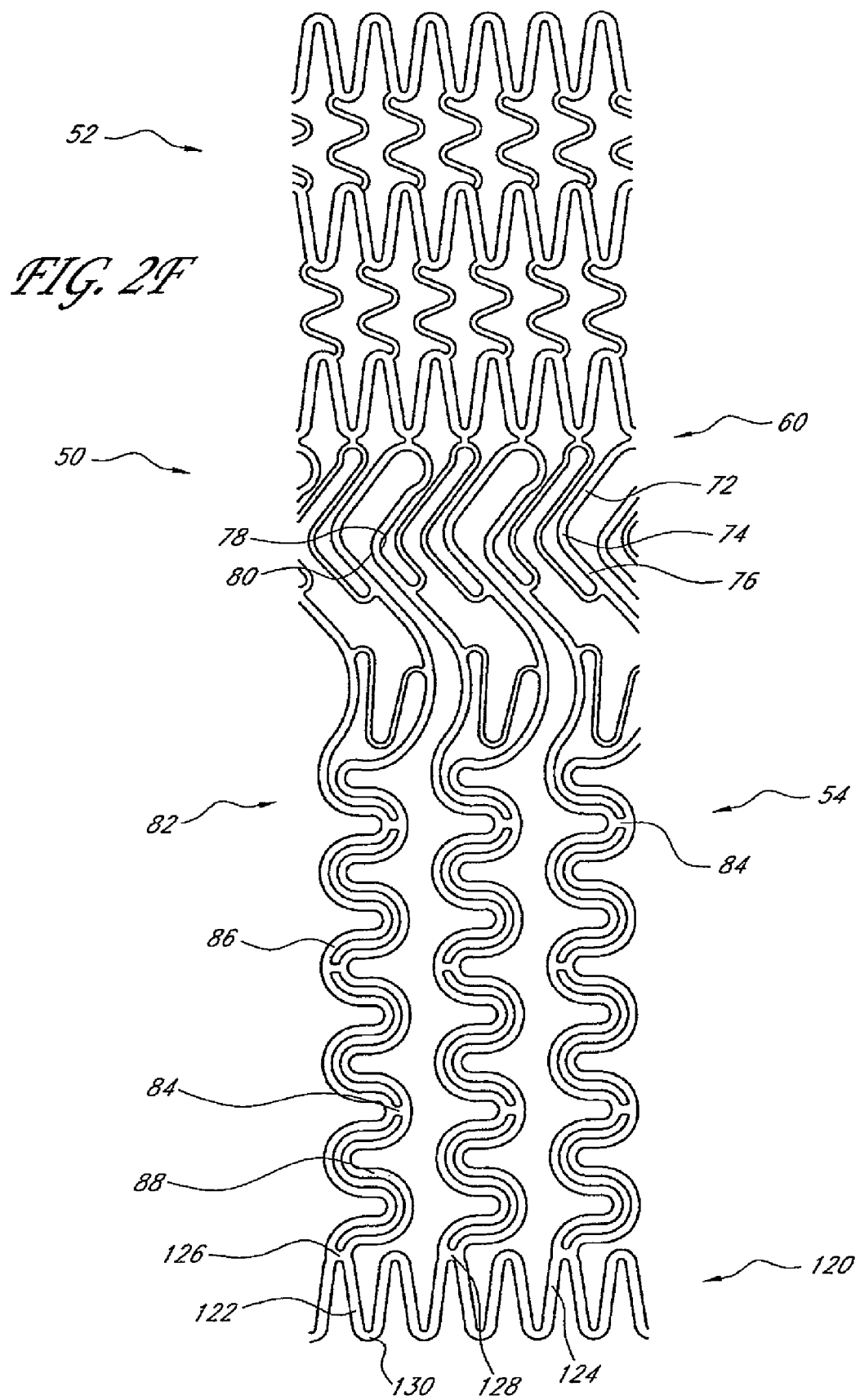
FIG. 2F is a lateral view as in FIG. 2D, with the added feature of a circumferential link to assist in maintaining the spacial orientation of the fronds.

One embodiment of a circumferential link is illustrated schematically in FIG. 2F. In this embodiment, a circumferential link 120 is provided, which connects each adjacent pair of fronds together, to produce a circumferential link 120 which extends completely around the axis of the prosthesis. In this illustration, the circumferential link 120 thus comprises a discrete transverse connection between each adjacent pair of fronds. Thus, for example, a first segment 122 is provided between a first and a second frond. The first segment 122 is expandable or enlargeable in a circumferential direction. A first segment 122 has a first end 126 at the point of attachment of the first segment 122 to a first frond, and a second end 128 at a point of attachment between the first segment 122 and a second frond. The arc distance or the linear distance between the first end 126 and second end 128 measured in a plane transverse to the longitudinal axis of the prosthesis is enlargeable from a first distance for transluminal navigation, to a second distance following expansion of the fronds within the main vessel. To accommodate the radial expansion of the circumferential link 120, the first segment 122 is provided with an undulating configuration having at least one and optionally 2 or three or more apex 130, as will be understood in the art. In one embodiment, each adjacent pair of fronds is connected by a transverse segment (e.g., 122, 124 etc.) and each of the transverse segments is identical to each other transverse segments.

Although the first segment 122 and second segment 124 are each illustrated in FIG. 2F as comprising only a single transversely extending filament, two or three or more filaments may be provided between each adjacent pair of fronds, depending upon the desired performance. As used herein, the term "circumferential link" does not limit the link 120 to only a single filament between adjacent fronds. For example, the circumferential link may comprise a stent or other support structure which is similar to the support structure 52.

In general terms, the prosthesis 50 may be considered to be a tubular structure which comprises a plurality of axially extending fronds having a first radially expandable structure on a first end and a second radially expandable structure on a second end. The first radially expandable structure is a support structure 52 such as a stent, as has been described for positioning within the branch vessel. The second radially expandable structure comprises the circumferential link 120.

Typically, the circumferential link 120 will provide significantly less radial force than the first support structure 52, in view of its primary function to maintain the spacing and orientation of the fronds rather than providing support to the vessel wall. In a typical embodiment, the support structure 52 will have a first radial force, the circumferential link 120 will have a second, lesser radial force, and the fronds will contribute nothing or essentially nothing to the radial force of the structure. Alternatively, the circumferential link 120 may have a radial force which is approximately equal to the radial force of the support structure 52, and possibly even in excess of the radial force of the support structure 52, depending upon the desired clinical performance. The fronds may exhibit a radial force, which may be due mostly or entirely to the adjacent stent or circumferential link.

In an implementation of the invention intended for use in the coronary arteries, the stent portion may have a crush resistance or radial strength on the order of at least about 10 psi or 12 psi, and, often at least about 14 or 15 psi. The circumferential link may have a radial force or crush resistance of no greater than about 90%, often no greater than about 50%, and in some embodiments no greater than about 25% of the radial force or crush resistance of the branch vessel stent. Thus, in a prosthesis having a stent with a crush resistance of at least about 14 or 15 psi, the circumferential link might have a crush resistance of less than about 4 or 3 psi. The crush resistance in the fronds may be less than about 2 psi or less than about 1 psi, depending upon the length of the fronds, structure of the fronds, crush resistance of the adjacent structures, and other factors that may affect the cantilevered transfer of radial force from the adjacent stent or circumferential link.

Radial strength or crush resistance as used herein, may be determined in psi by constructing a radial strength test fixture. In general, the radial strength test fixture comprises a pressured chamber, adapted to allow the insertion of a flexible tube which can be sealed at each end to the walls of the chamber such that the exterior wall of the tubing is exposed to the pressure generated in the chamber while the central lumen of the tube is exposed to ambient atmospheric pressure. Any of a variety of thin walled flexible tubing may be utilized, such as a thin walled latex tubing, such that the inside diameter of the latex tubing may be approximately 10% less than the nominal expanded diameter of the stent. The stent is expanded within the tubing, such as by inflating an associated dilation balloon to its rated burst pressure or other pressure sufficient to expand the stent to its intended implanted diameter. The balloon may be deflated and the balloon catheter withdrawn. The tubing is mounted in the pressure chamber as described above. Air or other inflation media may be pumped into the pressure chamber to slowly increase the pressure within the chamber (for example at a rate of about 1 psi per second). Once any portion of the central lumen through the prosthesis has been reduced under pressure to less than or equal to 50% of its original lumen diameter, the pressure in the chamber is noted and considered to be the radial force or crush resistance of the prosthesis.

The second radially expandable structure (circumferential link) may also have a shorter axial length than the first radially expandable structure (stent). For example, in a coronary artery embodiment, the axial length of the stent may be at least 300% or 500% or more of the length of the circumferential link.

The fronds will have a length in the axial direction between the support 52 and the circumferential link 120 of generally in excess of about 2.5 mm or 3 mm, and in certain embodiments in excess of about 5 mm. At least some or all of the fronds may have a length in excess of about 8 mm, and, in one implementation of the invention intended for the coronary artery, the frond length is in the vicinity of about 9.4 mm.

The circumferential link may also have a smaller strut profile compared to the strut profile in the support 52. For example, the cross sectional dimensions of a strut in the support 52 and/or the fronds may be on the order of about 0.003 inches by about 0.055 inches in an embodiment intended for coronary artery applications. In the same embodiment, the cross sectional dimensions through a strut in the circumferential link may be on the order of about 0.001 inches by about 0.003 inches.

The frond length may also be evaluated relative to the main lumen diameter. For example, in the coronary artery environment, diameters in the range of from about 2 mm to about 5 mm are often encountered. Frond lengths of at least about equal to the main vessel diameter (e.g. at least about 2 mm or 3 mm or 4 mm or greater) are contemplated. Fronds lengths of as much as 2 times or 3 times or 4 times or more of the diameter of the associated main vessel are also contemplated.

Figure 14A:
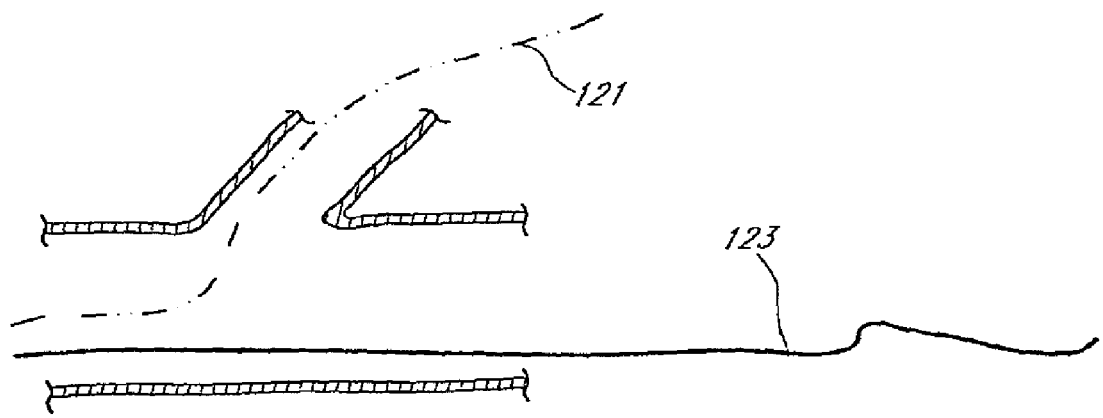
FIGS. 14A-14E are a sequence of schematic illustrations showing the deployment of a vascular bifurcation prosthesis with linked fronds.
Figure 14B:
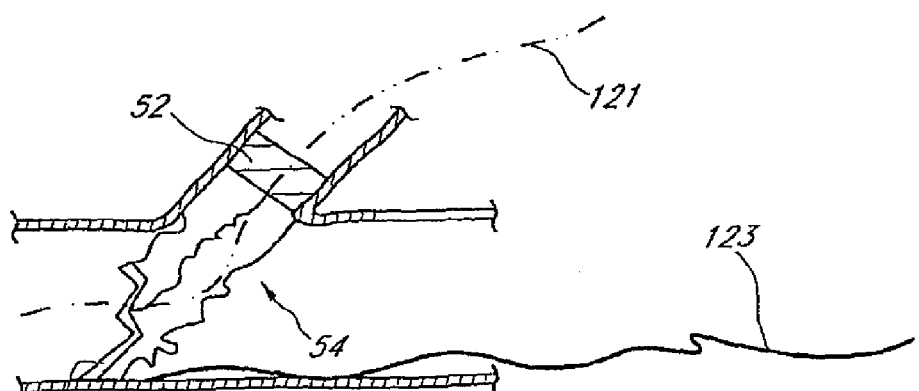

Deployment of the bifurcation prosthesis with linked fronds may be understood by reference to FIGS. 14A-14E. In FIG. 14A, the side branch guidewire 121 has been positioned in the side branch and the main vessel guidewire 123 has been positioned in the main vessel. The side branch stent is next deployed in the side branch, with the fronds extending across the ostium and into the main vessel. The circumferential link 120 may either self expand or be balloon expandable to provide a main vessel stent opening. See FIG. 14B.

Figure 14C:
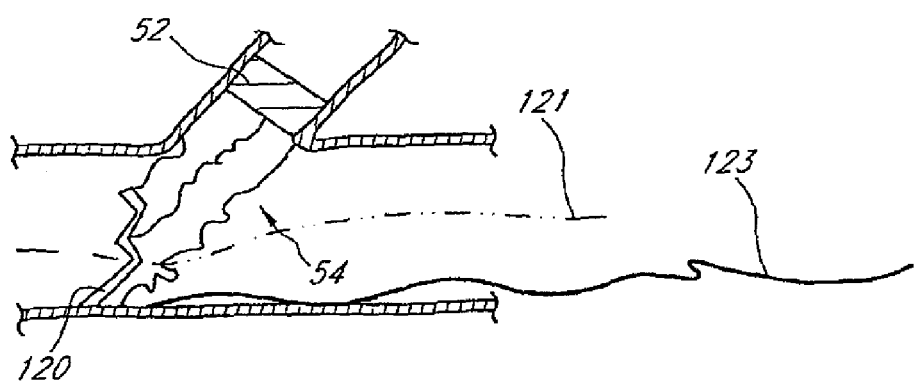

Referring to FIG. 14C, the side branch wire is retracted from the side branch and advanced between the fronds into the main vessel. The main vessel wire 123 may be retracted at this point in the procedure. The main vessel stent is then advanced over the wire through the opening formed by the circumferential link, and through a space between adjacent fronds into the desired position.

Figure 14D:
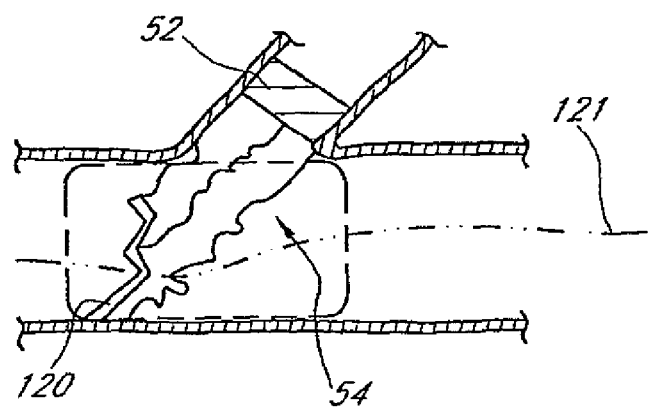
Figure 14E:
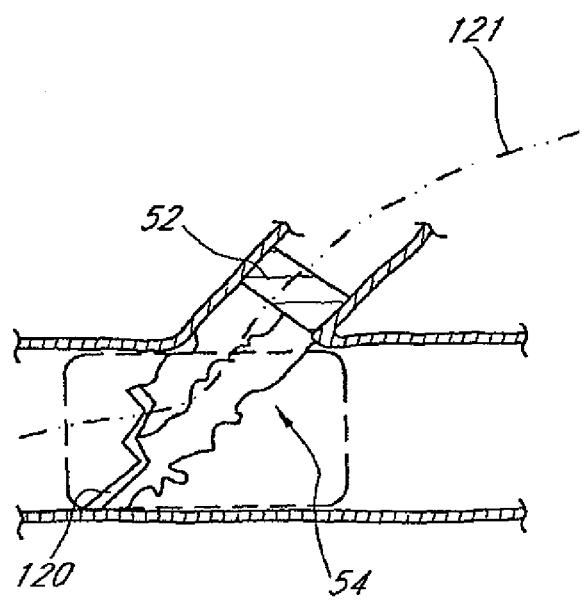

Referring to FIG. 14D, the main vessel stent is deployed to entrap the fronds against the vessel wall. The circumferential link is additionally trapped against the vessel wall. Post dilation to open the side wall opening into the branch vessel may optionally be accomplished, by retracting the side branch wire and readvancing it into the side branch. See FIG. 14E.

Based upon the foregoing description, it will be apparent to those of skill in the art that the prosthesis of the present invention may be implanted in a variety of alternative manners. For example, the first support structure (described above as a side branch stent) may be positioned in the main vessel, distally (from the perspective of the delivery catheter) of the bifurcation with the fronds extending proximally across the opening to the side branch. The second support structure (referred to above as a circumferential link), if present, is positioned in the main vessel proximally of the side branch opening. A standard stent may then be positioned such that the distal end of the stent is within the side branch, and a proximal end of the stent is within the main vessel, such as within the circumferential link.

Figure 3A:
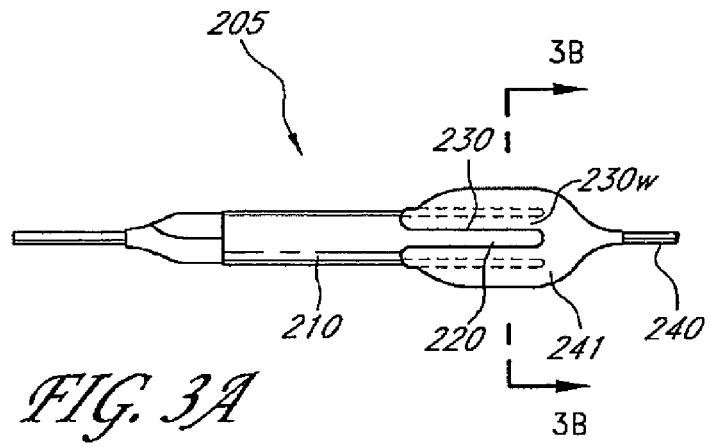
FIGS. 3A and 3B are lateral and cross sectional views illustrating an embodiment of a stent having fronds and an underlying deployment balloon having a fold configuration such that the balloon folds protrude through the spaces between the fronds.
Figure 3B:
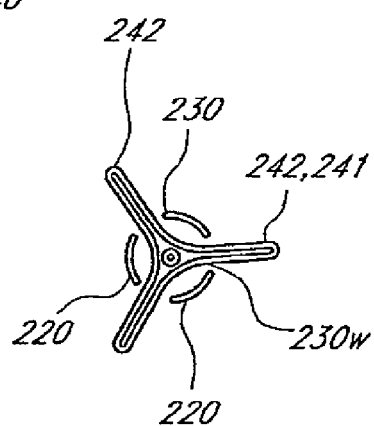
Figure 4A:
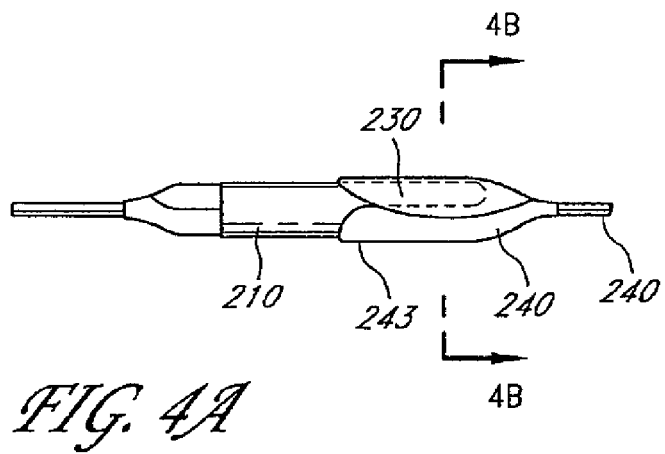
FIGS. 4A and 4B are lateral and cross sectional views illustrating the embodiment of FIGS. 3A and 3B with the balloon folded over to capture the fronds.
Figure 4B:
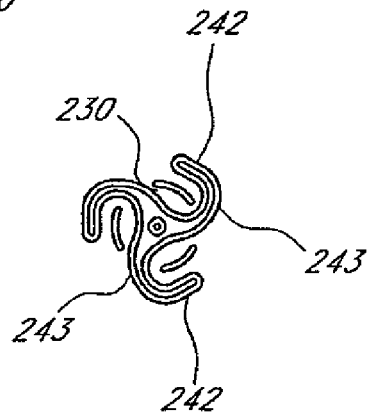

Referring now to FIGS. 3A-8, in various embodiments prosthesis/delivery system 205 can include a prosthesis with stent 210 and fronds 220 which are configured to be captured or otherwise radially constrained by the delivery system during advancement of the stent through the vasculature or other body lumen. As shown in FIGS. 3A-3B, fronds 220 can be separated by axial gaps or splits 230 along the length of the frond structure. Splits 230 can have a variety of widths and in various embodiments, can have a width between 0.05 to 2 times the width of the fronds, with specific embodiments of no more than about 0.05, 0.25, 0.5, 1 and 2 times the width of the fronds. Fronds 220 can be configured to have sufficient flexibility to be advanced while in a captured mode through curved and/or tortuous vessels to reach the more distal portions of the vasculature such as distal portion of the coronary vasculature. This can be achieved through the selection of dimensions and/or material properties (e.g. flexural properties) of the fronds. For example, all or a portion of fronds 220 can comprise a resilient metal (e.g., stainless steel) or a superelastic material known in the art. Examples of suitable superelastic materials include various nickel titanium alloys known in the art such as Nitinol™.

Any of a variety of modifications or features may be provided on the fronds, to enhance flexibility or rotatability in one or more planes. For example, fronds may be provided with a reduced thickness throughout their length, compared to the thickness of the corresponding stent. The thickness of the frond may be tapered from relatively thicker at the distal (attachment) end to the proximal free end. Fronds may be provided with one or more grooves or recesses, or a plurality of wells or apertures, to affect flexibility. The specific configuration of any such flexibility modifying characteristic can be optimized through routine experimentation by those of skill in the art in view of the present disclosure, taking into account the desired clinical performance.

It is desirable to have the fronds captured and held against the delivery catheter or otherwise restrained as the stent is advanced through the vasculature in order to prevent the fronds from divaricating or separating from the prosthesis delivery system prosthesis. Capture of the fronds and prevention of divarication can be achieved through a variety of means. For example, in various embodiments the capture means can be configured to prevent divarication by imparting sufficient hoop strength to the fronds, or a structure including the fronds, to prevent the fronds from separating and branching from the deployment balloon as the balloon catheter is advanced through the vasculature including tortuous vasculature. In theses embodiments, the capture means is also configured to allow the fronds to have sufficient flexibility to be advanced through the vasculature as described above.

In an embodiment shown in FIGS. 3A-4B, the fronds can be captured under the flaps 242 of a deployment balloon 241 of a delivery balloon catheter 240. In this and related embodiments, the balloon 241 and stent 210 can be configured such that flaps 242 are substantially matched up or aligned with splits 230. This can be achieved using alignment techniques known in the art (e.g., use of alignment fixtures) when the stent 220 is positioned over balloon 241. The flap material will initially extend or protruded through the splits, but is then folded over onto one or more fronds 220 to capture those fronds. In an embodiment, this can be achieved by partially inflated and then deflated the balloon, with folding done after the inflation or deflation. Folding can be done by hand or using a capture tube or overlying sleeve known in the art. Also in an embodiment, folding can be facilitated by the use of one or more preformed folds 243, also known as fold lines 243. Folds 243 can be formed using medical balloon fabrication methods known in the art such as mold blowing methods known in the art. In an embodiment using folds 243, folding can be achieved by inflating the balloon with the overlying fronds in place, so as to have the balloon flaps 242 protrude through splits 230, then the balloon is deflated to have flaps 242 fold back over fronds 220 at fold lines 243.

Once stent 210 is properly positioned at the target vessel site, balloon 241 is at least partially inflated which unfurls flaps 242 covering fronds 220 so as to release the fronds. Once released, deployment balloon 241 can also be used to expand or otherwise deform the fronds 220 to deploy them in the selected vessel as is described herein. Alternatively, a second balloon can be used to expand and deploy the fronds as is also described herein.

To avoid pinching the balloon material of balloon 241 between layers of stent metal during the stent crimping process in one embodiment, fronds 220 can be configured such that they do not overlap when crimped down to a smaller diameter. This can be achieved by configuring the fronds to be sufficiently narrow so that crimping the stent to a smaller diameter does not cause them to overlap, or through the use of a crimping fixture or mandrel known in the art. In various embodiments, fronds 220 can be configured to have a selectable minimum split width 230w between spits 230 after crimping. This can be in the range of 0.001 to about 0.2 inches with specific embodiments of 0.002, 0.005, 0.010, 0.025, 0.050 or 0.1 inches.

In another embodiment for using the delivery balloon catheter to capture the fronds, a section of a balloon 241 (not shown) can be configured to evert or fold back over a proximal portion of the stent and thus overly and capture the fronds. When the balloon is inflated, the overlying section of balloon material unfolds, releasing the fronds. The everted section of balloon can over all or any selected portion of the fronds. Eversion can be facilitated through the use of preformed folds described herein, in the case, the folds having a circumferential configuration. The folded section of balloon can be held in place by a friction fit or through the use of releasable low-strength heat bond or adhesive known in the art for bonding the balloon to the fronds. In one embodiment for positioning the everted section, the balloon is positioned inside the scaffold section of the stent and then partially inflated to have an end of the balloon protrude outside of the scaffold section, then the balloon is partially deflated and everted section is rolled over the fronds and then the balloon is fully deflated to create a vacuum or shrink fit of the balloon onto the fronds.

Figure 5A:
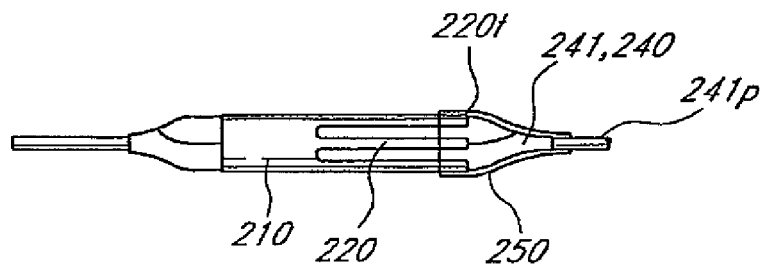
FIGS. 5A-5C are lateral views illustrating the deployment of stent fronds using an underlying deployment balloon and a retaining cuff positioned over the proximal portion of the balloon.
Figure 5B:
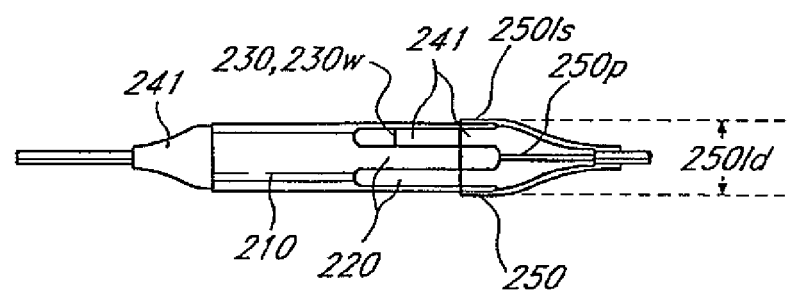
Figure 5C:
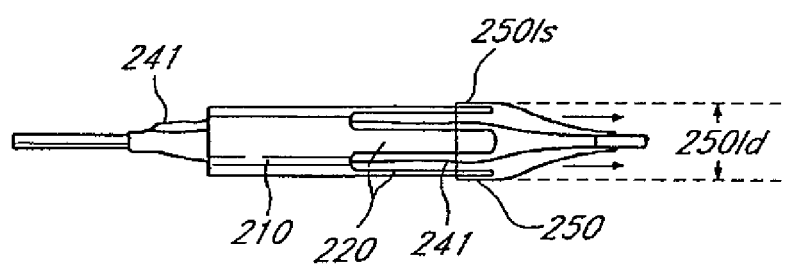

In various embodiments, fronds 210 can be captured by use of a tubular cuff 250 extending from the proximal end 241p of delivery balloon 241 as is shown in FIGS. 5A-5C. In one embodiment, the cuff is attached to the catheter at or proximal to the proximal end 241p of the delivery balloon. In alternative embodiments, the cuff can be attached to a more proximal section of the catheter shaft such that there is an exposed section of catheter shaft between balloon and the cuff attachment point with the attachment point selected to facilitate catheter flexibility. Alternatively, the cuff is axially movably carried by the catheter shaft, such as by attachment to a pull wire which extends axially along the outside of or through a pull wire lumen within the catheter shaft, or to a tubular sleeve concentrically carried over the catheter shaft. In either approach, the cuff is positionable during translumenal navigation such that it overlies at least a portion of the fronds 220.

After prosthesis 210 is positioned at the target vascular site, the stent region is deployed using the delivery balloon as described herein. The frond(s) can be released by withdrawal of the restraint. In most embodiments, the entire catheter assembly including the cuff or other restraint, balloon, and catheter shaft are withdrawn proximally to fully release the fronds. In alternative embodiment the cuff can be slidably withdrawn while maintaining position of the delivery balloon. This embodiment permits frond release prior to or after stent deployment.

Release of the fronds by the cuff can be achieved through a variety of means. In one embodiment, cuff 250 can be configured such that the proximal frond tips 220t, slip out from the cuff when the balloon is deployed. Alternatively, the cuff may be scored or perforated such that it breaks at least partially open upon balloon deployment so that it releases fronds 220. Accordingly, in such embodiments, cuff 250 can have one or more scored or perforated sections 250p. In such embodiments, portions of cuff 250 can be configured to break open at a selectable inflation pressure or at a selectable expanded diameter. In one embodiment, the cuff material can be fabricated from a polymer that it is more plastically deformable in a radial direction than axially. Such properties can be achieved by extrusion methods known in the polymer arts so as to stretch the material axially. In use, such materials allow the cuff to plastically deform in the radial when expanded by the deployment balloon, and then to stay at least partially deformed when the balloon is deflated so as to still cover the fronds. An example of such a material includes extruded Low density Polyethylene (LDPE). Further description of the use of the cuff 250 and other capture means may be found in U.S. patent application Ser. No. 10/965,230 which is fully incorporated by reference herein.

In various embodiments, cuff 250 can be configured such that it plastically deforms when the balloon is inflated and substantially retains its "inflated shape" 250is and "inflated diameter" 250id after the balloon is deflated is shown in FIGS. 5B and 5C. This can be achieved through the selection of plastically deformable materials for cuff 250 (e.g. plastically deformable polymers), the design of the cuff itself (e.g. cuff dimensions and shape) and combinations thereof. For example, a cuff fixed to a catheter shaft and having the same approximate internal diameter as the deployed stent may be folded over the stent fronds to constrain them (using conventional balloon folding techniques). That cuff may be unfolded when the stent deployment balloon is inflated and the fronds released. The cuff can be withdrawn along the balloon and catheter. In an alternative embodiment of a folded-over cuff, the cuff is relatively inelastic and has an internal diameter approximately that of the deployed stent.

Figure 6A:
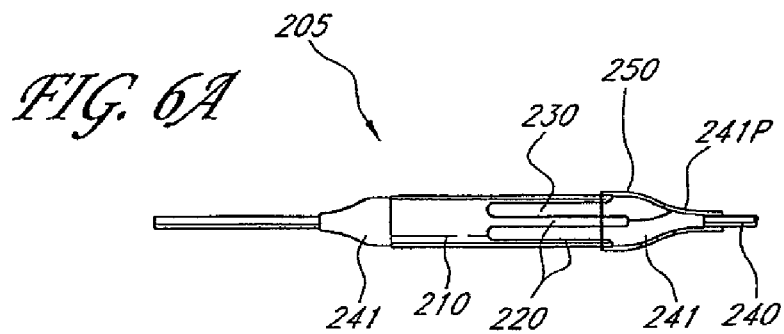
FIGS. 6A-6B are lateral views illustrating the change in shape of the cuff during deployment of a stent with fronds.
Figure 6B:
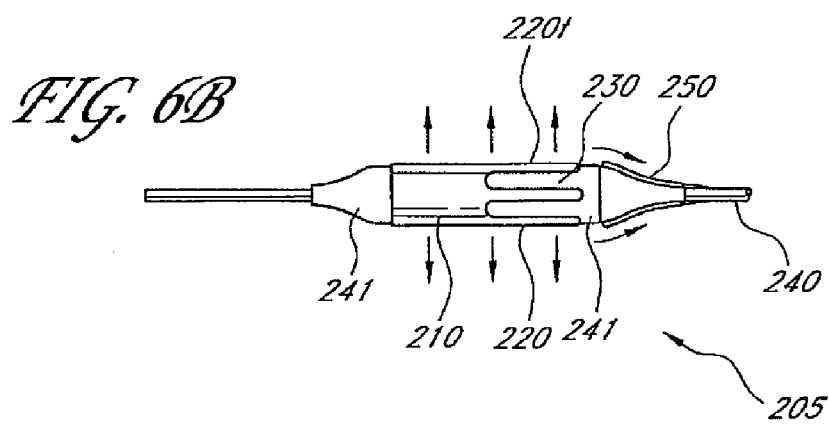

Also the cuff can be configured such that it shortens axially as it is expanded by the deployment balloon or other expansion device. This can be accomplished by selecting the materials for cuff 250 such that the cuff shrinks axially when it is stretched radially as is shown in FIGS. 6A and 6B. Accordingly, in one embodiment, the cuff can be made of elastomeric material configured to shrink axially when stretched radially.

Figure 6C:
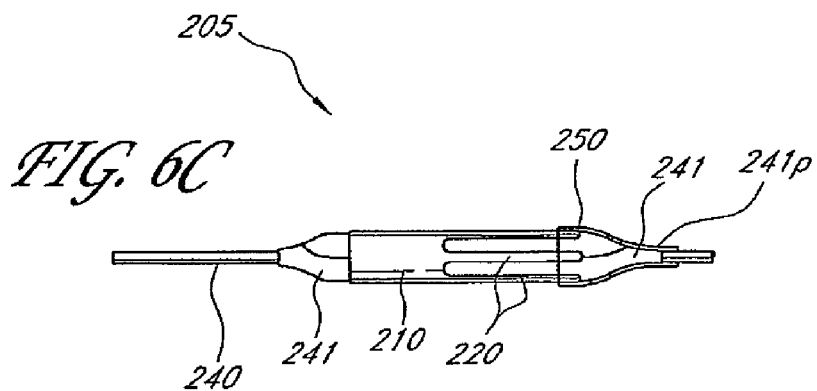
FIGS. 6C-6D are lateral views illustrating an embodiment of a cuff configured to evert upon balloon inflation to release the fronds.
Figure 6D:
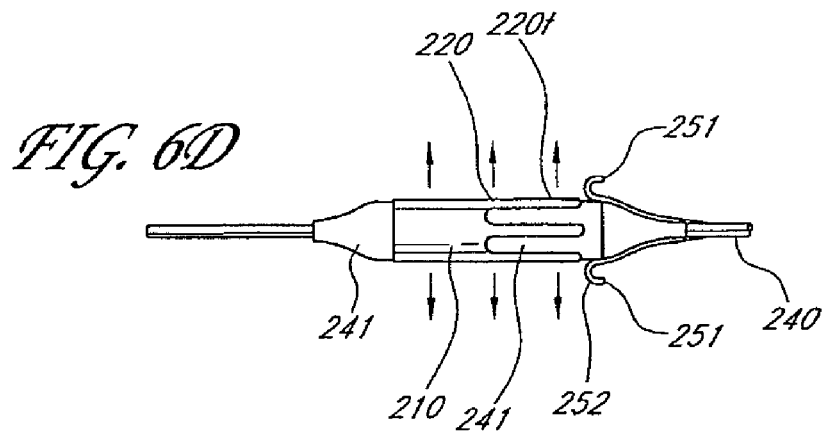

In another embodiment, all or a portion of the cuff can be configured to fold over or evert onto itself upon inflation of the balloon to produce an everted section 251 and so release the enveloped fronds as is shown in FIGS. 6C-6D. This can be facilitated by use of fold lines 252 described herein, as well as coupled the cuff to the balloon catheter. In one embodiment the cuff can be coaxially disposed over the proximal or distal end of the balloon catheter or even slightly in front of either end. This allows the cuff to disengage the fronds yet remain attached to the balloon catheter for easy removal from the vessel. In use, these and related embodiments allow the fronds to be held against the balloon to be radially constrained or captured during stent advancement and then easily released before, during or after balloon inflation to deploy the stent at the target site.

In various embodiments, all or a portion of cuff 250 can be fabricated from, silicones, polyurethanes (e.g., PEPAX) and other medical elastomers known in the art; polyethylenes; fluoropolymers; polyolefin; as well as other medical polymers known in the art. Cuff 250 can also be made of heat shrink tubing known in the art such as polyolefin and PTFE heat shrink tubing. These materials can be selected to produce a desired amount of plastic deformation for a selected stress (e.g. hoop stress from the inflation of deployment balloon). In particular embodiments, all or a portion of the materials comprising cuff 250 can be selected to have an elastic limit lower than forces exerted by inflation of the deployment balloon (e.g., the force exerted by 3 mm diameter balloon inflated to 10 atms). Combinations of materials may be employed such that different portions of the cuff (e.g., the proximal and distal sections or the inner and outer surfaces) have differing mechanical properties including, but not limited to, durometer, stiffness and coefficient of friction. For example, in one embodiment the distal portion of the cuff can high a higher durometer or stiffness than a proximal portion of the cuff. This can be achieved by constructing the proximal portion of the cuff from a first material (e.g., a first elastomer) and the distal portion out of a second material (e.g. a second elastomer). Embodiments of the cuff having a stiffer distal portion facilitate maintaining the fronds in a restrained state prior to deployment. In another embodiment, at least a portion of an interior surface of the cuff can include a lubricous material. Examples of suitable lubricious materials include fluoropolymers such as PTFE. In a related embodiment, a portion of the interior of the cuff, e.g., a distal portion, can be lined with lubricous material such as a fluoropolymer. Use of lubricous materials on the interior of the cuff aids in the fronds sliding out from under the cuff during balloon expansion.

Figure 7A:
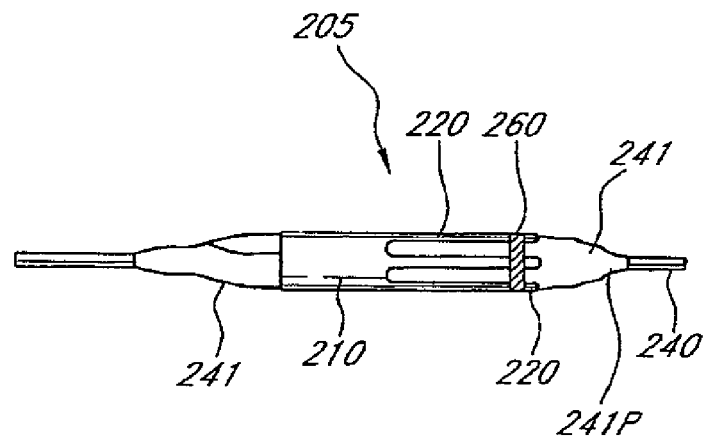
FIGS. 7A-7B are lateral views illustrating an embodiment of a tether for restraining the stent fronds.
Figure 7B:
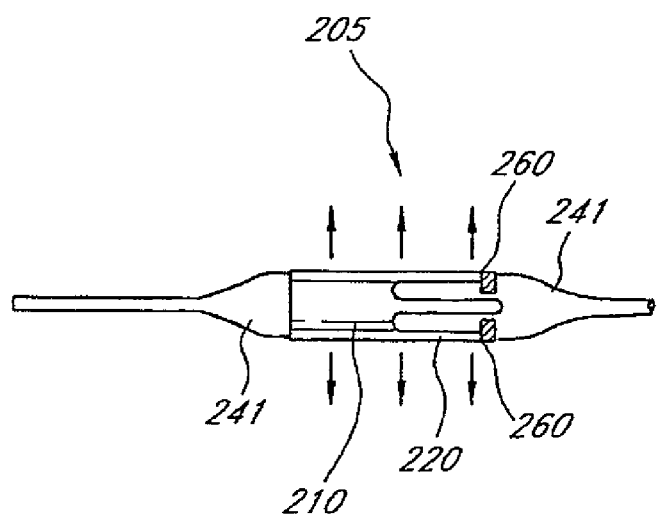

Referring now to FIGS. 7A-7B, in another embodiment for restraining the fronds, a tether 260 can be placed over all or portions of fronds 200 so as to tie the fronds together. Similar to the use of cuff 250, tether 260 can be released by the expansion of the balloon 241. Accordingly, all or a portion of the tether can be configured to plastically deform upon inflation of balloon 241 so as to release the fronds. Alternatively, the tether can be configured to be detached from the fronds prior to expansion of the balloon. In one embodiment, this can be achieved via a pull wire, catheter or other pulling means coupled to the tether directly or indirectly.

In various embodiments, the tether can be a filament, cord, ribbon, etc. which would simply extend around the fronds to capture them like a lasso. In one embodiment the tether can comprise a suture or suture-like material that is wrapped around the fronds. One or both ends of the suture tether can be attachable to a balloon catheter 241. In another embodiment, tether 260 can comprise a band or sleeve that fits over fronds 220 and then expands with expansion of balloon 241. In this and related embodiments, tether 260 can also be attached to balloon catheter 241. Also tether 260 can be scored or perforated so that a portion of the tether shears or otherwise breaks upon balloon inflation, thereby releasing the fronds. Further, the tether 260 can contain a radio-opaque other medical image visible marker 260m to allow the physician to visualize the position of the tether on the fronds, and/or determine if the tether is constraining the fronds.

Figure 8A:
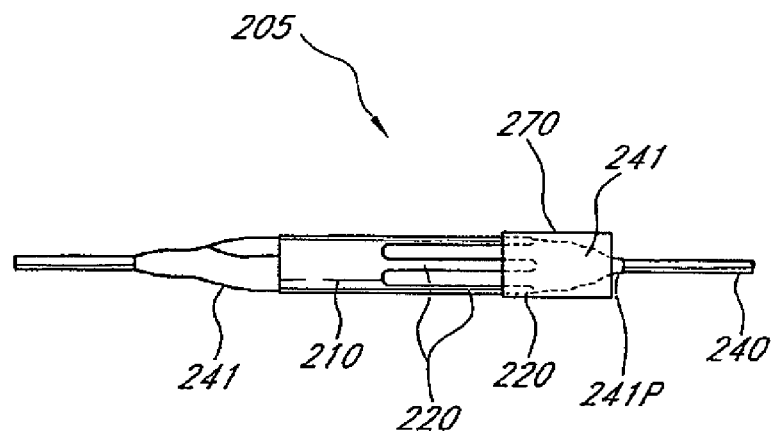
FIGS. 8A-8B are lateral views illustrating an embodiment of a proximally retractable sleeve for restraining the stent fronds.
Figure 8B:
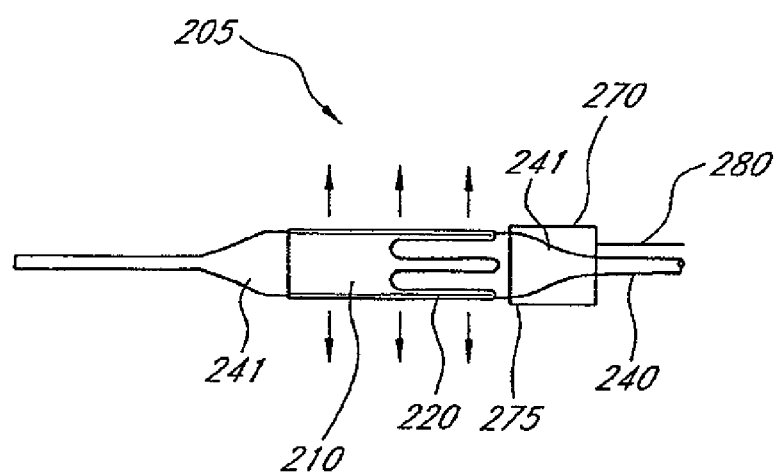

Referring now to FIGS. 8A-8B, in other embodiments of the delivery system 10, the fronds can be constrained through the use of a removable sleeve 270 that can be cover all or a portion of fronds 220 during positioning of the stent at the target tissue site and then be removed prior to deployment of the fronds. In one embodiment, sleeve 270 can be slidably advanced and retracted over stent 210 including fronds 220. Accordingly, all or portions of sleeve 270 can be made from lubricous materials such as PTFE or silicone. Sleeve 270 can also include one or more radio-opaque or other imaging markers 275 which can be positioned to allow the physician to determine to what extent the sleeve is covering the fronds. In various embodiments, sleeve 270 can be movably coupled to catheter 240 such that the sleeve slides over either the outer or inner surface (e.g., via an inner lumen) of catheter 240. The sleeve can be moved through the use of a pull ire, hypotube, stiff shaft or other retraction means 280 known in the medical device arts. In one embodiment, sleeve 270 can comprise a guiding catheter or overtube as is known in the medical device arts.

Figure 9A:
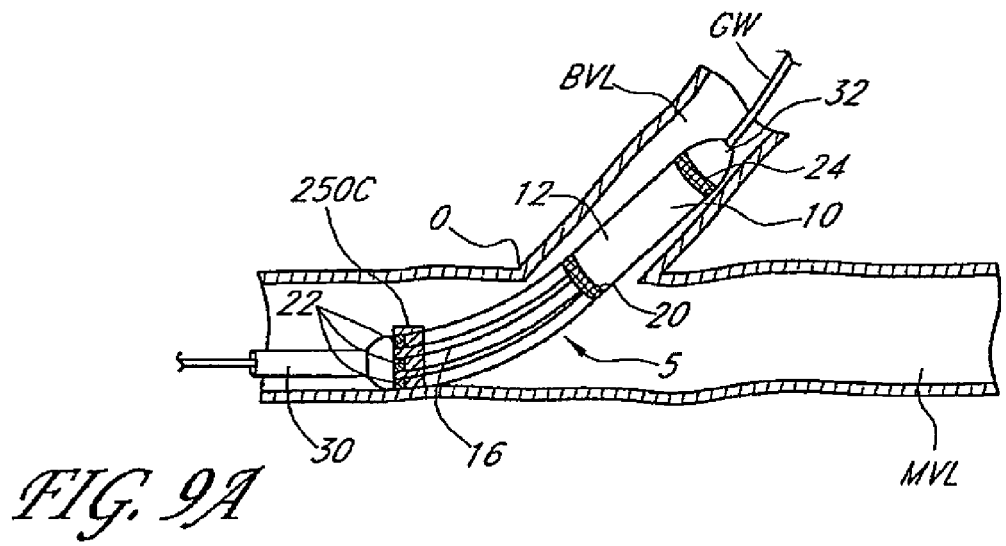
FIGS. 9A-9B, 10A-10B and 11A-11B illustrate deployment of a stent at an Os between a main blood vessel and a side branch blood vessel in accordance with the principles of the methods of the present invention.

Referring now to FIGS. 9A-11B, an exemplary deployment protocol for using delivery system 5 to deliver a prosthesis (10) having a stent region (12) and having one or more fronds (16) will be described. The order of acts in this protocol is exemplary and other orders and/or acts may be used. A delivery balloon catheter 30 is advanced within the vasculature to carry prosthesis 10 having and stent region (12) and fronds 16 to an Os O located between a main vessel lumen MVL and a branch vessel lumen BVL in the vasculature, as shown in FIGS. 9A and 9B. Balloon catheter 30 may be introduced over a single guidewire GW which passes from the main vessel lumen MVL through the Os O into the branch vessel BVL. Optionally, a second guidewire (not shown) which passes by the Os O in the main vessel lumen MVL may also be employed. Usually, the prosthesis 10 will include at least one radiopaque marker 20 on prosthesis 10 located near the transition region between the prosthesis section 12 and the fronds 16. In these embodiments, the radiopaque marker 20 can be aligned with the Os O, typically under fluoroscopic imaging.

Preferably, at least one proximal marker will be provided on the prosthesis at a proximal end of the transition zone, and at least one distal marker will be provided on the prosthesis at the distal end of the transition zone. Two or three or more markers may be provided within the transverse plane extending through each of the proximal and distal ends of the transition zone. This facilitates fluoroscopic visualization of the position of the transition zone with respect to the Os. Preferably, the transition zone is at least about 1 mm and may be at least about 2 mm in axial length, to accommodate different clinical skill levels and other procedural variations. Typically, the transition zone will have an axial length of no more than about 4 mm or 5 mm (for coronary artery applications).

Figure 10A:
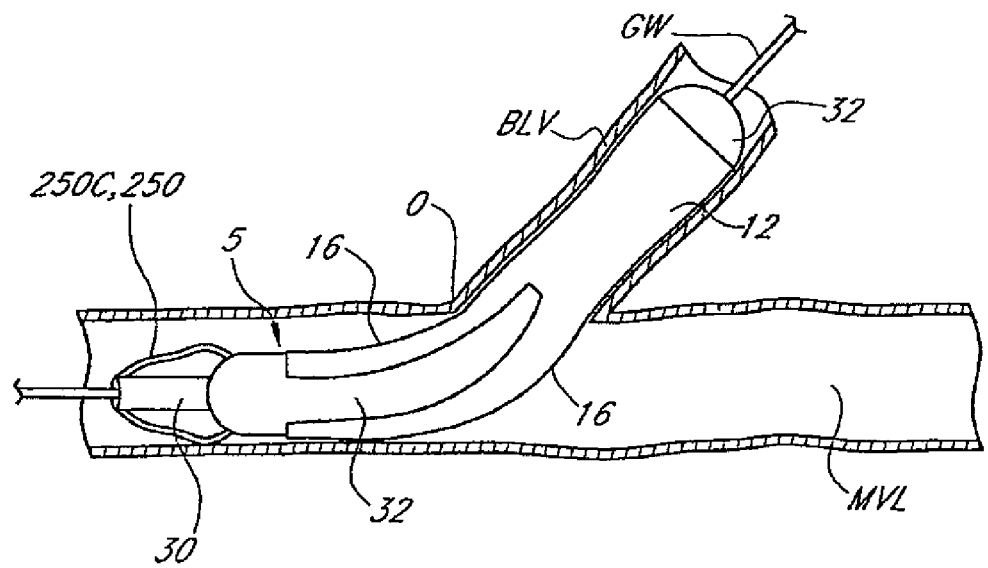
Figure 10B:
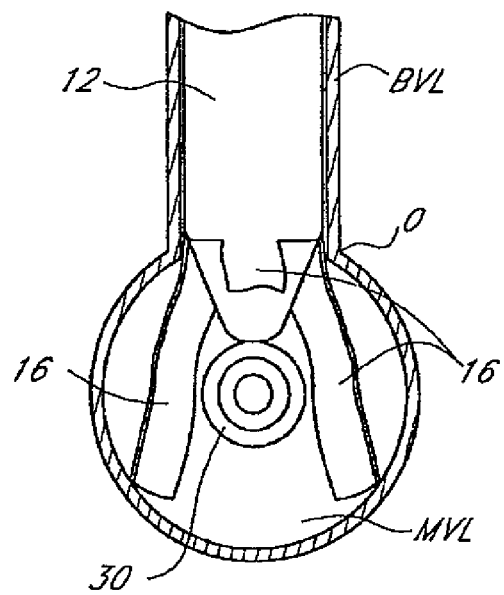

During advancement, the fronds are radially constrained by a constraining means 250c described herein (e.g., a cuff) to prevent divarication of the fronds from the delivery catheter. When the target location is reached at Os O or other selected location, the constraining means 250c is released by the expansion of balloon 32 or other constraint release means described herein (alternatively, the constraining means can be released prior to balloon expansion). Balloon 32 is then further expanded to expand and implant the support region 12 within the branch vessel lumen BVL, as shown in FIGS. 10A and 10B. Expansion of the balloon 32 also partially deploys the fronds 16, as shown in FIGS. 10A and 10B, typically extending both circumferentially and axially into the main vessel lumen MVL. The fronds 16, however, are not necessarily fully deployed and may remain at least partially within the central region of the main vessel lumen MVL. In another embodiment, the constraining means can be released after balloon expansion.

In another embodiment for stent deployment, after deploying stent 10, the cuff or other constraining means 250c need not be removed but can remain in position over at least a portion of the fronds so as to constrain at least the tip of the fronds. See, e.g., FIG. 12A, discussed in additional detail below. Then a main vessel stent 150 is advanced into the main vessel to at least partially overlap the fronds as described above. This method provides a reduced chance that the frond-tips will caught in or on the advancing main vessel stent 150 because the fronds are still captured under the cuff. After placement of stent 150 balloon 32 together the 12 stent portion of the side branch prosthesis is deployed by inflation of 30 balloon. Prosthesis delivery system including cuff 250*c* are removed (by pulling on catheter 30) to release the fronds which when released, spring outward to surround a substantial portion of the circumference of the main vessel stent 150 and the delivery procedures continues as described herein. This approach is also desirable in that by having the cuff left on over the fronds, the frond-tips are constrained together resulting in more advancement of the main vessel stent 150. This in turn can reduce procedure time and increase the accuracy and success rate in placement of the main vessel stent 150 particularly with severely narrowed, eccentric, or otherwise irregularly shaped lesions. In various embodiments, cuff 250*c* and/or proximal end of balloon 32 can have a selectable amount of taper relative to the body of the balloon to facilitate advancement of one or both of the main vessel stent 150 or stent 10 into the target tissue site when one device has already been positioned. Such embodiments also facilitate placement into severely narrowed vessels and/or vessels with irregularly shaped lesions.

Figure 11A:
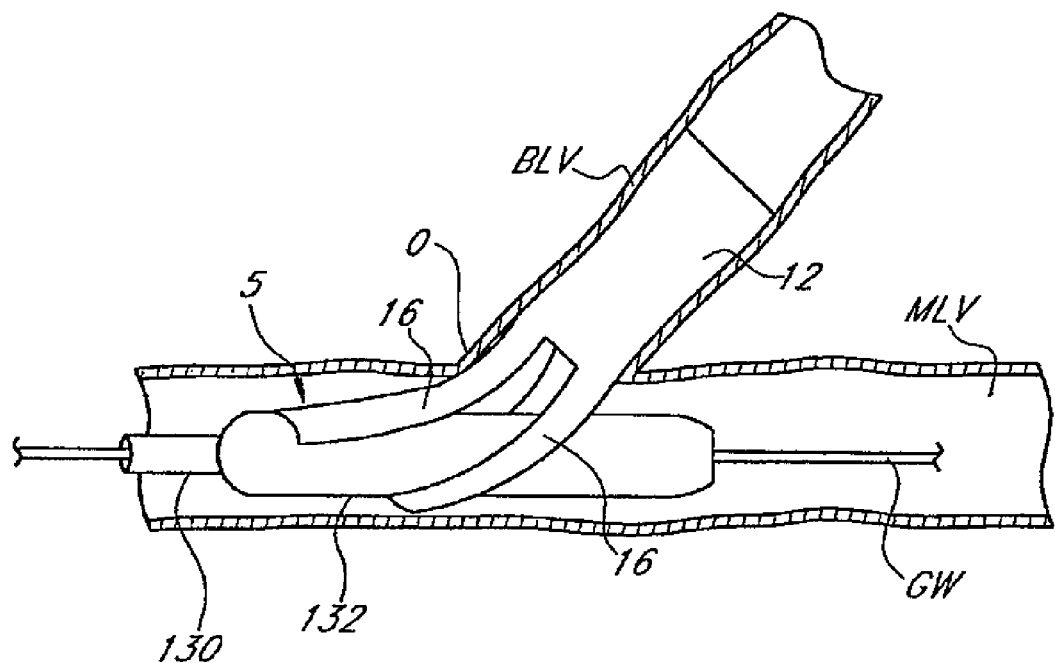
Figure 11B:
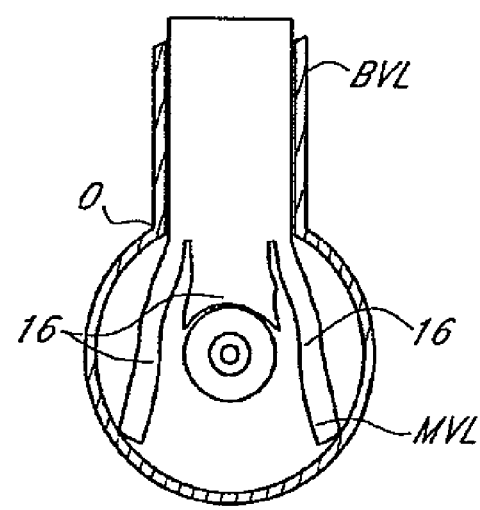

Various approaches can be used in order to fully open the fronds 16. In one embodiment, a second balloon catheter 130 can be introduced over a guidewire GW to position the second balloon 132 within the fronds, as shown in FIGS. 11A and 11B. Optionally, the first catheter 30 could be re-deployed, for example, by partially withdrawing the catheter, repositioning the guidewire GW, and then advancing the deflated first balloon 32 transversely through the fronds 16 and then re-inflating balloon 32 to fully open fronds 16. A balloon which has been inflated and deflated generally does not refold as nicely as an uninflated balloon and may be difficult to pass through the fronds. It will generally be preferable to use a second balloon catheter 130 for fully deforming fronds 16. When using the second balloon catheter 130, a second GW will usually be prepositioned in the main vessel lumen MVL past the Os O, as shown in FIGS. 11A and 11B. Further details of various protocols for deploying a prosthesis having a stent region (12) and fronds or anchors, such as prosthesis 10, are described in co-pending application Ser. No. 10/807,643.

Figure 9B:
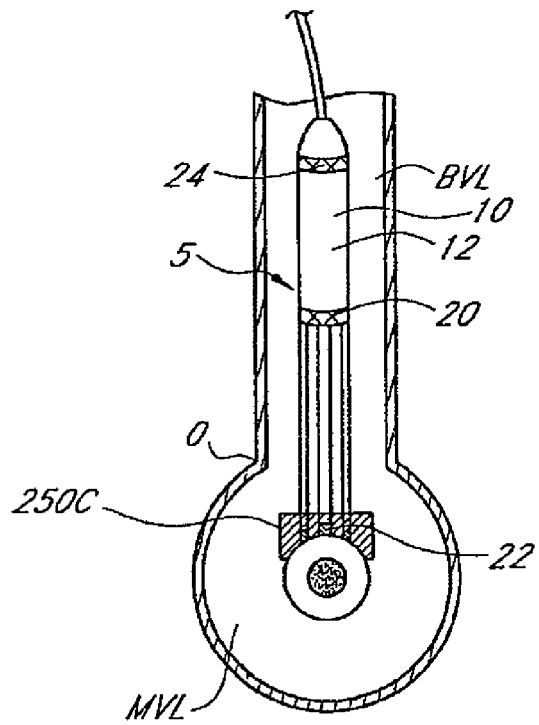

In various embodiments for methods of the invention using prosthesis/delivery system 5, the physician can also make use of additional markers 22 and 24 positioned at the proximal and distal ends of the prosthesis 10. In one embodiment, one or more markers 22 are positioned at the proximal ends of the fronds as is shown in FIGS. 9A and 9B. In this and related embodiments, the physician can utilize the markers to ascertain the axial position of the stent as well as the degree of deployment of the fronds (e.g., whether they are in captured, un-captured or deployed state). For example, in one embodiment of the deployment protocol, the physician could ascertain proper axial positioning of the stent by not only aligning the transition marker 20 with the Os opening O, but also look at the relative position of end markers 22 in the main vessel lumen MVL to establish that the fronds are positioned far enough into the main vessel, have not been inadvertently positioned into another branch vessel/lumen. In this way, markers 20 and 22 provide the physician with a more accurate indication of proper stent positioning in a target location in a bifurcated vessel or lumen.

In another embodiment of a deployment protocol utilizing markers 22, the physician could determine the constraint state of the fronds (e.g. capture or un-captured), by looking at the position of the markers relative to balloon 30 and/or the distance between opposing fronds. In this way, markers 22 can be used to allow the physician to evaluate whether the fronds were properly released from the constraining means prior to their deployment. In a related embodiment the physician could determine the degree of deployment of the fronds by looking at (e.g., visual estimation or using Quantitative Coronary Angiography (QCA)) the transverse distance between markers 22 on opposing fronds using one or medical imaging methods known in the art (e.g., fluoroscopy). If one or more fronds are not deployed to their proper extent, the physician could deploy them further by repositioning (if necessary) and re-expanding balloon catheters 30 or 130.

Figure 12A:
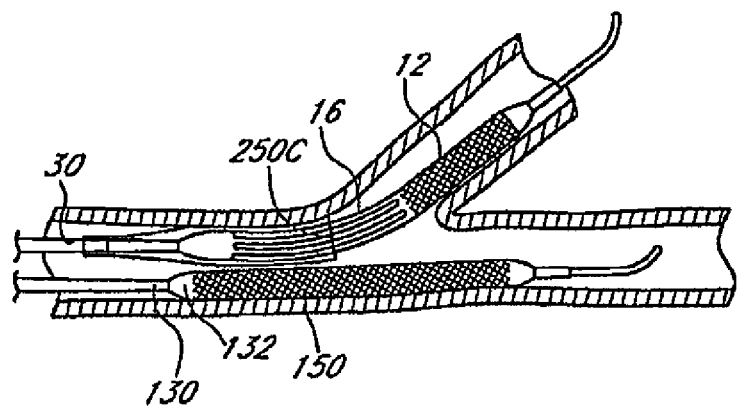
FIGS. 12A-12H are lateral and cross section views illustrating deployment of a stent having filament fronds an Os between a main blood vessel and a side branch blood vessel in accordance with the principles of the methods of the present invention.

Referring now to FIG. 12A-12I, an exemplary and embodiment of a deployment protocol using a deployment system 5 having a prosthesis 10 with fronds 16 will now be presented. As shown in FIG. 12A, prosthesis 10 is positioned at Os opening O with catheter 30 such that the stent section 12 is positioned substantially in branch vessel BV with the fronds 16 extending into the Os O and in the main vessel lumen MVL. In this embodiment a second delivery catheter 130 containing a stent 150 has been positioned in the MVL prior to positioning of catheter 30. Alternatively, catheter 130 can be positioned first and the branch vessel catheter 30 subsequently. In embodiments where catheter 130 has been positioned first, the proximal end of catheter 30 including fronds 16 can be positioned adjacent a proximal portion of balloon 132 of catheter 130 such that portions of captured fronds 16 and stent 150 are positioned side by side. Such alignment can be facilitated by lining up one or more radio-opaque markers (described herein) on the two catheters.

Figure 12B:
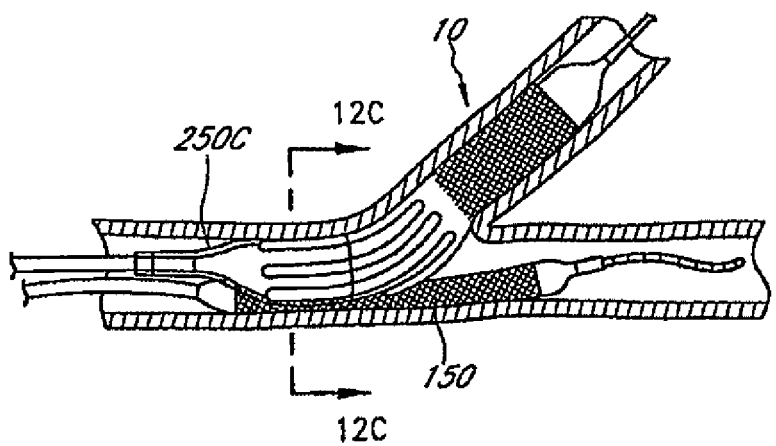
Figure 12C:
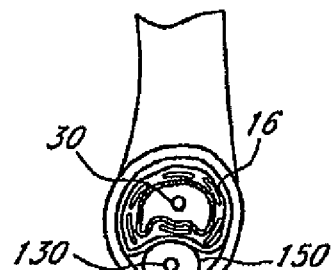
Figure 12D:
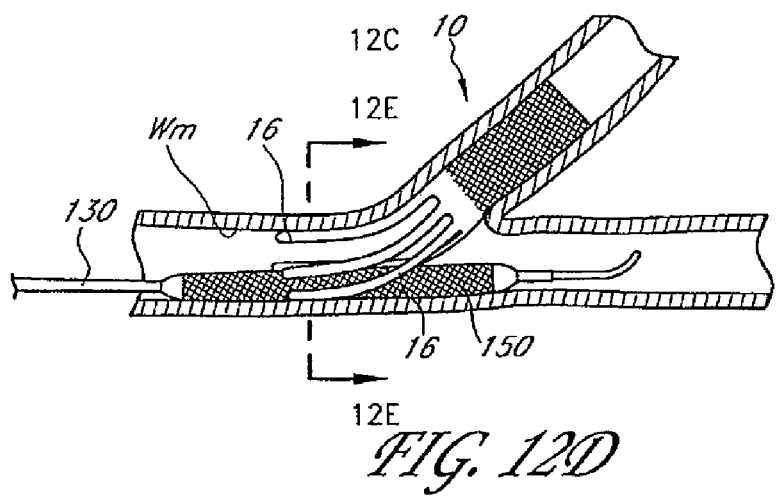
Figure 12E:
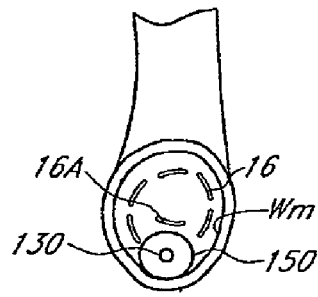

Next, as shown in FIGS. 12B-12C, balloon 32 of catheter 30 is expanded. Then as shown in FIGS. 12D-12E, catheter 30 together with cuff 250*c* is withdrawn from the vessel to uncover and release the fronds 16. When deployed, the fronds 16 are positioned between the vessel wall and stent 150 and substantially surround at least a portion of the circumference of the main vessel stent 150C/delivery system (130) as well as making contact with a substantial portion of inner wall Wm of main vessel lumen MVL. Preferably as shown in FIG. 12E, the fronds are distributed around the circumference of the Wall Wm. Also as shown in FIG. 12E one of the fronds 16A may bent back by stent 150, but may not be contacting the vessel wall.

Figure 12F:
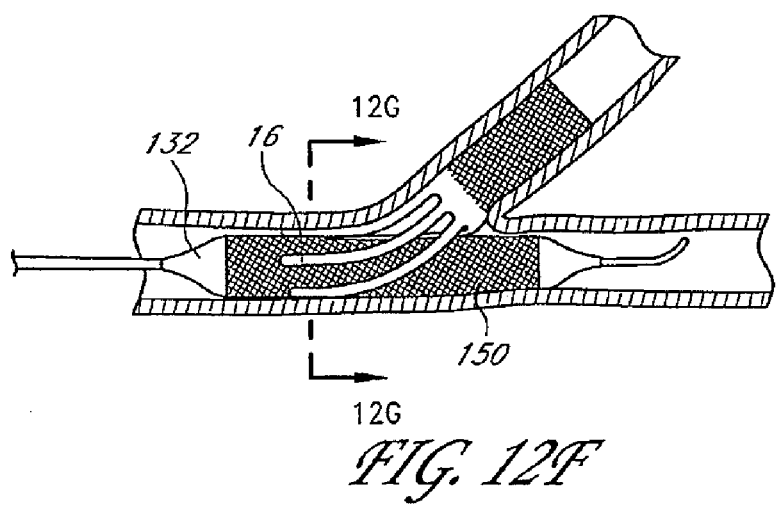
Figure 12G:
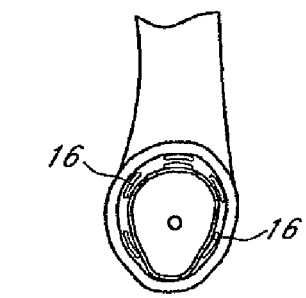
Figure 12H:
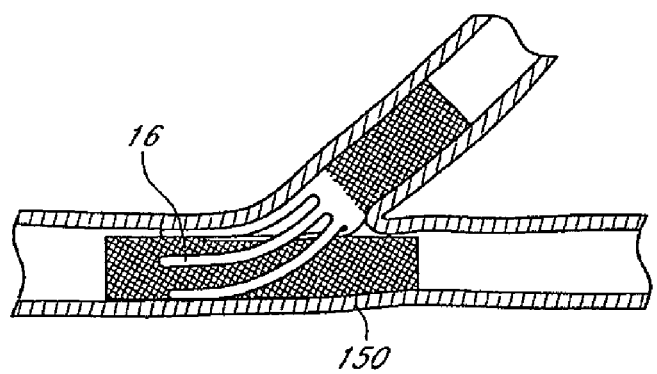

Then, as shown in FIGS. 12F-12H, balloon 132 is expanded to expand and deploy stent 150 after which the balloon is deflated and catheter 130 is withdrawn. Expansion of stent 150 serves to force and hold fronds 16 up against the vessel wall in a circumferential pattern as is shown in FIG. 12G. This essentially fixes the fronds in place between expanded stent 150 and the vessel wall. As such, the fronds may serve five functions, first, as an anchoring means to hold stent 12 in place in the branch vessel lumen BVL. Second they serve as a mechanical joining means to mechanically join stent 12 to stent 150. Third, to provide stent coverage to prevent prolapse of tissue into the lumen as well as in the case of a drug coated stent to deliver agent. Finally, they also provide additional mechanical prosthesising (hoop strength) to hold open Os of the branch vessel. More specifically, the now fixed fronds 16 can be configured to serve as longitudinal struts to more evenly distribute expansion forces over a length of the vessel wall as well as distribute compressive forces over a length of stent 12.

The prosthesis of the present invention, may be utilized in combination with either main vessel stents having a substantially uniform wall pattern throughout, or with main vessel stents which are provided with a wall pattern adapted to facilitate side branch entry by a guidewire, to enable opening the flow path between the main vessel and the branch vessel. Three examples of suitable customized stent designs are illustrated in FIG. 13A through 13C. In each of these constructions, a main vessel stent 110 contains a side wall 112 which includes one or more windows or ports 114. Upon radial expansion of the stent 110, the port 114 facilitates crossing of a guide wire into the branch lumen through the side wall 112 of the main vessel stent 110. A plurality of ports 114 may be provided along a circumferential band of the main vessel stent 110, in which instance the rotational orientation of the main vessel stent 110 is unimportant. Alternatively, as illustrated, a single window or port 114 may be provided on the side wall 112. In this instance, the deployment catheter and radiopaque markers should be configured to permit visualization of the rotational orientation of the main vessel stent 110, such that the port 114 may be aligned with the branch vessel.

In general, the port 114 comprises a window or potential window through the side wall which, when the main vessel stent 110 is expanded, will provide a larger window than the average window size throughout the rest of the stent 110. This is accomplished, for example, in FIG. 13A, by providing a first strut 116 and a second strut 118 which have a longer axial distance between interconnection than other struts in the stent 110. In addition, struts 116 and 118 are contoured to provide a first and second concavity facing each other, to provide the port 114.

Referring to FIG. 13B, the first strut 116 and second strut 118 extend substantially in parallel with the longitudinal axis of the stent 110. The length of the struts 116 and 118 is at least 2 times, and, as illustrated, is approximately 3 times the length of other struts in the stent. Referring to FIG. 13C, the first and second struts 116 and 118 are provided with facing concavities as in FIG. 13A, but which are compressed in an axial direction. Each of the foregoing configurations, upon expansion of the main vessel stent 110, provide an opening through which crossing of a guidewire may be enhanced. The prosthesis of the present invention may be provided in kits, which include a prosthesis mounted on a balloon catheter as well as a corresponding main vessel stent mounted on a balloon catheter, wherein the particular prosthesis and main vessel stent are configured to provide a working bifurcation lesion treatment system for a particular patient. Alternatively, prostheses in accordance with the present invention may be combined with separately packaged main vessel stents from the same or other supplier, as will be apparent to those of skill in the art.

Figure 13D:
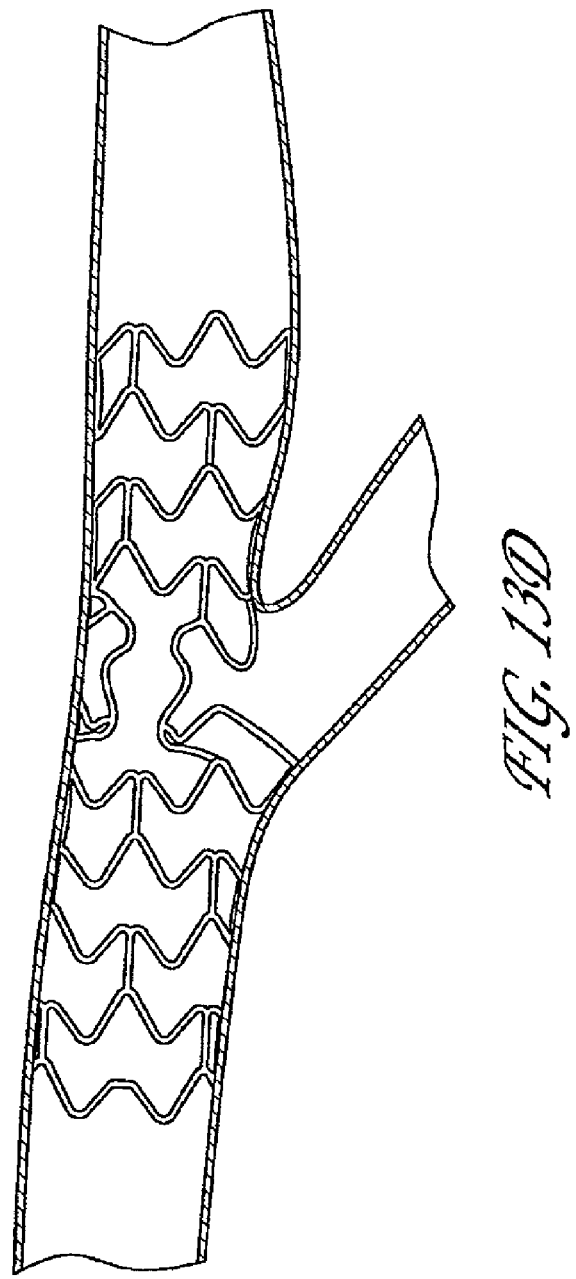
FIG. 13D is an image of a deployed main vessel stent having a side wall opening in alignment with a branch vessel.

FIG. 13D is an image of a main vessel stent having a side opening, deployed such that the side opening is aligned with the branch vessel lumen.

In accordance with a further aspect of the present invention, there is provided a stepped balloon for use with the prosthesis disclosed herein. The stepped balloon may be utilized for the initial implantation of the prosthesis, or for reconfiguring a previously implanted prosthesis as will be apparent to those of skill in the art.

Figure 15:
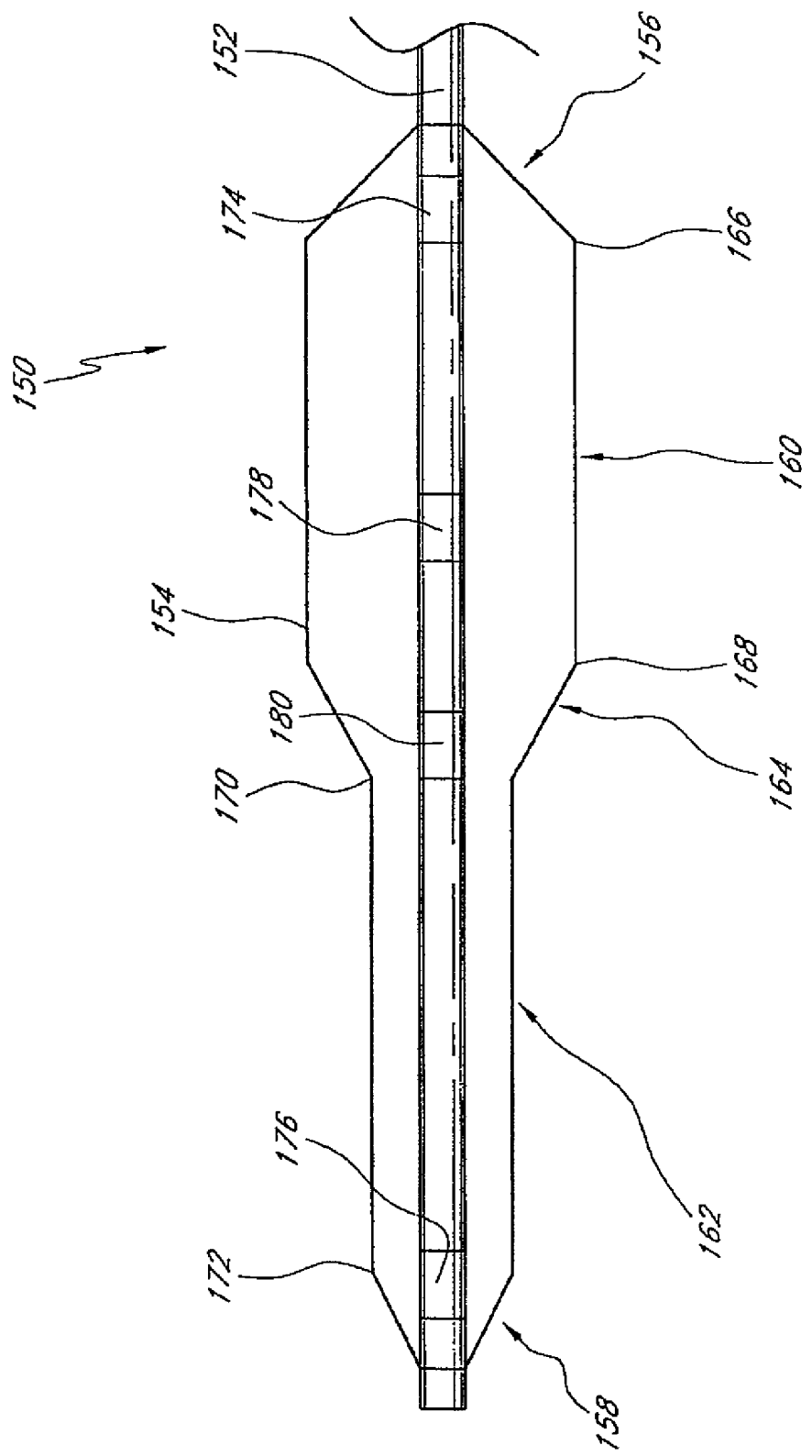
FIG. 15 is a schematic profile of a stepped balloon in accordance with one aspect of the present invention.

Referring to FIG. 15, there is illustrated a schematic side view of a distal end section of a catheter 150 having an elongate flexible tubular shaft 152 with a stepped balloon 154 mounted thereon. The dimensions, materials and construction techniques for the catheter shaft 152 are well understood in the art, and discussed briefly elsewhere herein. In general, shaft 152 has an axial length sufficient to reach from the desired percutaneous access point to the treatment site, and will typically include at least one inflation lumen for placing the stepped balloon 154 in fluid communication with a source of inflation media, as well as a guidewire lumen for either over the wire or rapid exchange guidewire tracking.

The stepped balloon 154 extends between a proximal end 156 and distal end 158. The balloon 154 is necked down to the catheter shaft 152 at each of the proximal and distal ends, and secured to the shaft 152 using any of a variety of adhesives, thermal bonding, or other techniques well known in the art.

The stepped balloon is provided with a proximal zone 160 and a distal zone 162, separated by a transition zone 164. In the illustrated embodiment, the proximal zone 160 has a greater inflated diameter than the distal zone 162. Alternatively, the relative dimensions may be reversed, such that the distal zone 162 has a greater inflated diameter than the proximal zone 160, such as for use in a retrograde catheterization from the branch vessel into the main vessel.

The diameters and lengths of the proximal zone 160 and distal zone 162 may be varied considerably, depending upon the intended target site. In an implementation of the invention designed for use in the coronary artery, a proximal zone 160 may be provided with a diameter in the range of from about 3 mm to about 4 mm, and the distal zone 162 may have an inflated diameter in the range of from about 2 mm to about 3 mm. In one implementation of the invention, the proximal zone 160 has an inflated diameter of about 3.5 mm and the distal zone 162 has an inflated diameter of about 2.5 mm. In general, the inflated diameter of the proximal zone 160 will be at least 110% of the inflated diameter of the distal zone 162. In certain implementations of the invention, the inflated diameter of the proximal zone 160 will be at least 125% of the inflated diameter of the distal zone 162.

The proximal zone 160 has a working length defined as the axial length between a proximal shoulder 166 and a distal shoulder 168. The working length of the proximal zone 160 is generally within the range of from about 5 to about 30 mm, and, in one embodiment, is about 9 mm. The working length of the distal zone 162 extends from a proximal shoulder 170 to a distal shoulder 172. The working length of the distal zone 162 is generally within the range of from about 5 to about 20 mm, and, in one embodiment, is about 6 mm. In the illustrated embodiment, each of the proximal zone 160 and distal zone 162 has a substantially cylindrical inflated profile. However, noncylindrical configurations may also be utilized, depending upon the desired clinical result.

The configuration and axial length of the transition zone 164 may be varied considerably, depending upon the desired frond configuration and ostium coverage characteristics of the implanted prosthesis. In the illustrated embodiment, the transition zone 164 comprises a generally frustoconical configuration, having an axial length between proximal shoulder 170 of the distal zone 162 and distal shoulder 168 of the proximal zone 160 within the range of from about 1 to about 10 mm, and, in one embodiment, about 2.5 mm.

The transition zone of this balloon delineates the transition from one diameter to another. In one embodiment this transition zone may be 4 mm in length and ramp from 2.5 to 3.5 mm in diameter. This conical surface is used to mold or flare the ostium of the bifurcation from the smaller side branch to the larger main vessel. In this configuration this stepped balloon may be utilized for deploying the prosthesis. Used in this manner the leading and trailing surfaces are utilized to expand the device in the side branch and main vessel and the transition zone is used to flare the transition zone of the stent against the wall of the ostium.

The wall of the stepped balloon 154 may comprise any of a variety of conventional materials known in the angioplasty balloon arts, such as any of a variety of nylons, polyethylene terephthalate, various densities of polyethylene, and others known in the art. Material selection will be influenced by the desired compliancy and burst strength of the balloon, as well as certain manufacturing considerations.

The stepped balloon may be formed in accordance with techniques well known in the angioplasty arts. For example, stock tubing of the desired balloon material may be inflated under the application of heat within a Teflon lined capture tube having the desired stepped configuration. The proximal and distal ends may thereafter be axially stretched with the application of heat to neck down to a diameter which relatively closely fits the outside diameter of the elongate shaft 152.

Figure 16:
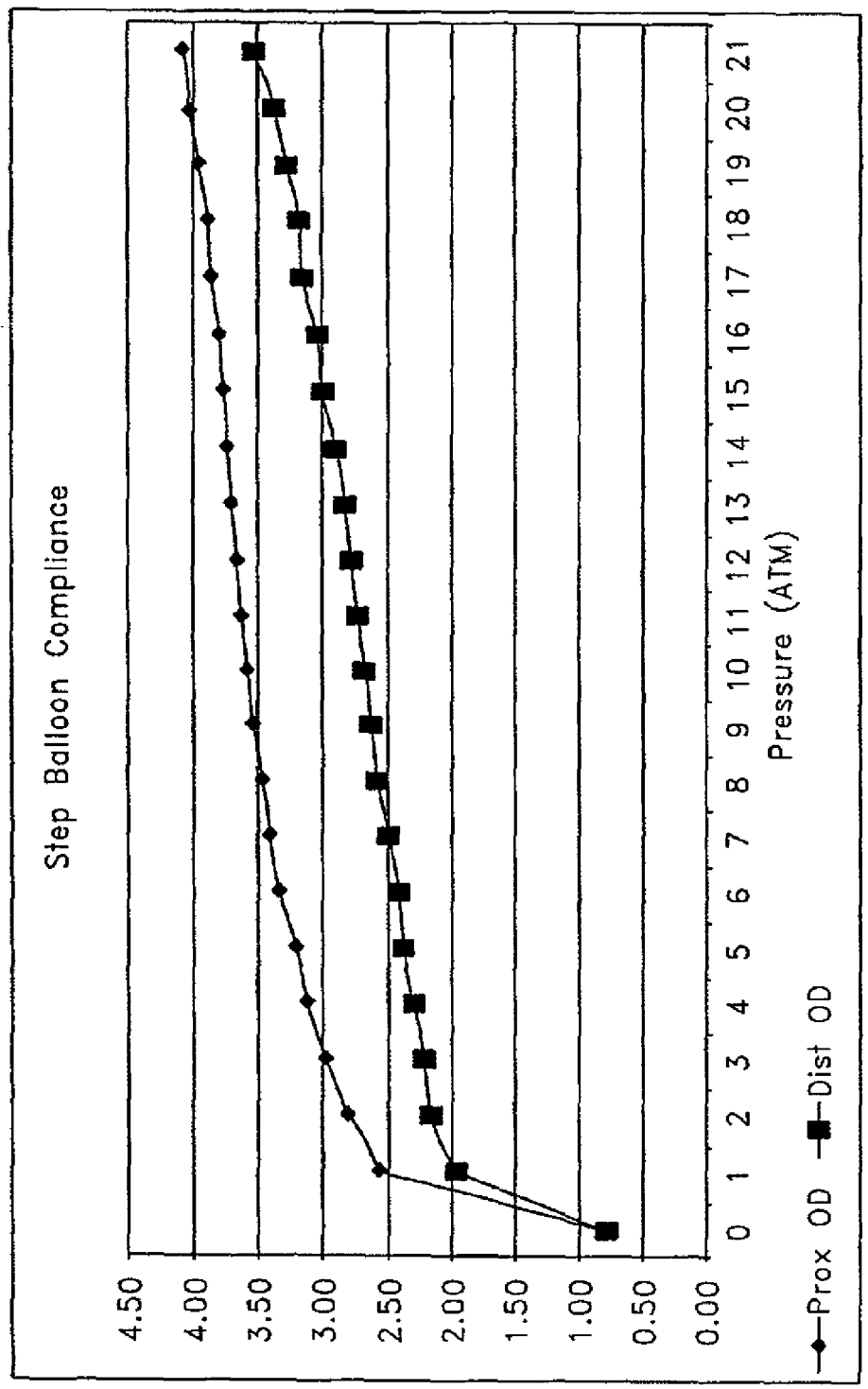
FIG. 16 is a balloon compliance curve for one embodiment of the stepped balloon in accordance with the present invention.

The balloon may be constructed such that it assumes the inflated stepped configuration at a relatively low inflation pressure. See, e.g., an exemplary compliance curve in FIG. 16. Alternatively, the balloon may be configured for sequential expansion, such as by allowing the distal zone 162 to inflate to its final outside diameter at a first pressure, to firmly position the branch vessel stent, and the proximal zone 160 only inflates to its final diameter at a second, higher inflation pressure, where a sequential deployment of the implant is desired.

In one embodiment the balloon is constructed such that it assumes the inflated stepped configuration upon inflation and retains this shape throughout its inflated working range (from initial inflation to rated burst pressure.) In this embodiment the balloon working range is from 1 ATM to 16 ATM at rated burst pressure.

In another embodiment the balloon is constructed such that it initially assumes the inflated stepped configuration within the lower pressures of its working range and trends to the same diameter at the higher pressures. The diameter of this balloon at higher pressure approximates that of the larger diameter in the stepped configuration.

In another embodiment the balloon is constructed such that it initially has a single diameter during the initial lower pressures of its working range and assumes its inflated stepped configuration at higher pressures. The diameter of the balloon at lower pressure approximates that of the smaller diameter in the stepped configuration.

Alternatively, the function of the stepped balloon 154 may be accomplished by providing two distinct balloons, 160' and 162'. The proximal balloon 160' may be inflated by a first inflation lumen (not illustrated) and the distal balloon 162' may be inflated by a second inflation lumen (not illustrated) extending throughout the length of the catheter shaft, to separate inflation ports. Inflation may be accomplished simultaneously or sequentially, depending upon the desired clinical procedure. Alternatively, a proximal balloon 160' and a distal balloon 162' may be both inflated by a single, common inflation lumen extending throughout the length of the catheter shaft.

The stepped balloon 154 is preferably navigated and positioned within the vascular system under conventional fluoroscopic visualization. For this purpose, the catheter 150 may be provided with at least one radiopaque marker. In the illustrated embodiment, a first radiopaque marker 174 is provided on the catheter shaft 152, at about the proximal shoulder 166. At least a second radiopaque marker 176 is provided on the shaft 152, aligned approximately with the distal shoulder 172. Proximal marker 174 and distal marker 176 allow visualization of the overall length and position of the stepped balloon 154.

In addition, a first transition marker 178 and second transition marker 180 may be provided on the shaft 152, at a location corresponding to a transition zone on the prosthesis. Transition markers 178 and 180 thus enable the precise location of the prosthesis transition with respect to the ostium between the main vessel and branch vessel, as has been discussed elsewhere herein. Each of the markers may comprise a band of gold, silver or other radiopaque marker materials known in the catheter arts.

In one embodiment of the stepped balloon 154 intended for use in the coronary artery, the axial length of the balloon between the proximal marker 174 and distal marker 176 is approximately 19.5 mm. The length between the distal marker 176 and transition marker 180 is approximately 6.1 mm. The distance between the transition markers 178 and 180, including the length of the transition markers, is about 4.5 mm. As will be apparent to those of skill in the art other dimensions may be utilized, depending upon the dimensions of the prosthesis and the target anatomy.

Figure 17:
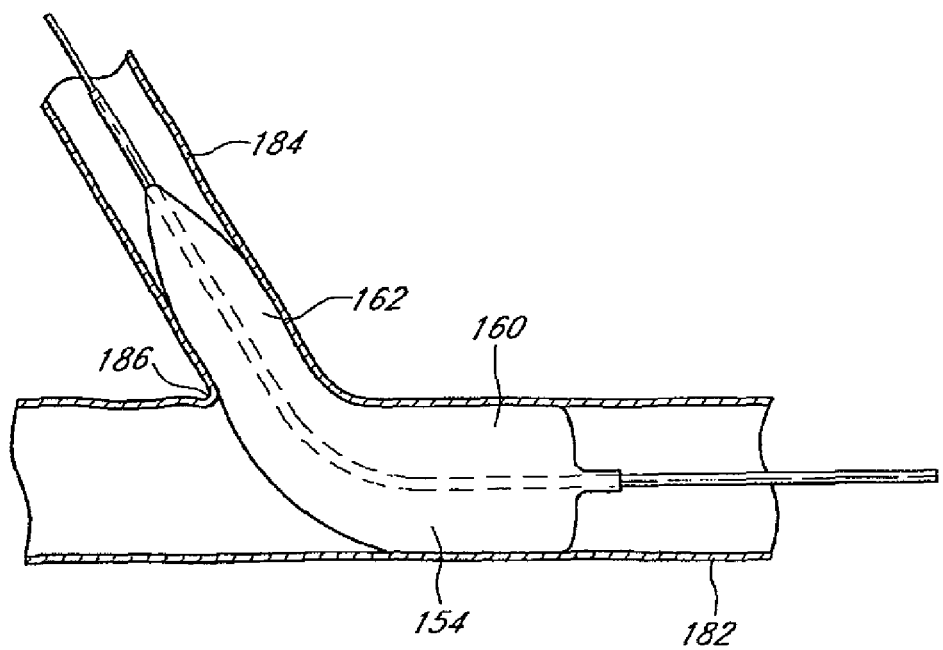
FIG. 17 is a schematic representation of a stepped balloon positioned within a vascular bifurcation.
Figure 18:
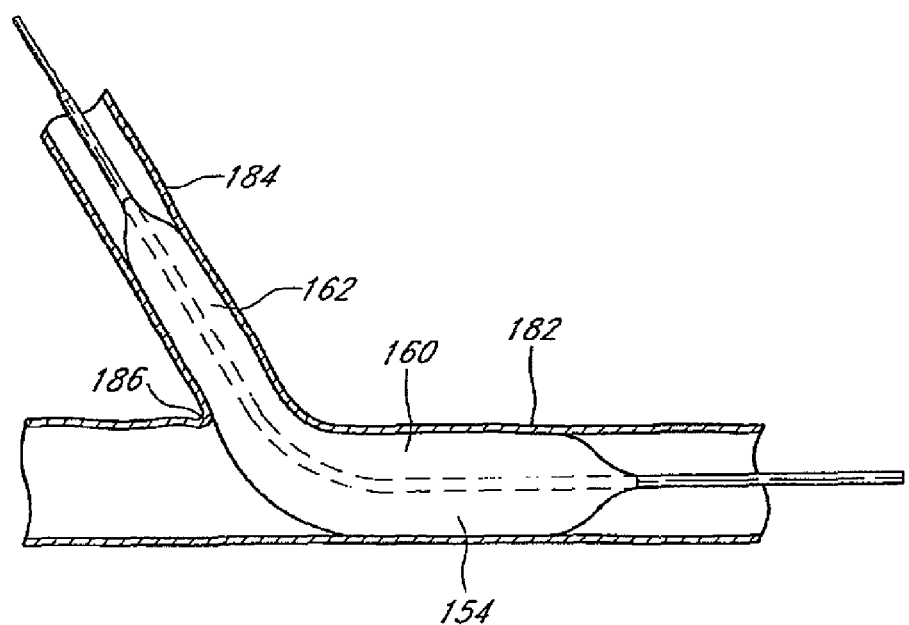
FIG. 18 is a schematic representation as in FIG. 17, with a different configuration of stepped balloon in accordance with the present invention.

Referring to FIGS. 17 and 18, there is schematically illustrated two different configurations of a stepped balloon 154 in accordance with the present invention, positioned and inflated within a treatment site at a vascular bifurcation, with the prosthesis omitted for clarity. In each, a stepped balloon 154 is positioned such that a proximal zone 160 is inflated within a main vessel 182. A distal zone 162, having a smaller inflated diameter than proximal zone 160, is positioned within the branch vessel 184. The stepped balloon 154 has been positioned to illustrate the relative location of the transition markers 178 and 180, with respect to the carina 186 of the bifurcation.

Figure 19:
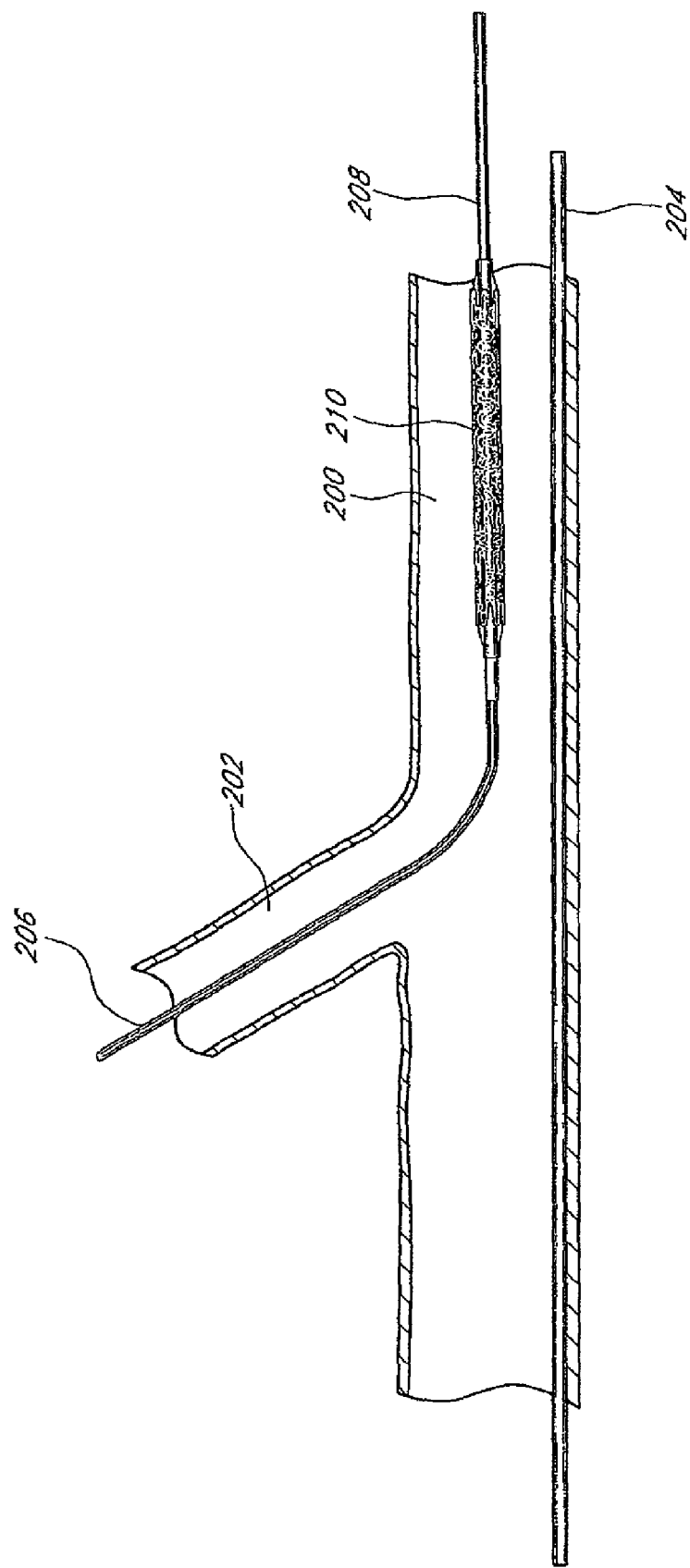
FIG. 19 is a first step in a deployment sequence using a stepped balloon and prosthesis in accordance with the present invention.

FIGS. 19 through 22 illustrate one application of the stepped balloon and prosthesis in accordance with the present invention. Referring to FIG. 19, there is illustrated a bifurcation between a main vessel 200 and a branch vessel 202. A main vessel guidewire 204 is illustrated as positioned within the main vessel, and a branch vessel guidewire 206 is in position extending from the main vessel 200 into the branch vessel 202.

A balloon catheter 208 carrying a prosthesis 210 is advancing along the branch vessel guidewire 206.

Figure 20:
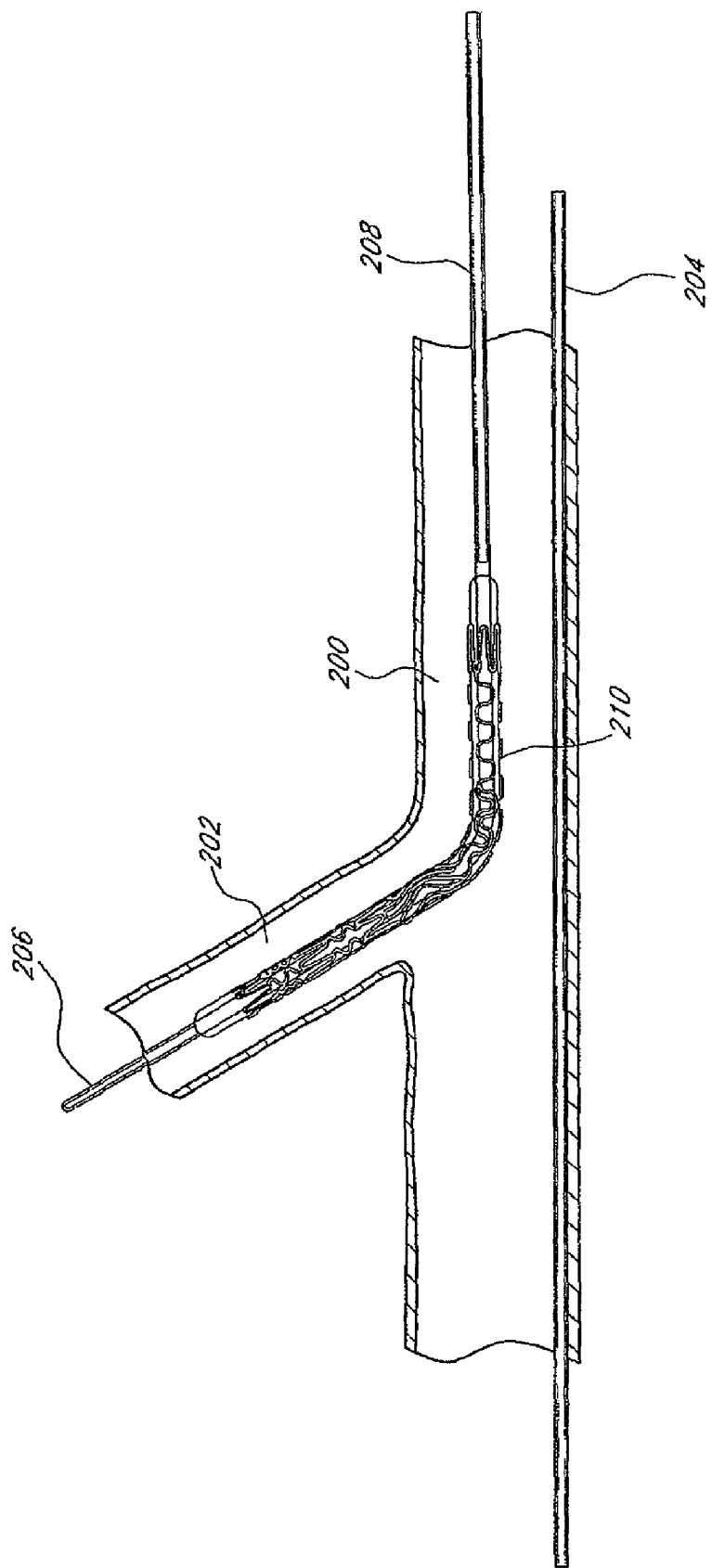
FIG. 20 is a second step in the deployment process disclosed in connection with FIG. 19, in which the prosthesis is positioned across the Os.

Referring to FIG. 20, the catheter 208 has advanced to the point of positioning the prosthesis 210 across the ostium between the main vessel 200 and branch vessel 202.

Referring to FIG. 21, a stepped balloon 212 carried by the catheter 208 has been inflated across the ostium into the branch vessel 202. FIG. 22 illustrates the implanted prosthesis 210, after the balloon catheter 208 has been proximally retracted.

As can be seen from FIGS. 21 and 22, dilation of the stepped balloon 212 across the ostium enables expansion of the distal zone of the prosthesis in the branch vessel, the proximal zone of the prosthesis in the main vessel, and a transition zone of the prosthesis spans the ostium. The main vessel guidewire 204 may thereafter be proximally retracted to a point proximal to the prosthesis 212, and distally advanced through the proximal portion and the fronds of the prosthesis. A main vessel stent may thereafter be positioned in the main vessel 200 as has been discussed elsewhere herein.

Referring to FIGS. 23 and 24, there is illustrated a schematic representation of a distal portion of a stepped balloon catheter in accordance with the present invention. In general, the catheter includes a primary guidewire lumen as is understood in the art, such as for tracking the guidewire which extends into the branch vessel. Unlike previous embodiments disclosed herein, the catheter of FIGS. 23 and 24 includes a secondary guidewire lumen, such as for tracking the guidewire which extends into the main vessel lumen beyond the bifurcation.

Referring to FIG. 23, a catheter 220 extends between a proximal end 222 (not shown) and a distal end 224. A balloon 226 is carried in vicinity of the distal end 224, as is known in the balloon catheter arts. Balloon 226 may comprise a stepped balloon as has been described elsewhere herein, or a tapered balloon, or a conventional cylindrical angioplasty or stent deployment balloon, depending upon the desired performance.

The catheter 220 includes a guidewire lumen 228 which extends throughout the length of at least a distal portion of the catheter 220, to a distal port 230 at the distal end 224 of the catheter 220. In an embodiment intended for over-the-wire functionality, the first guidewire lumen 228 extends proximally throughout the length of the catheter, to a proximal manifold. In an alternate configuration intended for rapid exchange functionality, a proximal access port (not shown) provides access to the first guidewire lumen 228 at a point along the length of the catheter distal to the proximal end 222. In general, rapid exchange proximal access ports may be within the range of from about 10 cm to about 30 cm from the distal end 224.

As can be seen with reference to, for example, FIG. 23A, the catheter 220 is additionally provided with an inflation lumen 232 which extends throughout the length of the catheter to the proximal end 222. The distal end of inflation lumen 232 is in communication via an inflation port 234 with the interior of the balloon 226, to enable placement of the balloon 226 in fluid communication with a source of inflation media.

Referring to FIG. 23B, the catheter 220 is additionally provided with a second guidewire lumen 236. Second guidewire lumen 236 extends between a proximal access port 238 and a distal access port 240. The distal access port 240 is positioned proximally to the distal end 224 of the catheter 220. In the illustrated embodiment, the distal port 240 is positioned on the proximal side of the balloon 226. Generally, the distal port 240 will be no greater than about 4 cm, and often no greater than about 2 cm proximal of the balloon 226.

The proximal access port 238 may be provided on the side wall of the catheter, such as within the range of from about 10 cm to about 60 cm from the distal end 224. In one embodiment, the proximal access port 238 is within the range of from about 25 cm to about 35 cm from the distal end 224. The proximal port 238 is preferably spaced distally apart from the proximal end 222 of the catheter 220, to enable catheter exchange while leaving the main vessel guidewire in place as will be apparent in view of the disclosure herein.

As illustrated in FIG. 23, the second guidewire lumen 236 may be formed as an integral part of the catheter body. This may be accomplished by providing an initial 3 lumen extrusion having the desired length, and trimming away the wall of the second guidewire lumen 236 distally of the distal port 240 and proximally of the proximal port 238.

Alternatively, the second guidewire lumen 236 may be separately attached to a conventional catheter shaft such as is illustrated in FIG. 24. In this construction, the second guidewire lumen 236 is defined within a tubular wall 237, which may be a separate single lumen extrusion. The tubular wall 237 is positioned adjacent the catheter shaft, and bonded thereto using any of a variety of techniques known in the art, such as thermal bonding, adhesives, solvent bonding or others. Superior bonding and a smooth exterior profile may also be achieved by placing a shrink tube around the assembly of the catheter 220 and tubular wall 237, and heating the shrink tube to shrink around and combine the two structures as is well understood in the catheter manufacturing arts. It may be desirable to place a mandrel within the second guidewire lumen 236 and possibly also the first guidewire lumen 228 and inflation lumen 232 during the heat shrinking process.

Figure 25:
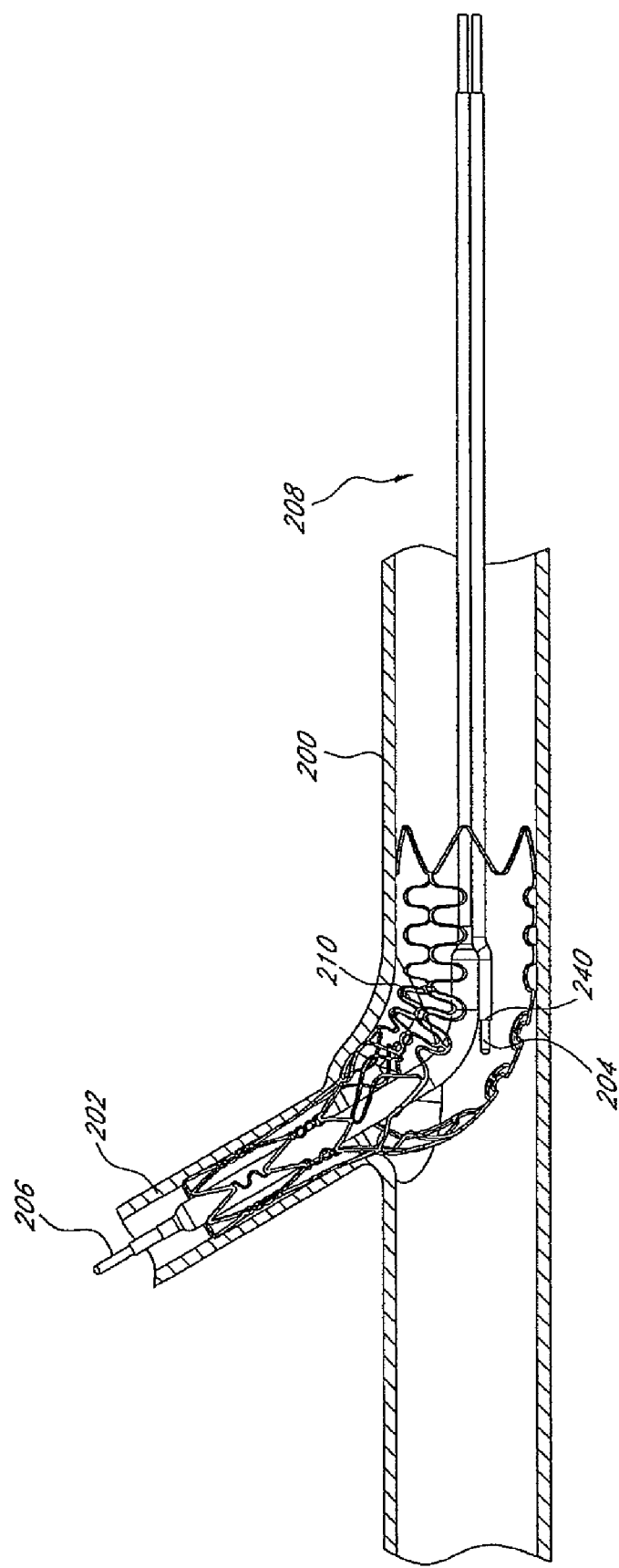
FIG. 25 is a schematic view of a two guidewire catheter in accordance with the present invention, in position at a vascular bifurcation.

In use, the second guidewire lumen 236 enables control over the main vessel guidewire. Referring to FIG. 25, there is illustrated a two guidewire catheter 208 in position across a bifurcation from a main vessel 200 into a branch vessel 202. The branch vessel guidewire 206 has been positioned in the branch vessel 202, and the catheter 208 advanced into position over the wire into the bifurcation. The prosthesis 210 is illustrated in its expanded configuration, and the balloon has been deflated.

Prior to percutaneously introducing the catheter into the patient's vasculature, the main vessel guidewire 204 is positioned within the secondary guidewire lumen 236, and the catheter and main vessel guidewire assembly is advanced as a unit along the branch vessel guidewire to the treatment site.

As seen in FIG. 25, the distal exit port 240 of the secondary guidewire lumen 236 is aligned such that the main vessel guidewire 204 is aimed down the lumen of the main vessel 200. In the illustrated embodiment, the secondary guidewire lumen is attached to the outside of the step balloon. The stent is crimped onto the step balloon, and the exit of the secondary guidewire lumen is between the intermediate zone and the circumferentially extending link of the prosthesis. In the crimped configuration, the distal exit 240 of the secondary lumen 236 resides between two adjacent fronds.

Following deployment of the stent and deflation of the balloon as illustrated in FIG. 25, the main vessel guidewire 204 may be distally advanced into the main vessel beyond the bifurcation, in between the two adjacent fronds. See, FIG. 26.

Referring to FIG. 27, there is illustrated an embodiment similar to FIG. 25, except that the distal exit port 240 of the main vessel guidewire lumen 236 is positioned proximally of the balloon. The precise location of the distal exit 240 may be varied, so long as it permits direction of the main vessel guidewire distally within the main vessel beyond the bifurcation. In general, the distal exit 240 may be located within the axial length of the prosthesis as mounted on the catheter.

Following distal advance of the main vessel guidewire 204 into the main vessel distally of the bifurcation, the catheter 208 may be proximally withdrawn from the treatment site leaving the main vessel guidewire 204 in place. The catheter 208 may be removed from the main vessel guidewire 204 as is understood in the rapid exchange catheter practices, and a secondary catheter may be advanced down the main vessel guidewire such as to dilate an opening between the fronds into the main vessel beyond the bifurcation and/or deploy a second stent at the bifurcation as has been discussed herein.

Figure 26:
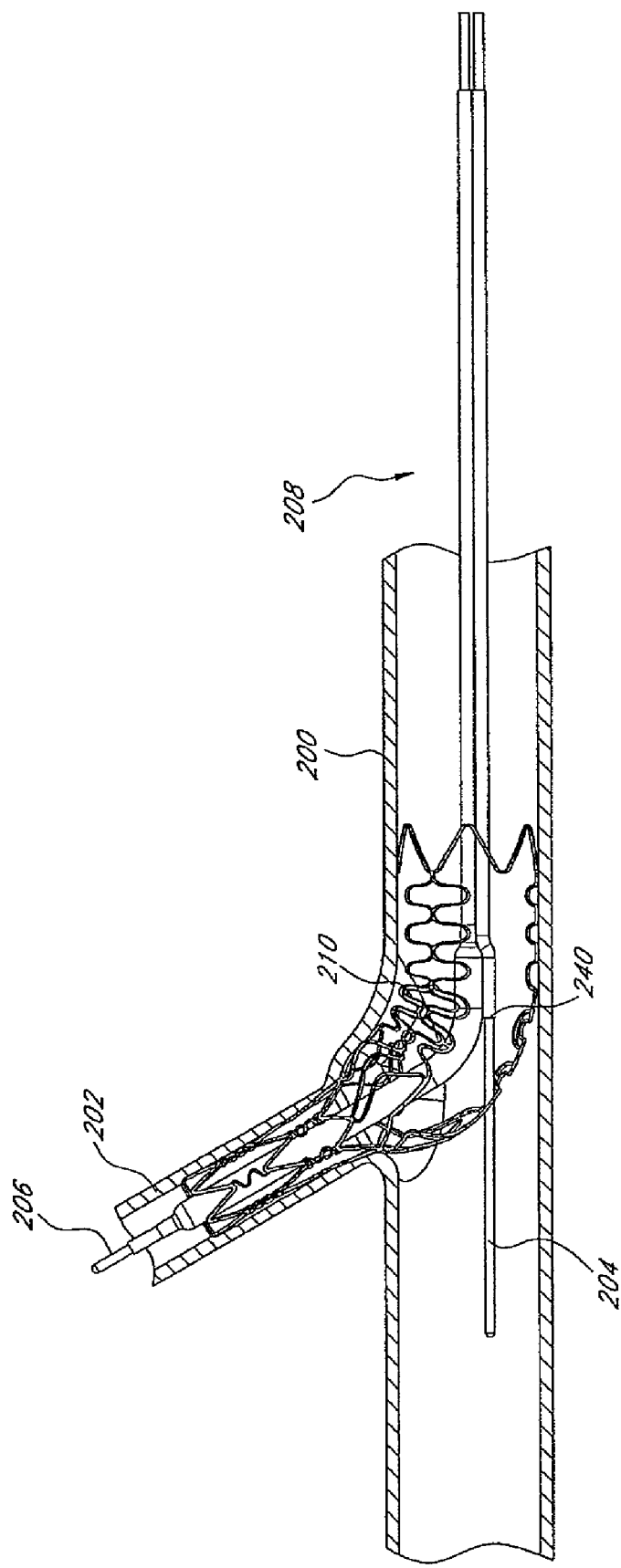
FIG. 26 is a schematic representation as in FIG. 25, showing the second guidewire advanced distally through the fronds.

In FIGS. 25 through 27, the catheter 208 is schematically illustrated as a construct of a separate main vessel lumen attached to a catheter body. However, in any of the foregoing catheters the body construction may be that of a unitary extrusion as has been discussed previously.

The stepped balloon of the present invention may be used in a variety of additional applications. For example, the distal lower diameter section of the device may be used to slightly open a small blood vessel then the system advanced to treat the index lesion with an appropriately sized catheter. In one embodiment the stepped balloon may function as a standard PTCA catheter for the treatment of advanced cardiovascular disease. Specifically in cases where only a small diameter balloon catheter is capable of crossing a diseased lesion, the smaller diameter leading portion of the step balloon may be used to predilate the lesion. The catheter would then be deflated and the larger diameter trailing segment advanced across the lesion. The larger diameter portion of the stepped balloon would then be used to dilate the diseased lesion to a larger diameter. In this way the stepped balloon functions as both a pre-dilation and final dilation catheter.

Although the present invention has been described primarily in the context of a prosthesis adapted for positioning across the Os between a branch vessel and a main vessel prior to the introduction of the main vessel stent, in certain applications it may be desirable to introduce the main vessel stent first. Alternatively, where the prosthesis of the present invention is used provisionally, the main vessel stent may have already been positioned at the treatment site. The main vessel stent may include a side branch opening, or a side branch opening may be formed by advancing a balloon catheter through the wall of the stent in the vicinity of the branch vessel. Thereafter, the prosthesis of the present invention may be advanced into the main vessel stent, though the side wall opening, and into the branch vessel, with the circumferential link positioned within the interior of the main vessel stent. In many of the embodiments disclosed herein, the circumferential link will expand to a diameter which is approximately equal to the expanded diameter of the branch vessel support. Thus, upon initial deployment of the prosthesis, the circumferential link may be expanded to a diameter which is less than the adjacent diameter of the main vessel. If the prosthesis of the present invention is positioned within a previously positioned main vessel stent, it may therefore be desirable to include a post dilatation step to expand the circumferential link up to the inside diameter of the main vessel stent and also to deform the fronds outwardly and rotationally to conform to the interior surface of the main vessel stent.

While the above is a complete description of the preferred embodiments of the invention, various alternatives, modifications, and equivalents may be used. Also, elements or steps from one embodiment can be readily recombined with one or more elements or steps from other embodiments. Therefore, the above description should not be taken as limiting the scope of the invention which is defined by the appended claims.

What is claimed is:

1. A kit for stenting a bifurcation in a vessel, comprising:
   a branch vessel stent, having a proximal end, a distal end, and at least two fronds extending from either the proximal or distal end;
   a circumferential link separated from the branch vessel stent by the at least two fronds; and
   a main vessel stent, separate from the branch vessel stent, the main vessel stent for entrapping the at least two fronds of the branch vessel stent against a vessel wall;
   wherein the at least two fronds have sufficient length to extend into and expandably circumscribe a main vessel wall and reach a portion of the main vessel wall opposing an ostium opening at the intersection of the main vessel and branch vessel when the branch vessel stent is implanted in the branch vessel adjacent to the ostium opening such that a flow path is maintained in the main vessel through the circumferential link and beyond the ostium opening.

2. A kit as in claim 1, additionally comprising a first balloon catheter for deploying the branch vessel stent.

3. A kit as in claim 2, additionally comprising a second balloon catheter for deploying the main vessel stent.

4. A kit as in claim 2, wherein the distal end of the branch vessel stent is carried by a first portion of the first balloon that is inflatable to a first diameter and at least a portion of the at least two fronds is carried by a second portion of the first balloon that is inflatable to a second diameter that is larger than the first diameter.

5. The kit as in claim 2, wherein the first balloon catheter comprises a single, stepped balloon having a proximal section with a larger inflated diameter than an inflated diameter of a distal section.

6. The kit as in claim 2, wherein the first balloon has an inflated profile with a first section having a first diameter, a second section having a second diameter, and a balloon transition in between the first and second sections, the branch vessel stent being carried by the first balloon, and wherein the branch vessel stent has a wall having a first wall pattern adjacent the first section of the balloon, and a second wall pattern adjacent the balloon transition.

7. The kit as in claim 6, wherein the branch vessel stent has a third wall pattern adjacent the second section of the balloon.

8. A kit as in claim 1, wherein the at least two fronds includes at least three fronds.

9. A kit as in claim 1, wherein the at least two fronds comprises a helical configuration.

10. A kit as in claim 1, wherein at least a portion of the at least two fronds comprises a lubricous coating.

11. A kit as in claim 1, comprising an endothelial cell ingrowth surface.

12. A kit as in claim 1, comprising a non thrombogenic surface.

13. A kit as in claim 1, wherein at least a portion of the branch vessel stent comprises a drug coating, and at least a portion of the fronds and the circumferential link are without a drug coating.

14. A kit as in claim 13, wherein the drug coating is configured to produce at least one of a controlled drug release rate, a constant drug release rate, bi-modal drug release rate or a controlled concentration of drug proximate a target vessel wall.

15. A kit as in claim 13, wherein the drug is one of an anti-cell proliferative, anti cell migration, anti-neo plastic, anti inflammatory drug.

16. A kit as in claim 13, wherein the drug is configured to reduce an incidence or amount of restensosis.

17. A kit as in claim 13, wherein the drug coating includes a first coating and a second coating.

18. A kit as in claim 17, wherein the first coating is configured to produce a first drug release rate and the second coating is configured to produce a second drug release rate.

19. A kit as in claim 1, wherein the circumferential link is expandable from a first, reduced diameter to a second, enlarged diameter.

20. A kit as in claim 1, wherein the branch vessel stent is on a first end of at least one of the at least two fronds, and the circumferential link is on a second end of at least one of the at least two fronds.

21. A kit as in claim 1, wherein the circumferential link is radiopaque.

22. A kit as in claim 1, wherein the circumferential link has a greater radiopacity than the fronds.

* * * * *

UNITED STATES PATENT AND TRADEMARK OFFICE
CERTIFICATE OF CORRECTION

PATENT NO. : 7,972,372 B2
APPLICATION NO. : 11/744802
DATED : July 5, 2011
INVENTOR(S) : H. Richard Davis and Aaron Kaplan Page 1 of 1

It is certified that error appears in the above-identified patent and that said Letters Patent is hereby corrected as shown below:

On Title Page 4, Item (56) Line 2, Under Other Publications, please change "Catherization" to --Catheterization--.

On Title Page 4, Item (56) Line 4, Under Other Publications, please change "MD" to --MD,--

In Column 2, Line 37, please change "malaposition" to --malapposition--.

In Column 15, Line 42, please change "and or" to --and/or--.

In Column 16, Line 50, please change "ciclosporina" to --ciclosporin A--.

In Column 16, Lines 59-60, please change "hyrudin," to --hirudin,--.

In Column 17, Line 57, please change "polyphospoeters;" to --polyphosphoesters;--.

In Column 22, Line 9, please change "prosthesis" to --prosthesis.--.

In Column 40, Line 43, in Claim 16, please change "restensosis" to --restenosis--.

Signed and Sealed this
Twenty-fourth Day of April, 2012

David J. Kappos
*Director of the United States Patent and Trademark Office*